United States Patent
Sylvester et al.

(10) Patent No.: US 12,158,512 B2
(45) Date of Patent: *Dec. 3, 2024

(54) SYSTEMS AND METHOD OF PRECISION FUNCTIONAL MAPPING-GUIDED INTERVENTIONAL PLANNING

(71) Applicant: Turing Medical Technologies, Inc, St. Louis, MO (US)

(72) Inventors: Chad Sylvester, St. Louis, MO (US); Deanna Greene, St. Louis, MO (US); Scott Marek, St. Louis, MO (US); Scott Norris, St. Louis, MO (US); Jarod Roland, St. Louis, MO (US); Evan Gordon, St. Louis, MO (US); Timothy Laumann, St. Louis, MO (US); Damien Fair, St. Louis, MO (US); Kenneth Bruener, St. Louis, MO (US); Nico Dosenbach, St. Louis, MO (US)

(73) Assignee: TURING MEDICAL TECHNOLOGIES INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/098,886

(22) Filed: Jan. 19, 2023

(65) Prior Publication Data

US 2023/0228831 A1     Jul. 20, 2023

Related U.S. Application Data

(63) Continuation of application No. 17/116,827, filed on Dec. 9, 2020, now Pat. No. 11,733,332.
(Continued)

(51) Int. Cl.
*G01R 33/48*     (2006.01)
*A61B 5/00*     (2006.01)
(Continued)

(52) U.S. Cl.
CPC ........ *G01R 33/4806* (2013.01); *A61B 5/0036* (2018.08); *A61B 5/0042* (2013.01);
(Continued)

(58) Field of Classification Search
CPC ... G01R 33/4806; A61B 5/0042; A61B 5/055; A61B 5/4064; A61B 2576/026
See application file for complete search history.

(56) References Cited

U.S. PATENT DOCUMENTS 7,894,903 B2   2/2011   John
8,027,730 B2   9/2011   John
(Continued)

FOREIGN PATENT DOCUMENTS

CN   103325119 A   9/2013
CN   102855491 B   3/2016
(Continued)

OTHER PUBLICATIONS

Fox, M. D., et al. "Identification of reproducible individualized targets for treatment of depression with TMS based on intrinsic connectivity." Neuroimage 66 (2013): 151-160.
(Continued)

*Primary Examiner* — Dixomara Vargas
(74) *Attorney, Agent, or Firm* — Quarles & Brady, LLP

(57) ABSTRACT

A method of performing personalized neuromodulation on a subject is provided. The method includes acquiring functional magnetic resonance imaging (fMRI) data of a brain of the subject. The method also includes calculating functional connectivity of the brain between a voxel in a subcortical region of the brain and a voxel in a cortical region of the brain, based on the fMRI data. The method also includes identifying a target location in the brain to be targeted by neuromodulation based on the calculated functional connectivity.

14 Claims, 42 Drawing Sheets
(27 of 42 Drawing Sheet(s) Filed in Color)

Related U.S. Application Data

(60) Provisional application No. 62/955,488, filed on Dec. 31, 2019, provisional application No. 62/945,524, filed on Dec. 9, 2019.

(51) Int. Cl.

| | | |
|---|---|---|
| *A61B 5/055* | (2006.01) | |
| *A61N 1/36* | (2006.01) | |
| *A61N 1/372* | (2006.01) | |
| *G01R 33/563* | (2006.01) | |

(52) U.S. Cl.
CPC ............ *A61B 5/055* (2013.01); *A61B 5/4064* (2013.01); *A61B 5/7246* (2013.01); *A61N 1/36189* (2013.01); *A61N 1/3727* (2013.01); *G01R 33/56366* (2013.01); *A61B 2576/026* (2013.01)

(56) References Cited

U.S. PATENT DOCUMENTS

| | | | |
|---|---|---|---|
| 8,059,879 B2 | 11/2011 | Tsukimoto | |
| 8,965,093 B2 | 2/2015 | Fan | |
| 9,116,835 B1 | 8/2015 | Smyth | |
| 9,179,850 B2 | 11/2015 | Wingeier | |
| 9,586,053 B2 | 3/2017 | Moffitt | |
| 9,694,178 B2 | 7/2017 | Ruffini | |
| 10,137,307 B2 | 11/2018 | Pascual-Leone et al. | |
| 10,149,618 B1 | 12/2018 | Tandon | |
| 10,350,413 B2 | 7/2019 | Moffitt | |
| 10,449,384 B2 | 10/2019 | Williams | |
| 10,463,855 B2 | 11/2019 | Ruffini | |
| 11,213,215 B2 * | 1/2022 | Williams | G01R 33/565 |
| 11,733,332 B2 * | 8/2023 | Sylvester | A61N 1/36189 |
| | | | 324/309 |
| 2002/0103429 A1 * | 8/2002 | deCharms | A61B 5/055 |
| | | | 600/410 |
| 2005/0283053 A1 * | 12/2005 | deCharms | A61B 5/486 |
| | | | 600/300 |
| 2006/0004422 A1 | 1/2006 | De Ridder | |
| 2009/0024021 A1 | 1/2009 | George | |
| 2012/0083647 A1 | 4/2012 | Scheinin | |
| 2013/0030499 A1 | 1/2013 | Pouratian | |
| 2013/0066350 A1 | 3/2013 | Mishelevich | |
| 2013/0116540 A1 * | 5/2013 | Li | A61B 5/0042 |
| | | | 600/410 |
| 2013/0211238 A1 * | 8/2013 | DeCharms | A61B 5/4848 |
| | | | 600/407 |
| 2013/0317580 A1 | 11/2013 | Simon | |
| 2015/0094562 A1 | 4/2015 | Hardy | |
| 2015/0119689 A1 | 4/2015 | Pascual-Leone et al. | |
| 2015/0362574 A1 | 12/2015 | Wu | |
| 2016/0129276 A1 | 5/2016 | Fried | |
| 2017/0113046 A1 | 4/2017 | Fried | |
| 2018/0360343 A1 | 12/2018 | Lee | |
| 2018/0368720 A1 * | 12/2018 | Lee | A61B 5/246 |
| 2019/0090749 A1 | 3/2019 | Leuthardt | |
| 2019/0201691 A1 | 7/2019 | Poltorak | |
| 2020/0008725 A1 | 1/2020 | Bach | |
| 2020/0288980 A1 | 9/2020 | Stem | |
| 2020/0289044 A1 * | 9/2020 | Liston | A61B 5/0042 |
| 2021/0170180 A1 * | 6/2021 | Dosenbach | A61B 5/0042 |
| 2021/0213300 A1 | 7/2021 | Hedaya | |
| 2021/0333343 A1 * | 10/2021 | Dosenbach | A61N 1/36064 |
| 2021/0393955 A1 | 12/2021 | Hagedorn | |
| 2021/0401289 A1 | 12/2021 | Yamashita | |
| 2022/0133194 A1 | 5/2022 | Bach | |
| 2022/0139530 A1 | 5/2022 | Kollada | |
| 2022/0293244 A1 | 9/2022 | Leuthardt | |
| 2023/0050594 A1 * | 2/2023 | Dosenbach | A61B 5/7246 |
| 2023/0115330 A1 * | 4/2023 | Hermosillo | A61B 5/0042 |
| | | | 607/45 |
| 2024/0032815 A1 * | 2/2024 | Wei | A61B 5/055 |

FOREIGN PATENT DOCUMENTS

| | | |
|---|---|---|
| CN | 105916547 A | 8/2016 |
| CN | 104337518 B | 3/2017 |
| CN | 106823137 A | 6/2017 |
| CN | 108366752 A | 8/2018 |
| CN | 109171726 A | 1/2019 |
| CN | 106023194 B | 4/2019 |
| CN | 110136093 A | 8/2019 |
| EP | 3060295 A1 | 8/2016 |
| WO | 2006102370 A2 | 9/2006 |
| WO | 2015059545 A1 | 4/2015 |
| WO | 2019160754 A1 | 8/2019 |

OTHER PUBLICATIONS

Hart, M. G., et al. "Functional connectivity networks for preoperative brain mapping in neurosurgery." Journal of neurosurgery 126.6 (2016): 1941-1950.

Mitchell, T. J., et al. "A novel data-driven approach to preoperative mapping of functional cortex using resting-state functional magnetic resonance imaging." Neurosurgery 73.6 (2013): 969-983.

Moreno-Ortega, M., et al. "Resting state functional connectivity predictors of treatment response to electroconvulsive therapy in depression." Scientific reports 9.1 (2019): 1-19.

Opitz, A., et al. "An integrated framework for targeting functional networks via transcranial magnetic stimulation." Neuroimage 127 (2016): 86-96.

\* cited by examiner

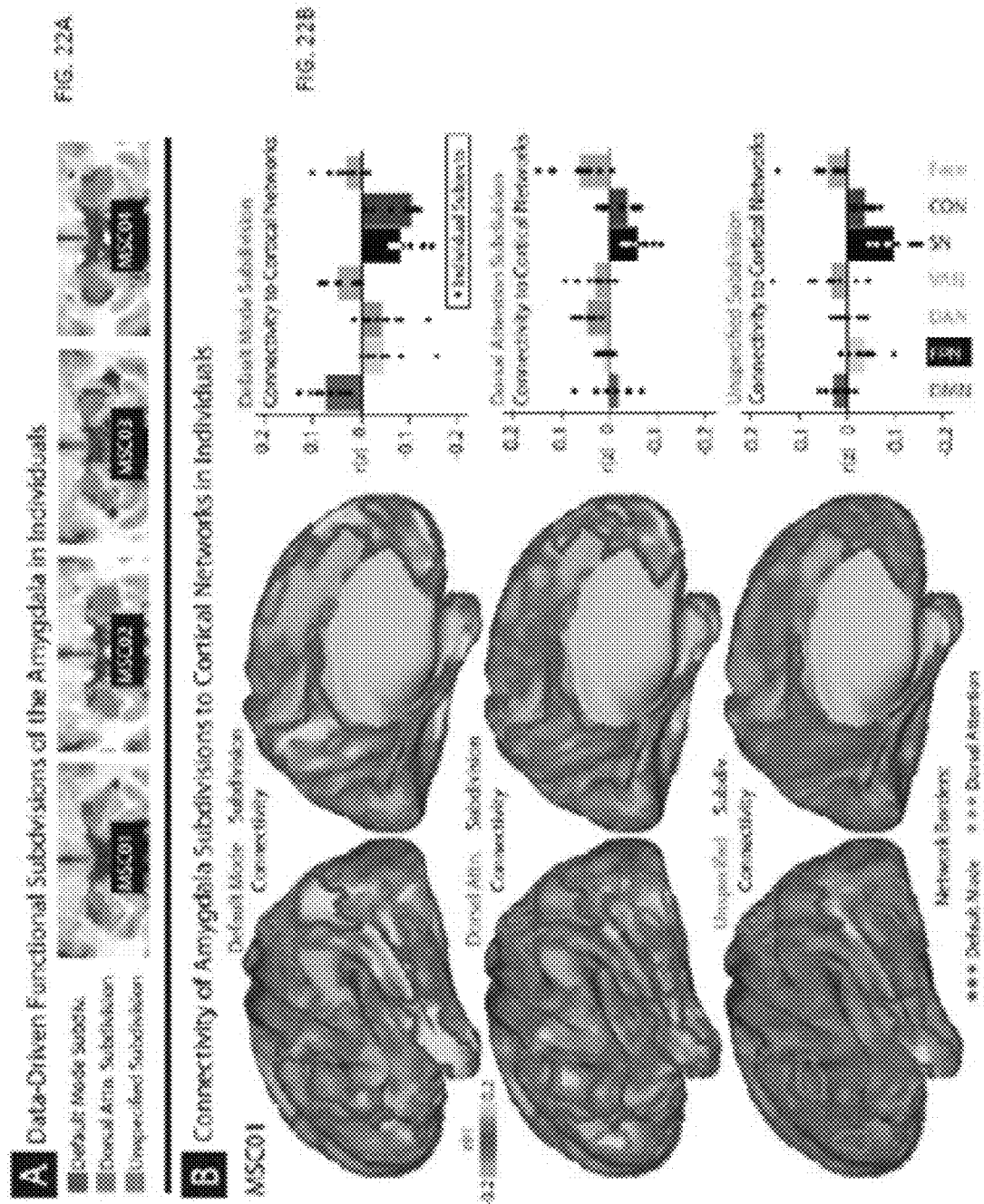

SYSTEMS AND METHOD OF PRECISION FUNCTIONAL MAPPING-GUIDED INTERVENTIONAL PLANNING

CROSS REFERENCE TO RELATED APPLICATIONS

This application is a continuation of U.S. application Ser. No. 17/116,827 filed Dec. 9, 2020, which claims the benefit of U.S. Provisional Application No. 62/945,524 filed Dec. 9, 2019, and U.S. Provisional Application No. 62/955,488 filed Dec. 31, 2019, the entire disclosures of which are hereby incorporated by reference in their entirety.

STATEMENT REGARDING FEDERALLY SPONSORED RESEARCH & DEVELOPMENT

This invention was made with government support under grants MH104592, N5088590, and MH109983 awarded by the National Institute of Health. The government has certain rights in the invention.

BACKGROUND

Psychiatric disorders are a common cause of severe and long-term disability and socioeconomic burden. In some patients, treatment modalities of drug therapy and psychotherapy do not produce sufficient therapeutic effects or induce intolerable side effects. For these patients, neuromodulation has been suggested as a potential treatment modality. Neuromodulation is one of the fastest-growing areas of medicine, and is the process of inhibition, stimulation, modification, regulation or therapeutic alteration of activity, electrically or chemically, in the central, peripheral or autonomic nervous systems. Neuromodulation includes deep brain stimulation, vagal nerve stimulation, and transcranial magnetic and electrical stimulation. Neuromodulation aims to treat chronic neurological or psychiatric diseases by surgically targeting deep brain nuclei and pathways involved in the mediation of the symptoms in order to stimulate, inhibit, or otherwise modify/modulate pathological activity.

Neural structures such as cortical and/or subcortical structures are targeted using deep brain stimulation (DBS) for treatment of neurological and psychiatric disorders, including essential tremor, Parkinson disease, dystonia, Tourette syndrome, obsessive compulsive disorder, and treatment-resistant depression. Yet, specific target structures have variable success rates. DBS of the ventral intermediate nucleus of the thalamus for treatment of essential tremor results in over 80% tremor reduction in all patients, while stimulation of the globus pallidus for treatment of dystonia results in only 30-50% symptom improvement across all patients and >75% improvement in only 33% of patients.

BRIEF DESCRIPTION

The present disclosure provides systems and methods for functional mapping-guided intervention planning. For example, the systems and methods provided herein may be used to achieve precision functional mapping-guided brain intervention targeting (PFM-GBIT) of a subject to improve success of interventions that target subcortical structures, such as DBS, by more-accurately providing targets that are efficacious treatment sites for neuromodulation. Other treatment approaches that may benefit from precision functional mapping-guided intervention planning or targeting include transcranial magnetic stimulation (TMS), transcranial direct current stimulation (tDCS), focused ultrasound, and the like. A target location may be identified by calculating functional connectivity of a brain a subject between a voxel in a subcortical region of the brain and a voxel in a cortical region of the brain. In some aspects, guiding neuromodulation target locations may be tailored to the individual subject using individual-specific precision functional connectivity magnetic resonance imaging (fc-MRI).

In one aspect, a method of performing functional mapping-guided brain intervention targeting of a subject is provided. The method includes acquiring functional magnetic resonance imaging (fMRI) data of a brain of the subject. The method also includes calculating functional connectivity of the brain between a voxel in a subcortical region of the brain and a voxel in a cortical region of the brain, based on the fMRI data. The method also includes identifying a target location in the brain to be targeted by neuromodulation based on the calculated functional connectivity.

In another aspect, a system for p functional mapping-guided brain intervention targeting of on a subject is provided. The system includes a computing device that includes a processor electrically coupled to a memory, the processor programmed to acquire functional magnetic resonance imaging (fMRI) data of a brain of the subject. The processor is also programmed to calculate functional connectivity of the brain between a voxel in a subcortical region of the brain and a voxel in a cortical region of the brain, based on the fMRI data. The processor is further programmed to identify a target location in the brain to be targeted by neuromodulation based on the calculated functional connectivity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure will become better understood when the following detailed description is read with reference to the accompanying drawings in which like characters represent like parts throughout the drawings, wherein:

FIG. 22A shows functional subdivisions of the amygdala in individuals;

FIG. 22B shows connectivity of subdivisions to cortical functional networks in individuals;

Unless otherwise indicated, the drawings provided herein are meant to illustrate features of embodiments of the disclosure. These features are believed to be applicable in a wide variety of systems including one or more embodiments of the disclosure. As such, the drawings are not meant to include all conventional features known by those of ordinary skill in the art to be required for the practice of the embodiments disclosed herein.

DETAILED DESCRIPTION

This disclosure is generally directed toward systems and methods for functional mapping and functional mapping-guided brain intervention targeting of a subject. Precision functional mapping-guided brain intervention targeting (PFM-GBIT) of a subject may improve success of interventions that target subcortical structures, such as DBS by more accurately providing targets that are more likely to provide efficacious treatment upon neuromodulation. In some aspects, a method includes acquiring functional magnetic resonance imaging (fMRI) data of a subject, calculating functional connectivity of the subject's brain from the subject's fMRI data, and identifying a target location in the subject's brain to be targeted by neuromodulation based on the calculated functional connectivity.

The disclosure is further directed to examining functional network specificity and integration within the subcortex, and individual variability and similarity of functional organization across subjects. This disclosure is additionally directed to precision functional mapping that may be applied to the amygdala to characterize the locations of functional subdivisions within the amygdala, as well as the strength, direction, and timing of functional connectivity of each of these subdivisions to the rest of the brain in individuals. Applications of precision functional mapping of the amygdala include diagnosis, prognosis, and guiding of treatment selection in individual subjects with psychiatric, neurologic, and other medical disorders.

Figure 1A:
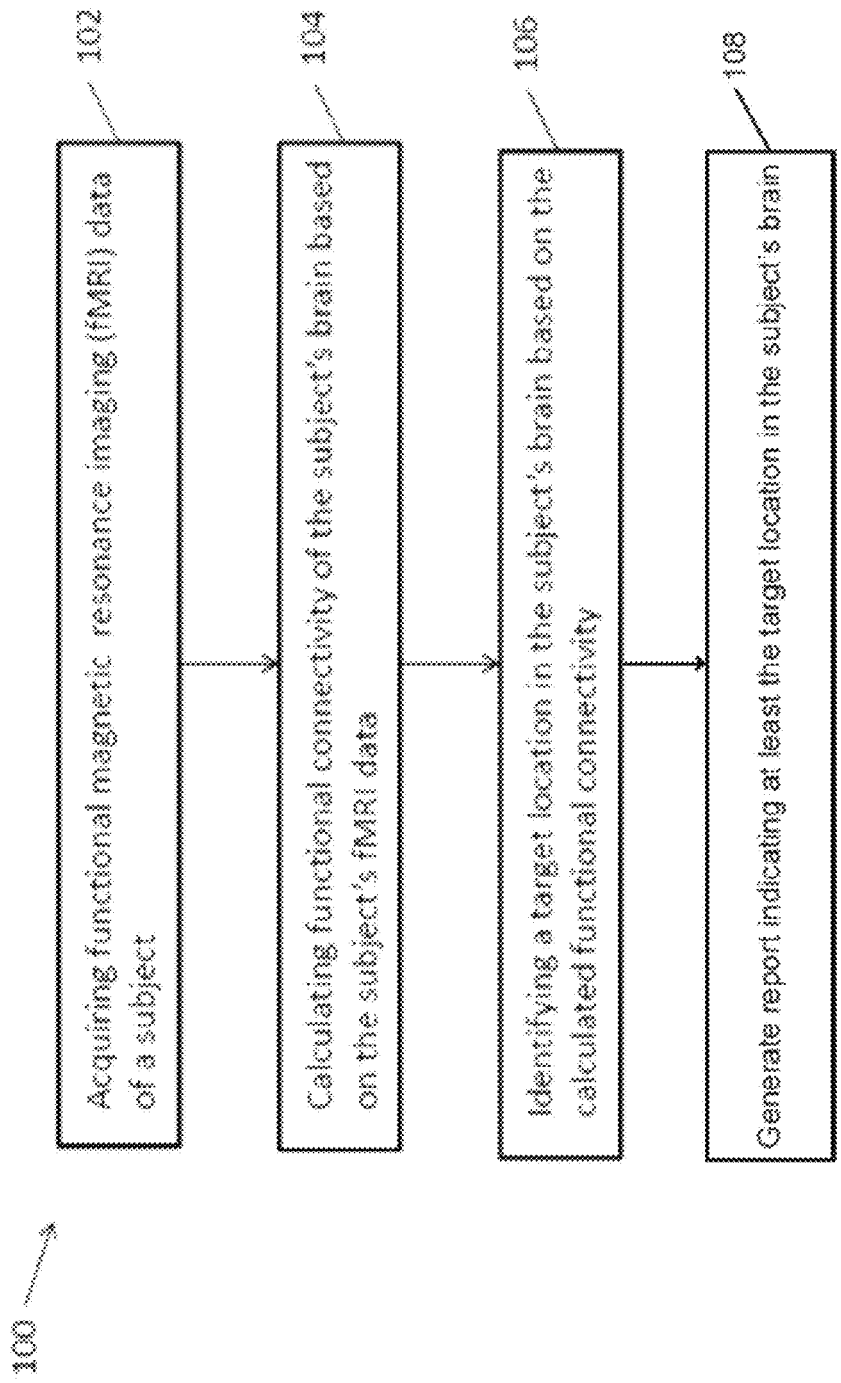
FIG. 1A is a flow chart of an exemplary method in accordance with the present disclosure.

FIG. 1A is a flow chart of a non-limiting example method 100 for performing mapping of a subject's brain in accordance with the present disclosure. The method 100 includes acquiring 102 functional magnetic resonance imaging (fMRI) data of a brain of a subject that at least includes acquiring resting-state fMRI (rs-fMRI) data. A subject may be a human, an animal, a phantom, or the like.

Functional MRI (fMRI) has been used to study and diagnose brain functions based on observations that when neural activities increase in a particular area of the brain, magnetic resonance (MR) signals increase by a small amount in that particular area because of an effect called the blood oxygenation level dependent (BOLD) effect. In some aspects of an fMRI image acquisition, the subject undertakes a task or is subjected to a stimulus and alternates between the task/stimulus and a non-task/non-stimulus state, referred to as a control state. In one non-limiting example of alternating between a task and a control, 30-second blocks of looking at a visual stimulus may be alternated with 30-second blocks with eyes closed. The acquired data may be analyzed to identify brain areas in which the MR signals influenced by the BOLD effect have a matching pattern of changes, because these identified areas are areas in the brain activated by the stimulus. In this example, the visual stimulus is designed to stimulate the visual cortex at the back of the subject's head, such that it is the area in the brain reflected as activated in the acquired data. Such a study may be referred to as a task fMRI stimulus-based fMRI study because tasks or stimuli are used during the data acquisition to yield task or stimulus fMRI data.

In contrast to task or stimulus-based fMRI, rs-fMRI acquires data reflecting the BOLD contrast mechanism without requiring the subject to perform tasks or respond to stimuli to elicit a BOLD contrast that is responsive to the tasks or stimuli. Instead, the subject is at "rest" the MR scanner for a period of time, for example, with eyes closed or staring at a fixed point, while data is acquired, which is referred to rs-fMRI data. The present disclosure recognizes that rs-fMRI acquisitions are highly correlated to low frequency (for example, a low frequency may be in a range of 0.01-0.1 Hz, or may be less than 0.1 Hz) changes in the BOLD signals between different areas of the brain. Furthermore, the present disclosure recognizes that low-frequency changes in the BOLD signals are correlated with the brain's functional connectivity. Further still, the present disclosure recognizes that functional connectivity is a temporal correlation of a neurophysiological index, such as low frequency fluctuations of blood flow and oxygenation, measured in different brain areas. Thus, the present disclosure recognizes that rs-fMRI data can be advantageously used to map functional connectivity and, either alone or in combination with task fMRI data, derive maps of a subject's brain that are particularly useful for interventional planning and execution.

In Referring again to FIG. 1A, as described above, the fMRI data acquired 102 at least includes rs-fMRI data. Thus, the method 100 includes calculating 104 functional connectivity of the brain between a voxel in a subcortical region of the brain and a voxel in a cortical region of the brain, based on at least rs-fMRI data. The method 100 then includes identifying 106 a target location in the brain of the subject to be targeted by neuromodulation based on the calculated functional connectivity. The identified region may be in the so-called cortical region or in the subcortical region. Cortical regions of the brain are the outer layer of the neural tissue of the cerebrum of the brain and include cerebral cortices such as motor cortex and sensory cortex. Subcortical regions are the part of brain beneath cerebral cortex, and include basal ganglia, thalamus, and amygdala. Irrespective of the particular region of the brain being studied, a report is generated 108 that at least indicates the target location. As one non-limiting example, the target location may be a target location for neuromodulation. Thus, the method 100 may further facilitate surgical planning for implantation of a neuromodulation device and even the ultimate performance of neuromodulation directed at the identified target location.

Thus, as will be further detailed, a system and method are provided to perform surgical or therapeutic planning based on functional connectivity, instead of anatomical analysis with or without the combination of stimulus- or task-based response maps. Reports, maps, or images created using the systems and methods described herein that utilize rs-fMRI data to reflect functional connectivity via low-frequency changes is referred to herein as precision functional mapping (PFM).

Figure 1B:
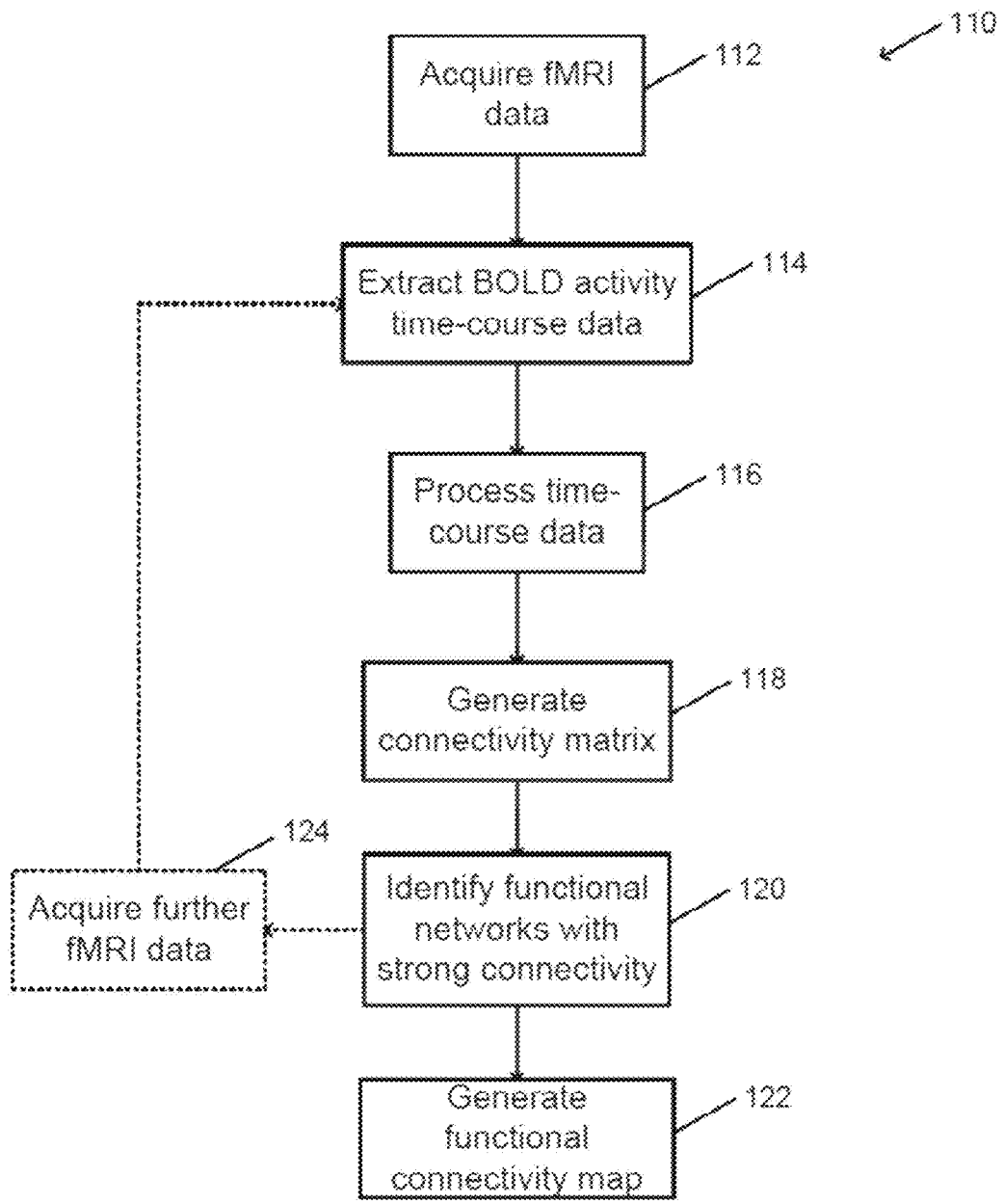
FIG. 1B is a flow chart of further exemplary methods in accordance with the present disclosure.

The systems and methods in accordance with the present disclosure may be referred to as precision functional mapping-guided brain intervention targeting (PFM-GBIT). Referring to FIG. 1B, a method 110 determining target locations may be tailored to the individual subject using individual-specific precision functional connectivity magnetic resonance imaging (fc-MRI). Treatments of particular neurological and psychological disorders and on particular structures of the brain as disclosed herein are examples only. The systems and methods disclosed herein may be used on any other suitable structures of the brain and as part of treatment of any other neurological and psychological disorders. Deep brain stimulation (DBS) is a form of neuromodulation in clinical use. DBS is a procedure in which a neurostimulator is surgically implanted into the brain for the purpose of treating neurological disorders, such as Parkinson's disease, dystonia, essential tremor, obsessive compulsive disorder, epilepsy. Unfortunately, DBS is not always effective, and has vastly different success rates, depending on the brain structure that is stimulated. There is work, primarily in Parkinson disease (PD), investigating the relationship between anatomical locations of stimulation and clinical outcome. In particular, two recent studies pinpointed a specific subthalamic nucleus location as a predictor of treatment response in PD. Although this work is promising, this anatomically-defined location still only explains 27% of the variance in clinical outcome. Further, there is a high degree of overlap between stereotactic coordinates of responders and non-responders. Thus, better accounts of function and individual neuroanatomical variability may improve efficacy of DBS as well as other treatment approaches such as transcranial magnetic stimulation (TMS), transcranial direct current stimulation (tDCS) and focused ultrasound.

In contrast to at least some known methods, the present disclosure uses PFM-GBIT and functional connectivity, instead of anatomical coordinates and task/stimulus mapping, to guide planning for neuromodulation, such as DBS lead placement or targets for TMS, tDCS, and focused ultrasound. That is, the present disclosure recognize that therapy device deployment can be substantially improved by targeting locations based on function, rather than anatomy and/or stimulus/task mapping. Previous methods use group average imaging estimates, which smooth over individual-specific features. Using the PFM of the present disclosure, different subcortical subregions were shown to have individually-variable functional connectivity. The present disclosure recognizes that this may account for variability in clinical outcomes and lack of ability to identify optimal stimulation regions in group-level studies of DBS outcomes. Since no two brains are the same, an approach tailored to the connectivity of the individual subject, not to a group average, has the potential to be effective for precision medicine.

The systems and methods of the present disclosure allow one to use PFM-GBIT. In particular, referring to FIG. 1B, the method 110 uses PFM-GBIT to characterize the functional network organization of cortical and subcortical structures at the level of the individual. The method 110 starts with acquiring fMRI data 112, which includes rs-fMRI data, from which BOLD activity time-course data may be extracted 114. BOLD activity time-course data may be extracted from each voxel in the cortex and subcortex, such as basal ganglia and thalamus and/or each vertex in a cortical functional network. Voxels are 3D pixels that may be used for 3D volumetrics. Vertices are tiles of the tessellation that makes up the cortical surface, and may be used when data is projected onto the cortical surface. The time-course data for each voxel or vertices can then be processed 116. For example, cortical time-course data, time-course data for voxels/vertices in the cortical region, can be averaged across all vertices in each cortical functional network defined for each individual (e.g., somatomotor hand network, cingulo-opercular network, and default-mode network). Then, a connectivity matrix can be generated 118. For example, a subcortical voxel-to-cortical network connectivity matrix can be generated 118 for an individual by computing the correlation, such as Pearson correlation, between the time-course data of each subcortical voxel and of each vertex in each cortical network. Then, for each subcortical voxel, the functional networks with strong connectivity to that voxel can be identified 120. A strong connectivity may be determined as the computed correlation above a threshold. In one non-limiting example, a threshold may be set at 0.7. In another non-limiting example, a threshold may be in a range of 0.2-0.3. The threshold can vary based on the subject, data quality, BOLD sequence used, or structure specific considerations (e.g. cortex vs. thalamus vs. cerebellum). Any appropriate threshold may be used with higher values reflecting a stronger, tighter correlation and lower values being more inclusive of voxels with a looser connection. This process may identify subregions within subcortical structures with functional connectivity to specific functional networks for a given individual. This information can then be used to guide selection of cortical and subcortical neuromodulation target locations for that individual. For example, a functional connectivity map can be generated 122.

Typically, rs-fMRI studies require large amounts of data in order to compile sufficient information for a subject, which can present challenges when considering the effects of subject motion and image artifacts over the duration of a single rs-fMRI scan. In some configurations and in accordance with the present disclosure, an individual can undergo multiple rs-fMRI scan sessions in order to obtain desired quantities of scan data and/or boost the reliability of data per individual. In this way non-invasive data acquisition for precision pre-operative analysis can be increased to guide subsequent invasive procedures. Notably, fMRI mapping is significantly cheaper and less risky than intraoperative mapping with invasive electrophysiology recordings.

Continuing with respect to FIG. 1B, in some optional configurations, data may be acquired across multiple imaging sessions 124 and integrative zones in the subcortical region can be determined based on strong functional connectivity with more than one functional networks 120. A subcortical voxel is in an integrative zone if the voxel exhibits strong functional connectivity with more than one functional network. On the other hand, if the voxel does not exhibit strong functional connectivity with more than one functional network, the subcortical voxel is in a network-specific zone. In one configuration, a winning functional network for a subcortical voxel is determined as a functional network that has the highest correlation with the subcortical voxel or a correlation above a threshold. A subcortical voxel may be in an integrative zone if correlations with one or more functional networks other than the winning functional network are above a threshold of the highest correlation. In some aspects, a threshold may range between 65%-70%. In one non-limiting example, a threshold may be set at 66.7%. That is, if there are more than one other network having correlations with the subcortical voxel more than 66.7% of the highest correlation, the subcortical voxel is in an integrative zone. On the other hand, if no other functional networks have correlations with the subcortical voxel that are above that threshold, the subcortical voxel is in a network-specific zone, where the subcortical voxel may be specific to the winning functional network. Neuromodulation of voxels in an integrative zone may be more effective in treatment of diseases than of voxels in a network-specific zone. Any of a variety of specific threshold values may be selected based on the clinical application or the like.

In some configurations, the methods and systems in accordance with the present disclosure relate to determining the functional connectivity of the individual, such as in the basal ganglia and thalamus, with cortical networks. The systems and methods provided herein can be used to examine functional network specificity and integration within the subcortex, and individual variability and similarity of functional organization across subjects. The systems and methods for PFM provided herein can be used to aid in the advancement of understanding of individual cortico-subcortical systems, which is clinically relevant for precise, subject-specific treatment of neurological and psychiatric disorders.

In some configurations, the methods and systems described herein are applied with respect to amygdala. Precision functional mapping of the amygdala is a method of characterizing the locations of functional subdivisions within the amygdala as well as the strength and timing of functional connectivity of each of these subdivisions to the cortical functional networks in an individual. Applications of precision functional mapping of the amygdala include diagnosis, prognosis, and guiding of treatment selection in individual subjects with psychiatric, neurologic, and other medical disorders.

Precision functional mapping of the amygdala may address challenges in neuromodulation based on group-averaged anatomical coordinates, and places the amygdala and its subdivisions within the network organization of the human brain by adopting an individualized approach. Precision mapping techniques may be used to define amygdala subdivisions of individuals on the basis of functional connectivity of the amygdala with cortex. In one example, amygdala subdivisions are determined as clusters in the amygdala based on the functional connectivities between voxels in the amygdala and vertices in cortical networks. A lag analysis may be used to estimate a time delay between functional connectivities of each pair of voxel/vertex, and may be applied to determine the timing of infra-slow activity (ISA, <0.1 Hz) in amygdala subdivisions relative to cortical networks. The magnitude, strength, and timing of amygdala subdivision connectivity to each cortical vertex is a biomarker and is used for diagnosis, prognosis, and treatment selection of a wide range of psychiatric, neurologic, and medical illnesses. Target locations for treatments, therefore, may be identified based on the strength, direction, and/or timing of the functional connectivity. Importantly, the subdivisions, the cortical networks, and the connectivity metrics are all individualized, to allow for personalized medicine applications.

The systems and methods applied with respect to the amygdala are advantageous for several reasons. Prior human fMRI studies have examined functional connections between the amygdala and specific cortical regions and their associations with psychiatric symptoms. However, this prior work has often relied on describing functional connectivity between pre-defined anatomic partitions of the amygdala and cortical locations defined by averaging across large groups of subjects. Specifically, many prior studies of amygdala connectivity in humans use a single spatial template to define centromedial, superficial, and laterobasal partitions of the amygdala in all participants. In one particular study, this 3-partition template used for imaging studies is derived from a study that examined postmortem cytoarchitecture and chemoarchitecture in 10 individuals at an average age of 65 years. Probabilistic locations of the centromedial, superficial, and laterobasal partitions were defined as spatial locations in which at least 5 of these individuals had a particular partition. Yet, there was substantial variation in the location and spatial extent of the 3 amygdala partitions across individuals. In addition, recent work has revealed that individuals may vary in the layout of functional brain networks on the cerebral cortex and that brain-behavior relations may be stronger in individualized network maps than in group-averaged templates. This spatial variability in the location of amygdala partitions and in layout of cortical networks may have confounded the ability to precisely define amygdala-cortical network relations in individuals. One consequence is that there is a suboptimal foundation for the use of amygdala functional connectivity as a biomarker in clinical settings. Precision mapping of the amygdala circumvents these issues and provides reliable, individualized biomarkers, and neuromodulation target sites.

Figure 2:
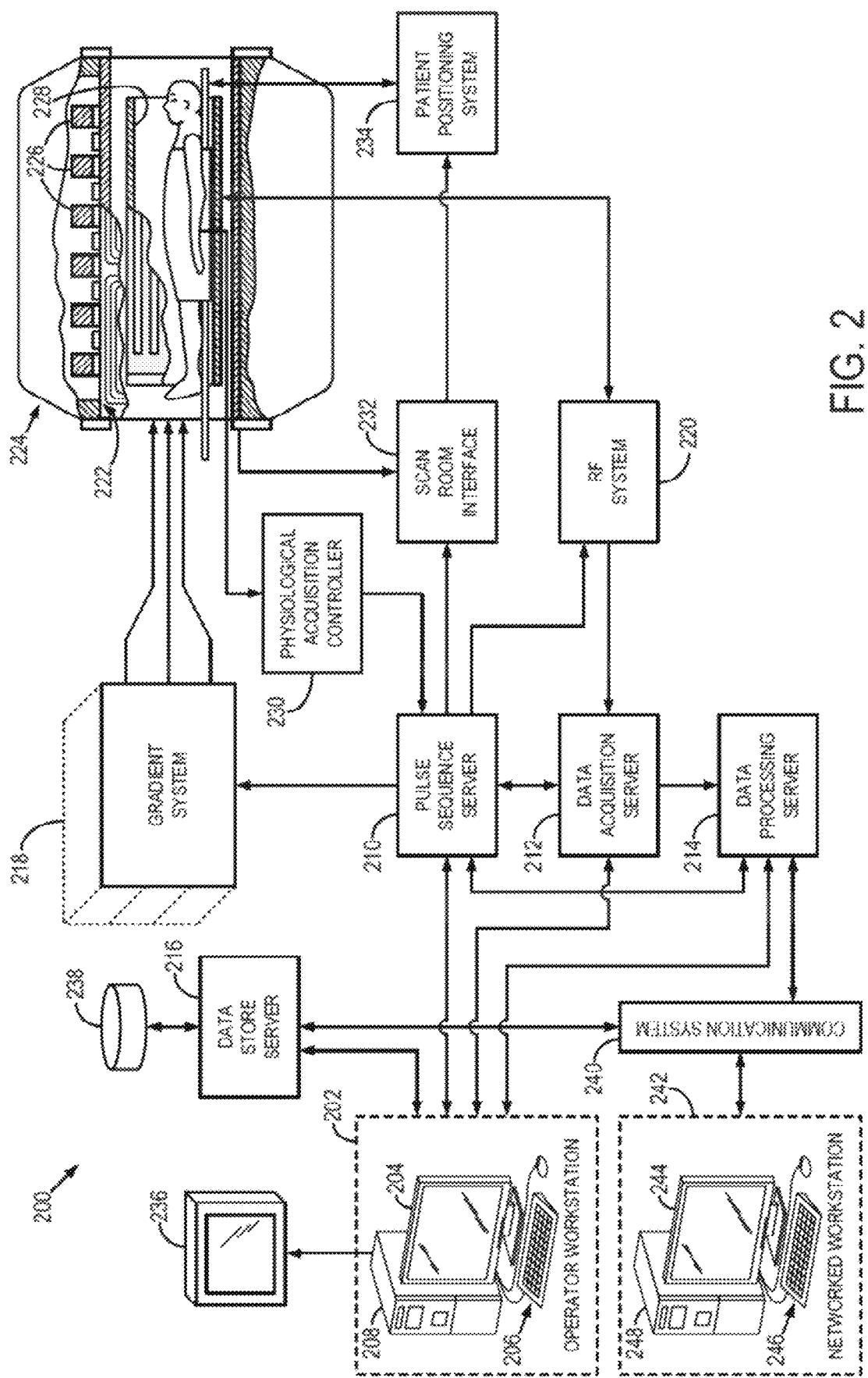
FIG. 2 is a schematic diagram of an exemplary system for performing magnetic resonance imaging in accordance with the present disclosure.

Referring particularly now to FIG. 2, an example of an MRI system 200 that can implement the methods described here is illustrated. The MRI system 200 includes an operator workstation 202 that may include a display 204, one or more input devices 206 (e.g., a keyboard, a mouse), and a processor 208. The processor 208 may include a commercially available programmable machine running a commercially available operating system. The operator workstation 202 provides an operator interface that facilitates entering scan parameters into the MRI system 200. The operator workstation 202 may be coupled to different servers, including, for example, a pulse sequence server 210, a data acquisition server 212, a data processing server 214, and a data store server 216. The operator workstation 202 and the servers 210, 212, 214, and 216 may be connected via a communication system 240, which may include wired or wireless network connections.

The pulse sequence server 210 functions in response to instructions provided by the operator workstation 202 to operate a gradient system 218 and a radiofrequency ("RF") system 220. Gradient waveforms for performing a prescribed scan are produced and applied to the gradient system 218, which then excites gradient coils in an assembly 222 to produce the magnetic field gradients $G_x$, $G_y$, and $G_z$ that are used for spatially encoding magnetic resonance signals. The gradient coil assembly 222 forms part of a magnet assembly 224 that includes a polarizing magnet 226 and a whole-body RF coil 228.

RF waveforms are applied by the RF system 220 to the RF coil 228, or a separate local coil to perform the prescribed magnetic resonance pulse sequence. Responsive magnetic resonance signals detected by the RF coil 228, or a separate local coil, are received by the RF system 220. The responsive magnetic resonance signals may be amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the prescribed scan and direction from the pulse sequence server 210 to produce RF pulses of the desired frequency, phase, and pulse amplitude waveform. The generated RF pulses may be applied to the whole-body RF coil 228 or to one or more local coils or coil arrays.

The RF system 220 also includes one or more RF receiver channels. An RF receiver channel includes an RF preamplifier that amplifies the magnetic resonance signal received by the coil 228 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 210 may receive patient data from a physiological acquisition controller 230. By way of example, the physiological acquisition controller 230 may receive signals from a number of different sensors connected to the patient, including electrocardiograph ("ECG") signals from electrodes, or respiratory signals from a respiratory bellows or other respiratory monitoring devices. These signals may be used by the pulse sequence server 210 to synchronize, or "gate," the performance of the scan with the subject's heart beat or respiration.

The pulse sequence server 210 may also connect to a scan room interface circuit 232 that receives signals from various sensors associated with the condition of the patient and the magnet system. Through the scan room interface circuit 232, a patient positioning system 234 can receive commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, so that data is not lost by data overrun. In some scans, the data acquisition server 212 passes the acquired magnetic resonance data to the data processor server 214. In scans that require information derived from acquired magnetic resonance data to control the further performance of the scan, the data acquisition server 212 may be programmed to produce such information and convey it to the pulse sequence server 210. For example, during pre-scans, magnetic resonance data may be acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also process magnetic resonance signals used to detect the arrival of a contrast agent in a magnetic resonance angiography ("MRA") scan. For example, the data acquisition server 212 may acquire magnetic resonance data and processes it in real-time to produce information that is used to control the scan.

The data processing server 214 receives magnetic resonance data from the data acquisition server 212 and processes the magnetic resonance data in accordance with instructions provided by the operator workstation 202. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 214 are conveyed back to the operator workstation 202 for storage. Real-time images may be stored in a data base memory cache, from which they may be output to operator display 202 or a display 236. Batch mode images or selected real time images may be stored in a host database on disc storage 238. When such images have been reconstructed and transferred to storage, the data processing server 214 may notify the data store server 216 on the operator workstation 202. The operator workstation 202 may be used by an operator to archive the images, produce films, or send the images via a network to other facilities.

The MRI system 200 may also include one or more networked workstations 242. For example, a networked workstation 242 may include a display 244, one or more input devices 246 (e.g., a keyboard, a mouse), and a processor 248. The networked workstation 242 may be located within the same facility as the operator workstation 202, or in a different facility, such as a different healthcare institution or clinic.

The networked workstation 242 may gain remote access to the data processing server 214 or data store server 216 via the communication system 240. Accordingly, multiple networked workstations 242 may have access to the data processing server 214 and the data store server 216. In this manner, magnetic resonance data, reconstructed images, or other data may be exchanged between the data processing server 214 or the data store server 216 and the networked workstations 242, such that the data or images may be remotely processed by a networked workstation 242.

Figure 3A:
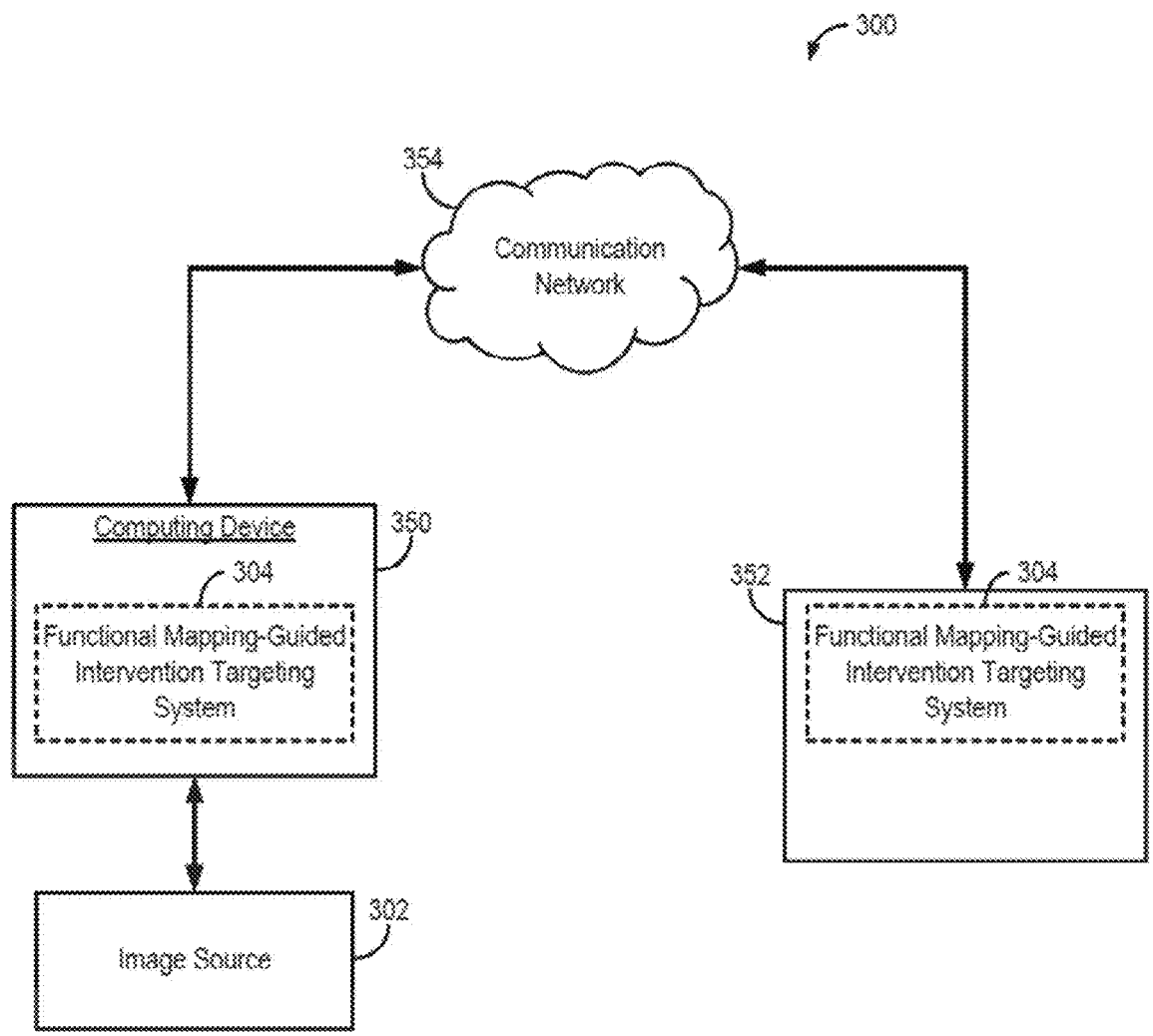
FIG. 3A is a block diagram of an example of a functional mapping-guided intervention targeting system.

Referring now to FIG. 3A, an example of a system 300 for functional mapping-guided intervention targeting (e.g., determination of anatomical targets for brain stimulation) in accordance with some embodiments of the systems and methods described in the present disclosure is shown. As shown in FIG. 3A, a computing device 350 can receive one or more types of data (e.g., fMRI data) from image source 302, which may be an MRI source. In some embodiments, computing device 350 can execute at least a portion of a functional mapping-guided intervention targeting system 304 to generate intervention targets from data received from the image source 302.

Additionally or alternatively, in some embodiments, the computing device 350 can communicate information about data received from the image source 302 to a server 352 over a communication network 354, which can execute at least a portion of the functional mapping-guided intervention targeting system 304. In such embodiments, the server 352 can return information to the computing device 350 (and/or any other suitable computing device) indicative of an output of the functional mapping-guided intervention targeting system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as a magnetic resonance imaging system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Figure 3B:
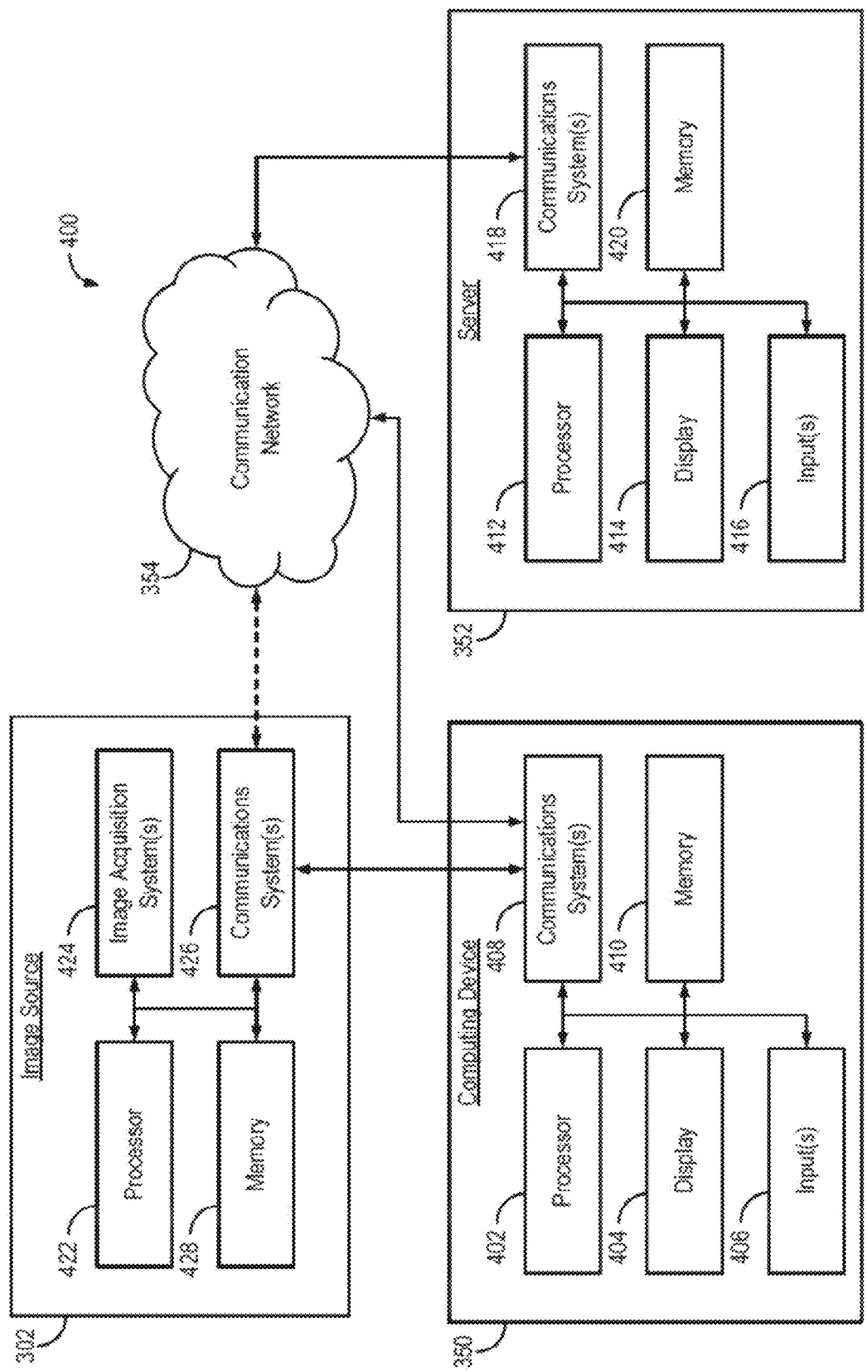
FIG. 3B is a block diagram of components that can implement the functional mapping-guided intervention targeting system of FIG. 3A

Referring now to FIG. 3B, an example of hardware 400 that can be used to implement image source 302, computing device 350, and server 352 in accordance with some embodiments of the systems and methods described in the present disclosure is shown. As shown in FIG. 3B, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include an ultrasound imaging system. Additionally or alternatively, in some embodiments, one or more image acquisition systems 424 can include any suitable hardware, firmware, and/or software for coupling to and/or controlling operations of an ultrasound imaging system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

NON-LIMITING EXAMPLES

Figure 4:
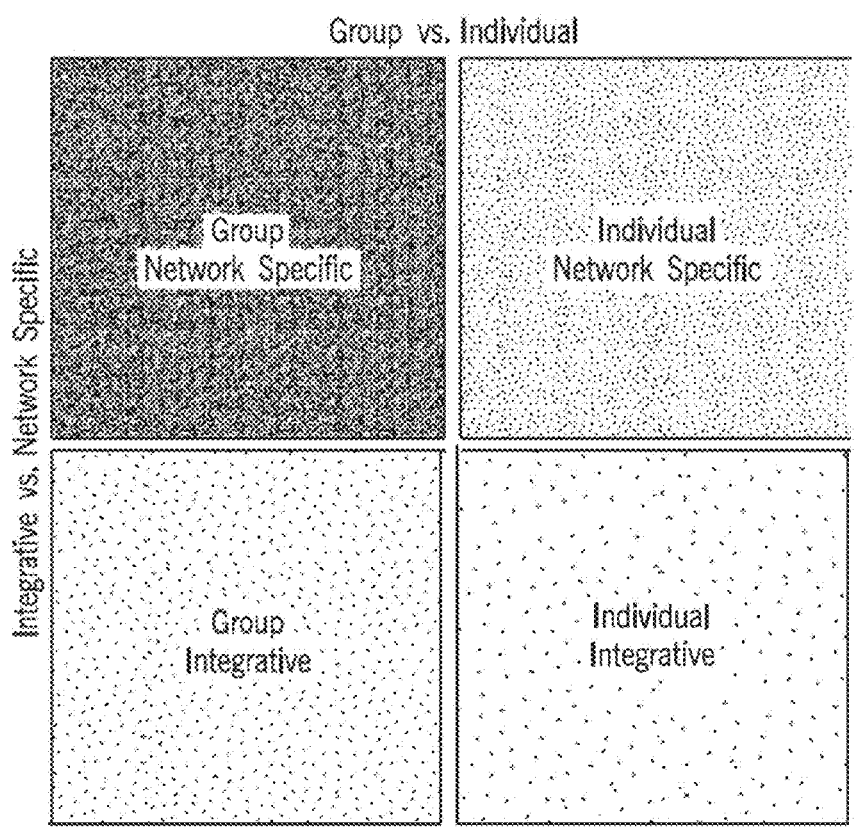
FIG. 4 is an illustration of a framework for subcortical functional organization.

Non-Limiting Example 1: Integrative and Network-Specific Connectivity of the Basal Ganglia and Thalamus Defined in Individuals FIG. 4 is an illustration of a non-limiting framework for subcortical functional organization. Subcortical resting state functional connectivity (RSFC) was characterized along two principal axes, each with two levels (Group vs. Individual; Network specific vs. Integrative). "Group" refers to RSFC that is common across subjects, whereas "Individual" refers to RSFC that is individually specific. "Network specific" refers to regions of the subcortex with preferential RSFC to a single cortical network, whereas "Integrative" refers to regions of the subcortex with preferential RSFC to multiple cortical networks.

To measure cortico-subcortical RSFC in ten individuals from the Midnight Scan Club (MSC) dataset, BOLD activity timecourses were extracted from each voxel in the basal ganglia and thalamus. Cortical time series were averaged across all vertices in each of nine canonical functional networks, defined for each individual as visual, somatomotor hand, somatomotor face, cingulo-opercular, frontoparietal, dorsal attention, ventral attention, salience, and default-mode. A subcortical voxel-to-cortical network connectivity matrix was generated for each subject by computing the Pearson correlation between the timecourses (concatenated across sessions) of each subcortical voxel and each cortical network. These connectivity matrices were used for the subsequent analyses. Given the small size of subcortical structures, additional high spatial resolution BOLD data (2.6 mm isotropic voxels) were collected from one of the individuals to validate results. Two properties of cortico-subcortical RSFC were focused on: (1) Network specificity (preferential connectivity with a single network) vs. Integration (strong connectivity with multiple networks) and (2) Group (common organization across individuals) vs. Individual (variable across individuals) (see FIG. 4).

Larger Amounts of Data In Subcortex Than Cortex for RSFC Reliability

Figure 5A:
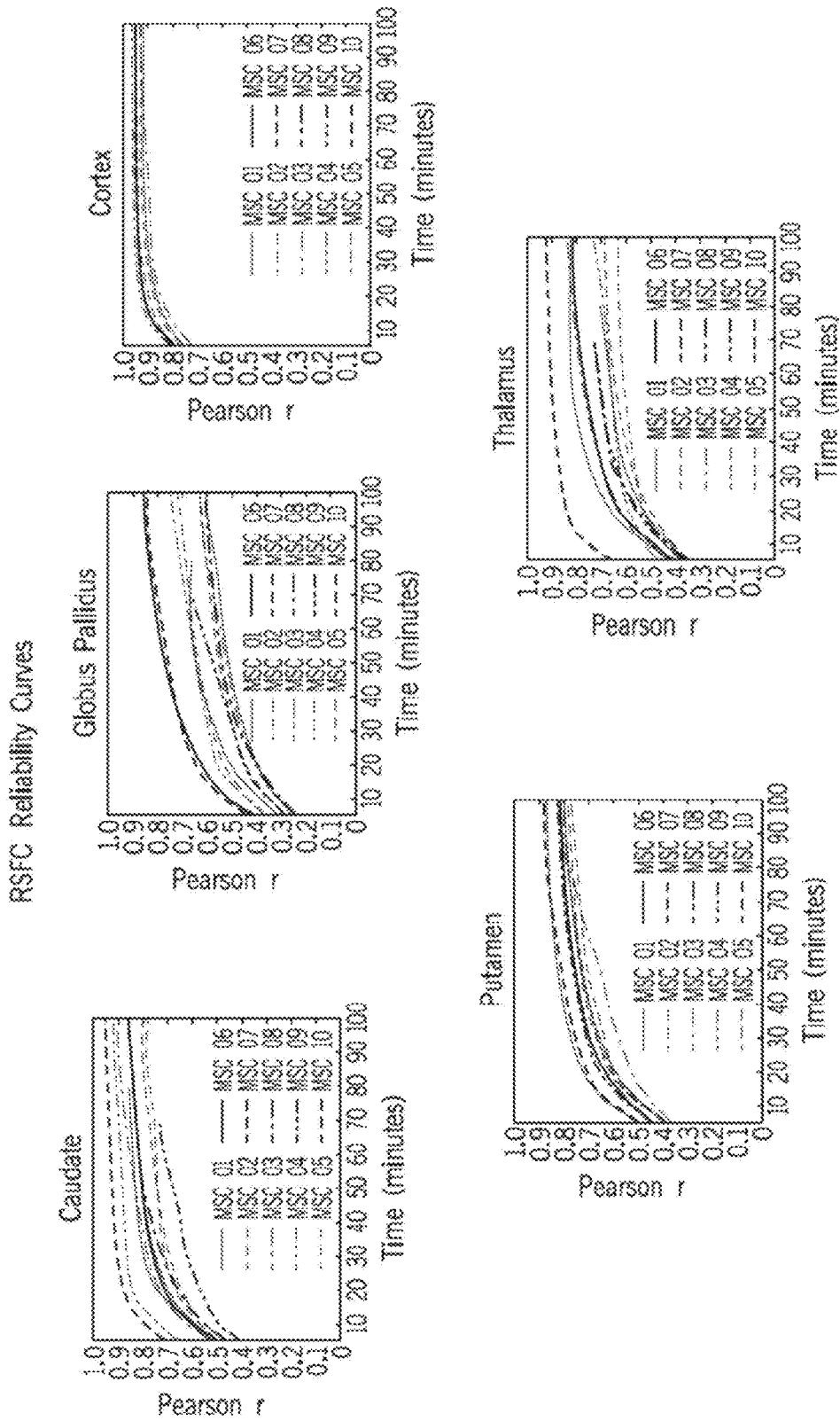
FIG. 5A shows reliability curves of resting state functional connectivity (RSFC)
Figure 5B:
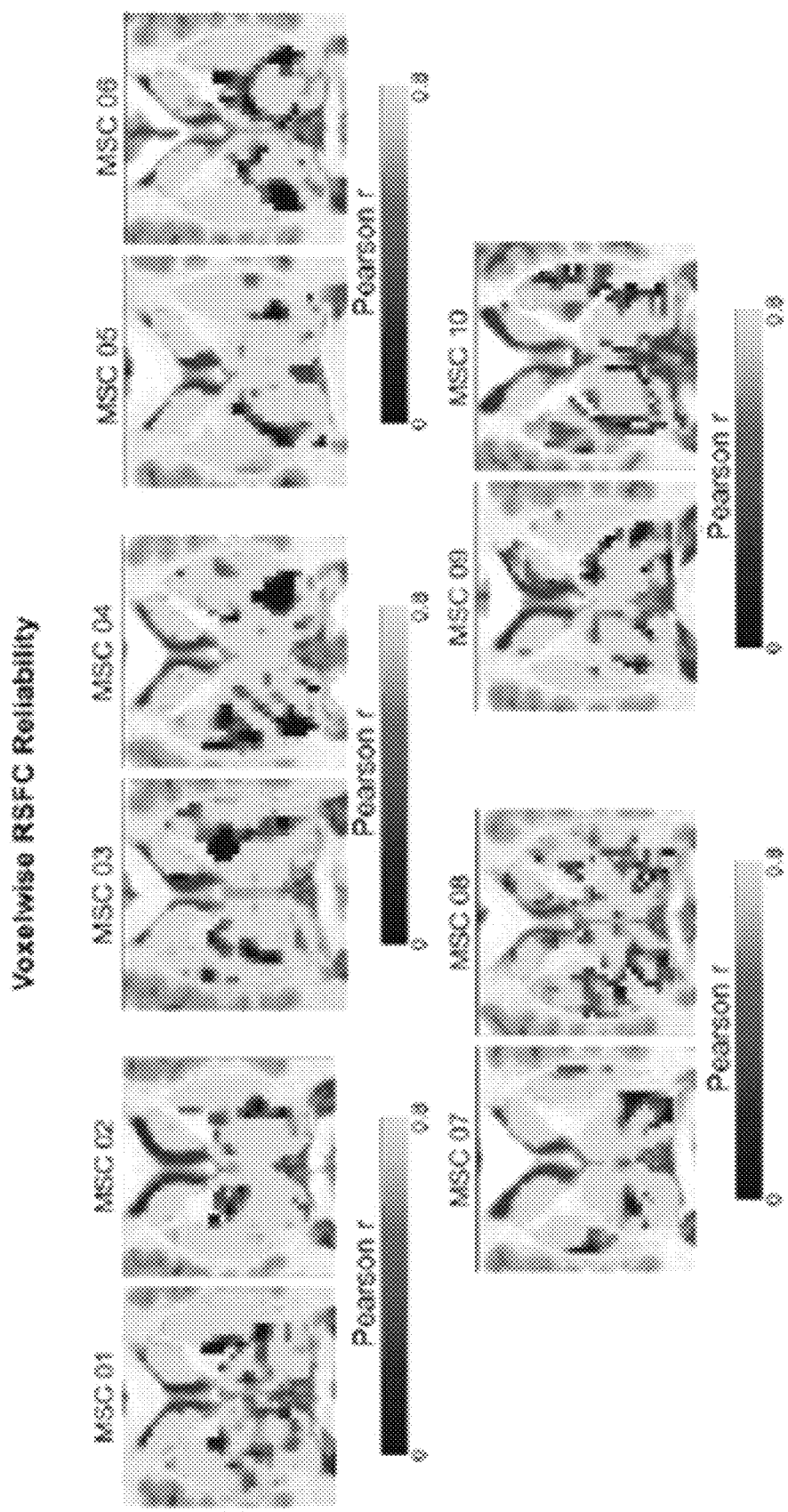
FIG. 5B shows maps of RSFC reliability for all subjects.

FIGS. 5A and 5B show that individual-specific cortico-subcortical correlations are reliable with large amounts of data. Unless otherwise specified, in the drawings of this disclosure, anatomical left is image left in axial images. An iterative split-data reliability analysis was implemented on the subcortical voxel-to-cortical network connectivity matrix for each subject and for each subcortical structure (caudate, putamen, pallidum, and thalamus), as well as on a cortical vertex-to-cortical network connectivity matrix for each subject as comparison. Reliability reached at least 0.6 (Pearson r) for all subjects for all structures with 100 minutes of motion-censored data, with highest reliability in the caudate (FIG. 5A). More specifically, with >100 minutes of data, 87% of voxels in the caudate, 74% in the putamen, 54% in the globus pallidus, and 63% in the thalamus had high reliability (r>0.70) (FIGS. 5A and 5B). The slopes of the curves in FIG. 5A do not plateau at 100 minutes, indicating that improved reliability may be achieved with even more low-movement data. Standard amounts of fMRI data (e.g., 10 minutes) had poor reliability for estimating cortico-subcortical RSFC within an individual. Spatial profile of reliability across voxels was assessed by conducting split-half reliability analyses for each subcortical voxel. In the caudate, reliability was high (>0.8) in most voxels in all subjects with very few voxels (<10% in every subject) having relatively poor reliability (<0.5). In the putamen, pallidum, and thalamus, most voxels had reliability>0.7 for most subjects. All subsequent analyses excluded voxels with reliability<0.5 for each subject, which included 14% of voxels on average across subjects (range 6-25%). When these low reliability voxels were included in analyses of integration vs. network-specificity, on average, 45% of them were integrative and 55% were network-specific.

Low reliability in certain voxels was likely driven by the low temporal signal-to-noise ratio (tSNR) in these regions, as correlations between reliability and tSNR were significant for all subjects (mean r=0.20, all p's<0.001). These results indicate that more data is needed to achieve high reliability for cortico-subcortical RSFC than for cortico-cortical RSFC (45 minutes), and cortico-cerebellar RSFC (90 minutes).

Subcortical RSFC Is Measurable At the Individual Level

Figure 6A:
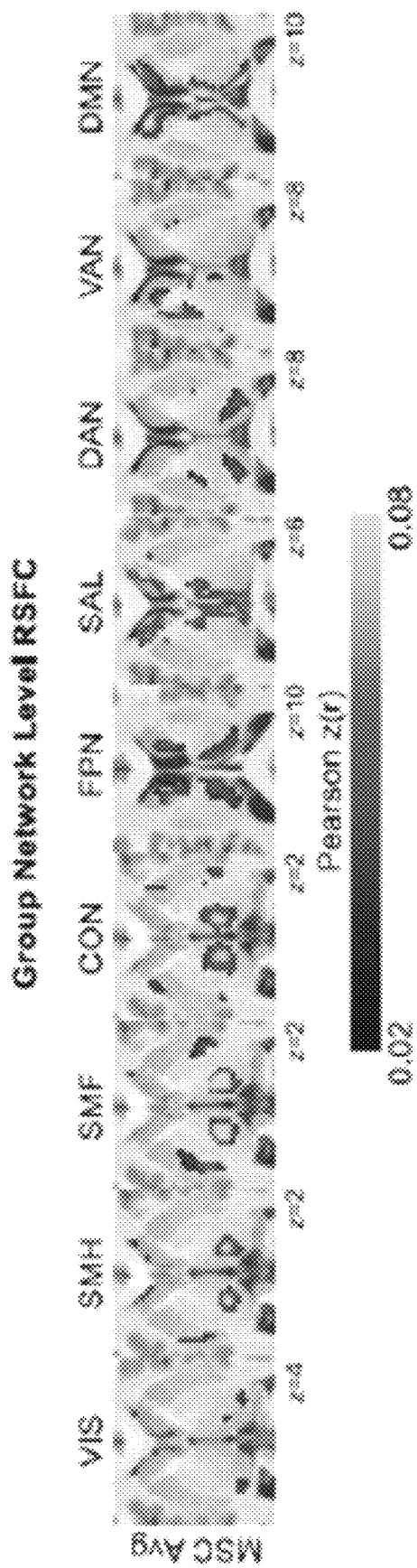
FIG. 6A shows maps of RSFC at a group network level.
Figure 6B:
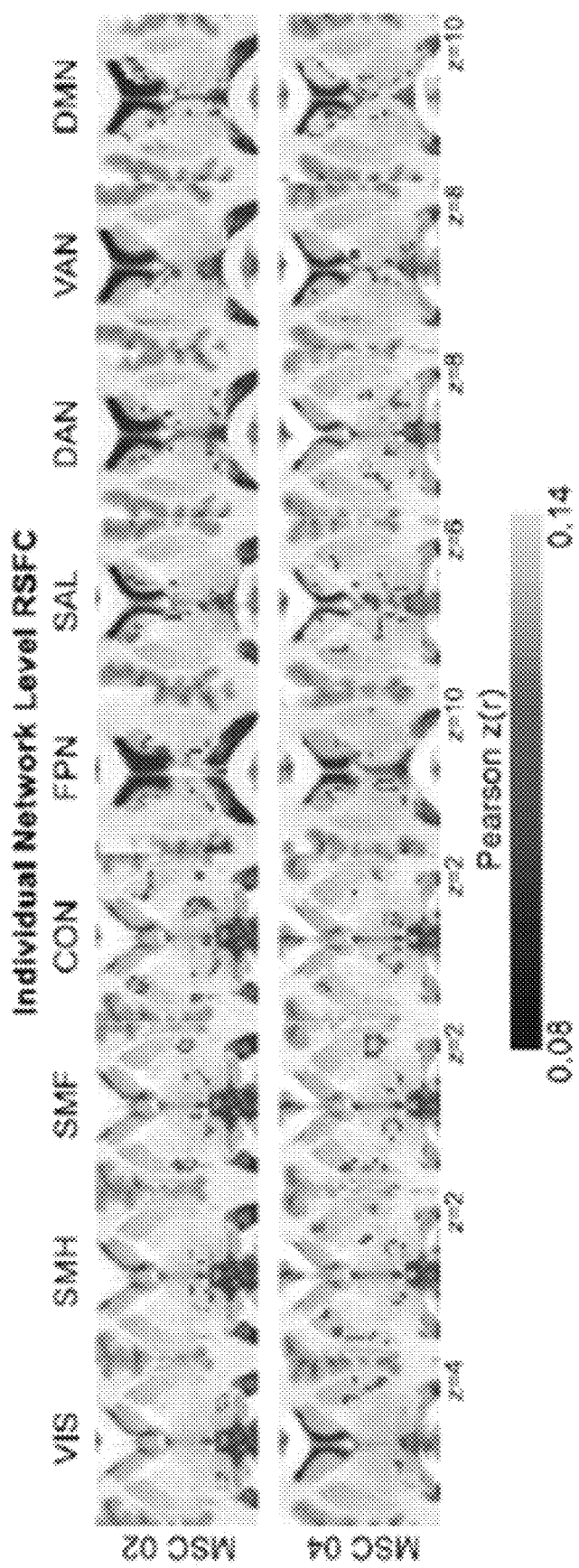
FIG. 6B shows maps of RSFC at the individual network level for two representative subjects.

FIGS. 6A-9 show that subcortical RSFC is measurable at the individual level. FIG. 6A shows group-averaged subcortical RSFC for each cortical network. FIG. 6B shows individual-level subcortical RSFC for each network from two representative MSC subjects, one male (MSC02) and one female (MSC04) (see FIG. 7 for all ten subjects shown later). FIG. 6C demonstrates subject overlap, where the number of subjects with strong (top 10%) correlations with each network at that voxel is shown. FIG. 6D shows concordance between RSFC and task activations/deactivations for individuals. For example, task-evoked increases in BOLD activity during a motor task converge with peak RSFC in the somatomotor hand network. Task-evoked deactivations during a set of cognitive/perceptual tasks converge with peak RSFC in the default-mode network. In FIG. 6D, VIS stands for visual, SMH for somatomotor hand, SMF for somatomotor face, CON for cingulo-opercular network, FPN for frontoparietal network, SAL for salience, DAN for dorsal attention network, VAN for ventral attention network, DMN for default-mode network.

Figure 7:
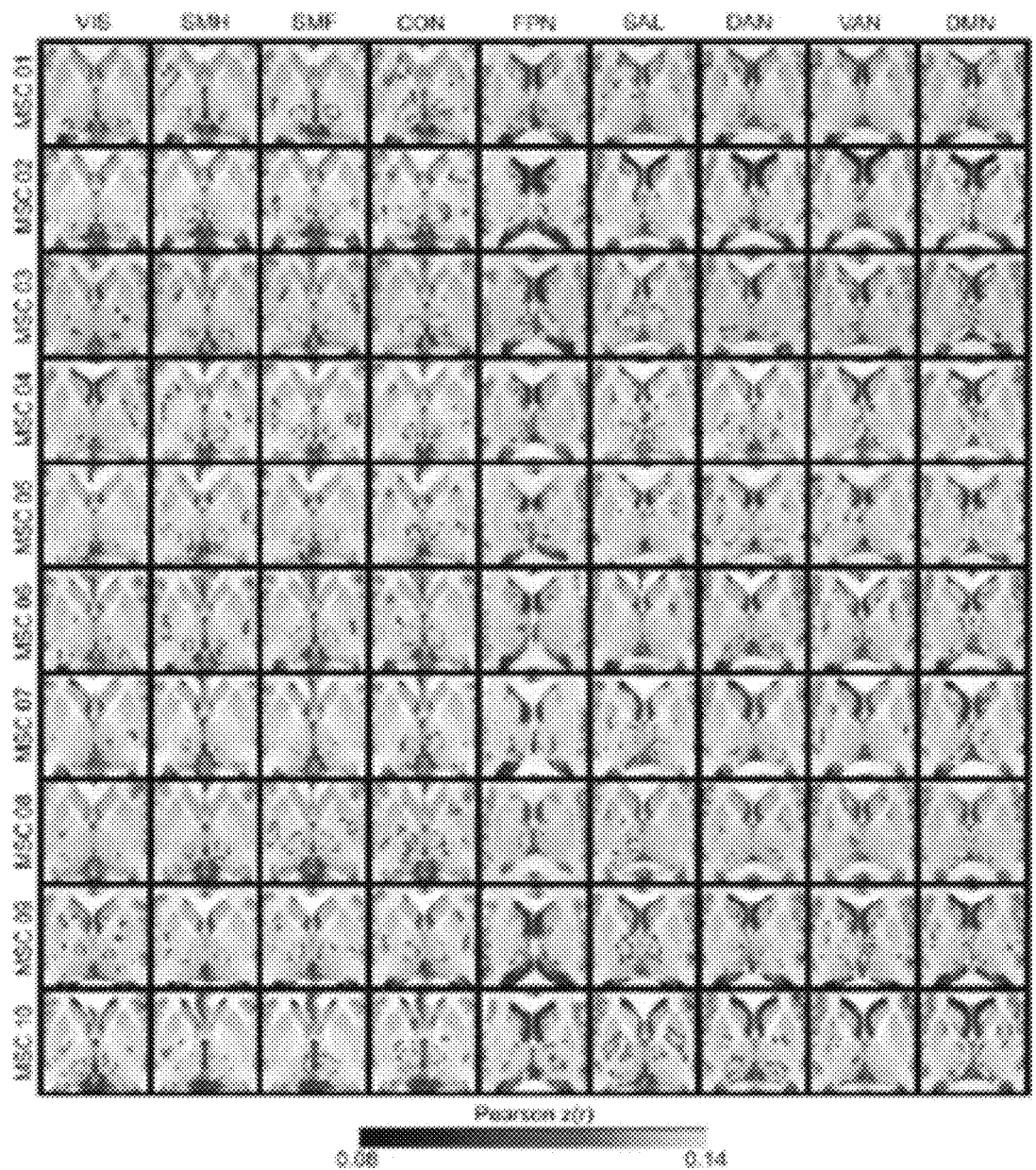
FIG. 7 shows maps of FC with each network for all subjects.

FIG. 7 shows individual-specific cortico-subcortical RSFC for each network for all subjects. For each subject, correlations between subcortical voxels and each cortical network are shown.

Figure 8A:
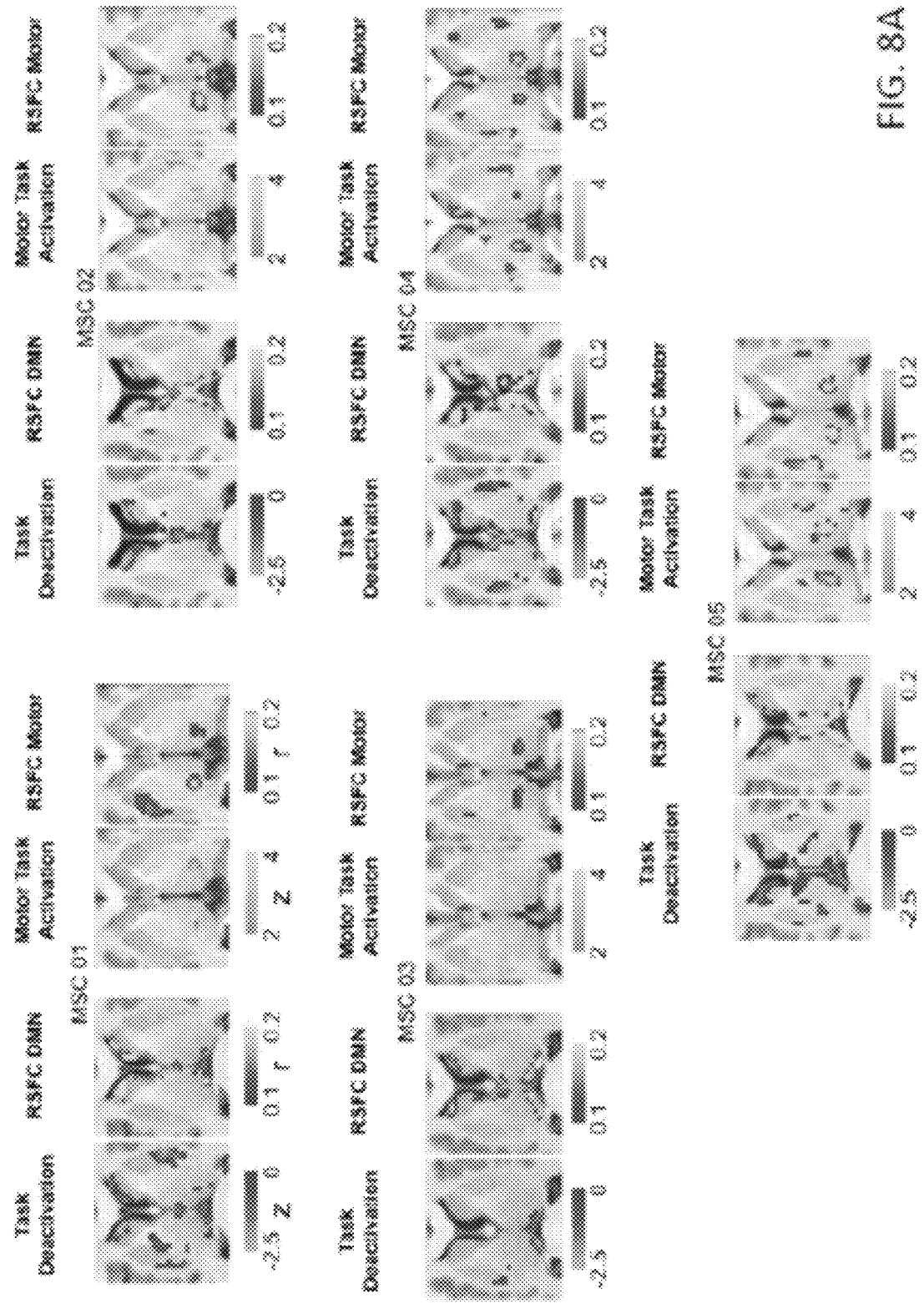
FIG. 8A shows maps illustrating overlap of task activation/deactivation and FC for five of the subjects in FIG. 7.
Figure 8B:
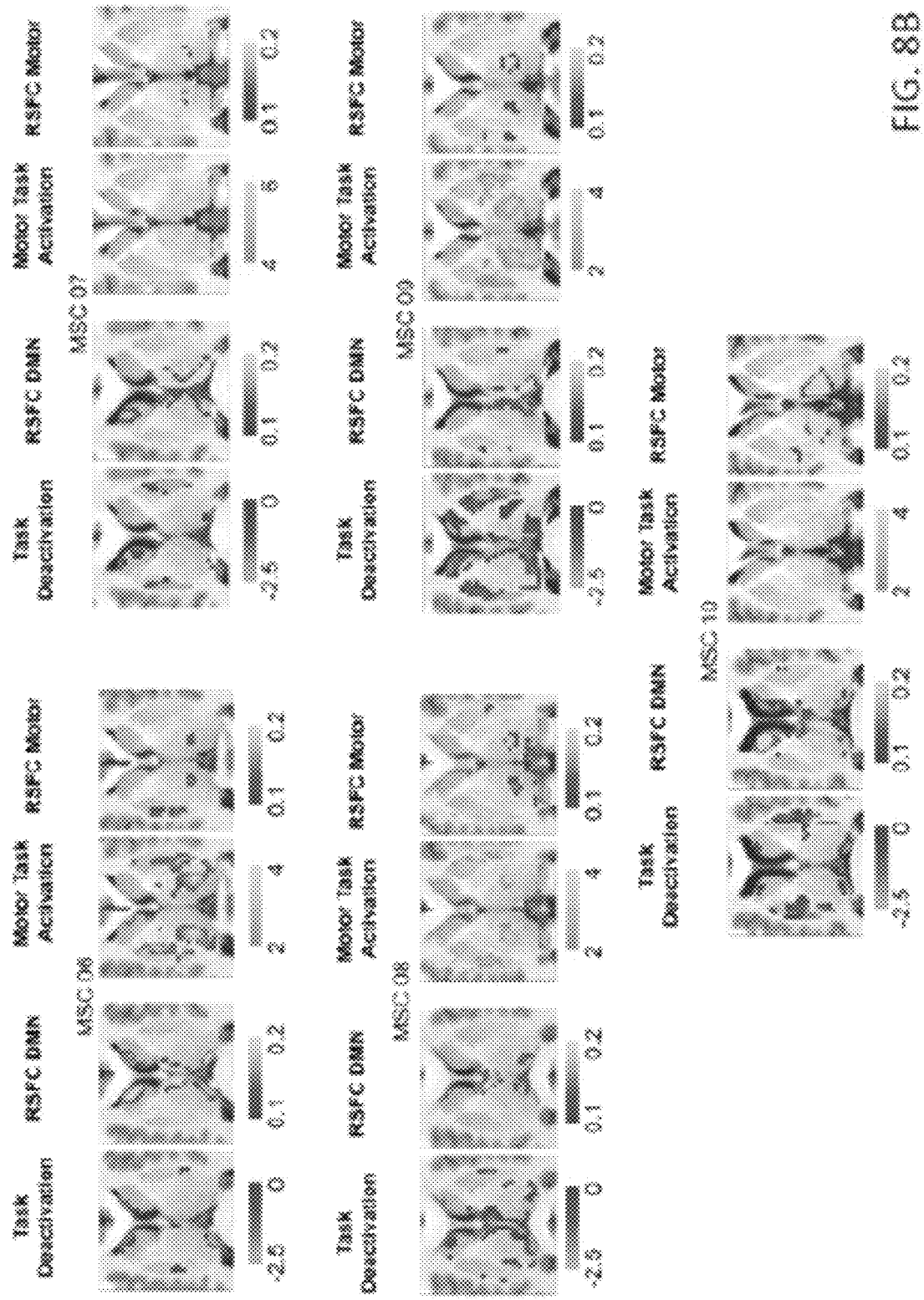
FIG. 8B shows maps illustrating overlap of task activation/deactivation and FC for the remaining five subjects in FIG. 7.

FIGS. 8A and 8B show task/rest overlap for all subjects, where concordance between RSFC and task activations/deactivations for each individual is evident. Similar to FIG. 6D, task-evoked increased in BOLD activity during a motor task converge with peak resting-state correlations with the somatomotor hand network. Task-evoked deactivations during a set of cognitive/perceptual tasks converge with peak resting-state correlations with the default-mode network.

Figure 9:
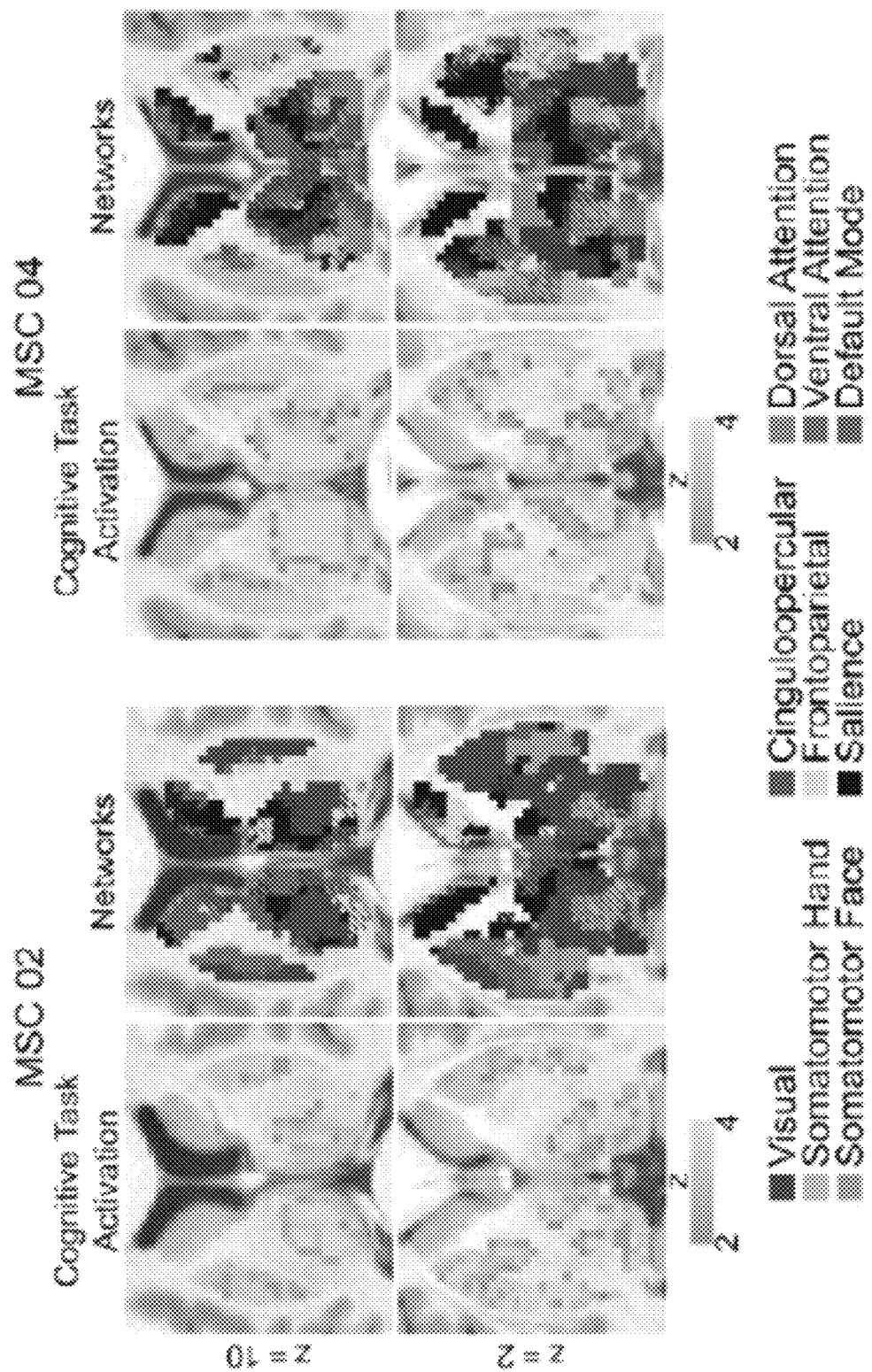
FIG. 9 shows maps illustrating task activations overlapped with FC.

FIG. 9 shows task activations during the cognitive/perceptual tasks overlapped with multiple cognitive control networks. Task activations (left panels) are shown for two example subjects next to the modified winner-take-all maps (right panels) for side-by-side comparison.

To determine the robustness of the spatial patterns of these correlations, the observed spatial patterns of correlations were compared to those generated from a null distribution from rotated networks on the cortex. Spearman's rho (y) between the actual correlations and percent stronger than null across all networks and subjects was 0.79±0.07.

Figure 6C:
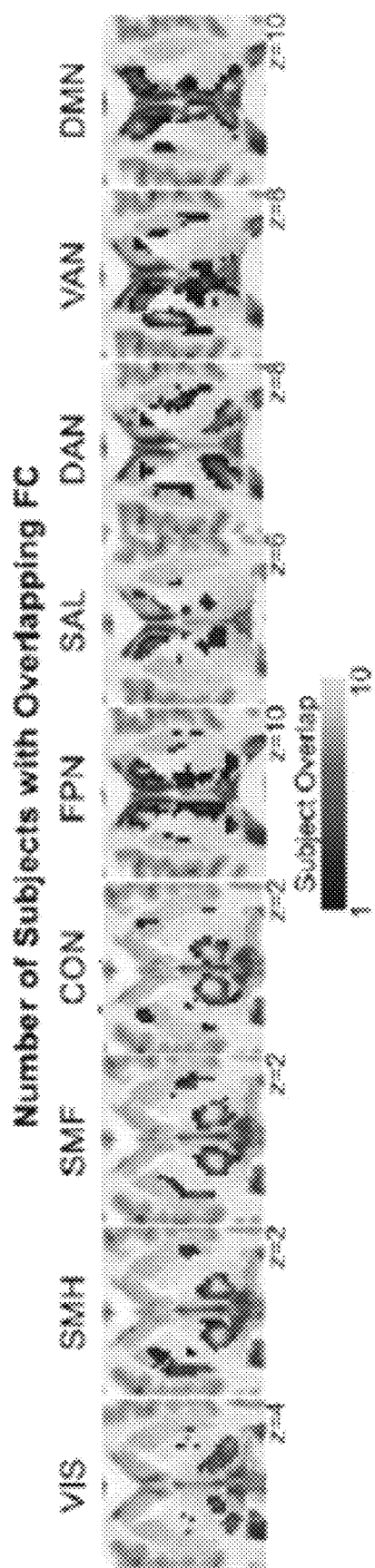
FIG. 6C shows maps illustrating number of subjects with overlapping functional connectivity (FC)

Across subjects, there was similarity across subjects in subcortical RSFC for each network (see FIG. 6C). The default-mode network was strongly functionally connected to the medial thalamus and large portions of the caudate extending into the ventral striatum. The visual and dorsal attention networks exhibited strong connectivity with the lateral and posterior regions of the thalamus corresponding to the location of the pulvinar and possibly the lateral geniculate nucleus. The frontoparietal and salience networks were functionally connected to the caudate (head, body). The ventral attention network was connected to the caudate, medial putamen, and medial thalamus, with stronger correlations in the left hemisphere. The cingulo-opercular network exhibited strong connectivity with a large portion of the ventral thalamus and distinct anterior and posterior parts of putamen. Connectivity with the somatomotor networks was observed in the ventral and lateral portions of the thalamus, likely corresponding to ventral lateral and ventral posterior nuclei, with the somatomotor hand network peak correlations shifted posterior to that of the somatomotor face network (consistent with known somatotopy), although there was substantial overlap. In addition to these commonalities, variability across individuals was also evident (see FIG. 7). For example, strong connectivity is shown with the dorsal attention network in the caudate in MSC02, but not in MSC04 (also see FIG. 6B).

Figure 6D:
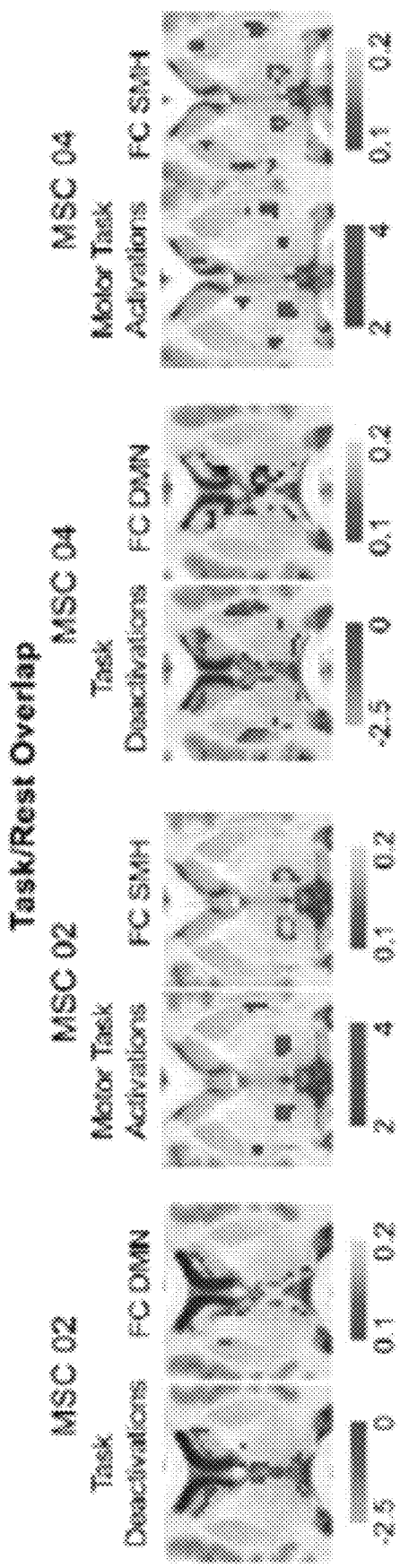
FIG. 6D shows maps illustrating overlap of task activation/deactivation with FC.
Figure 10A:
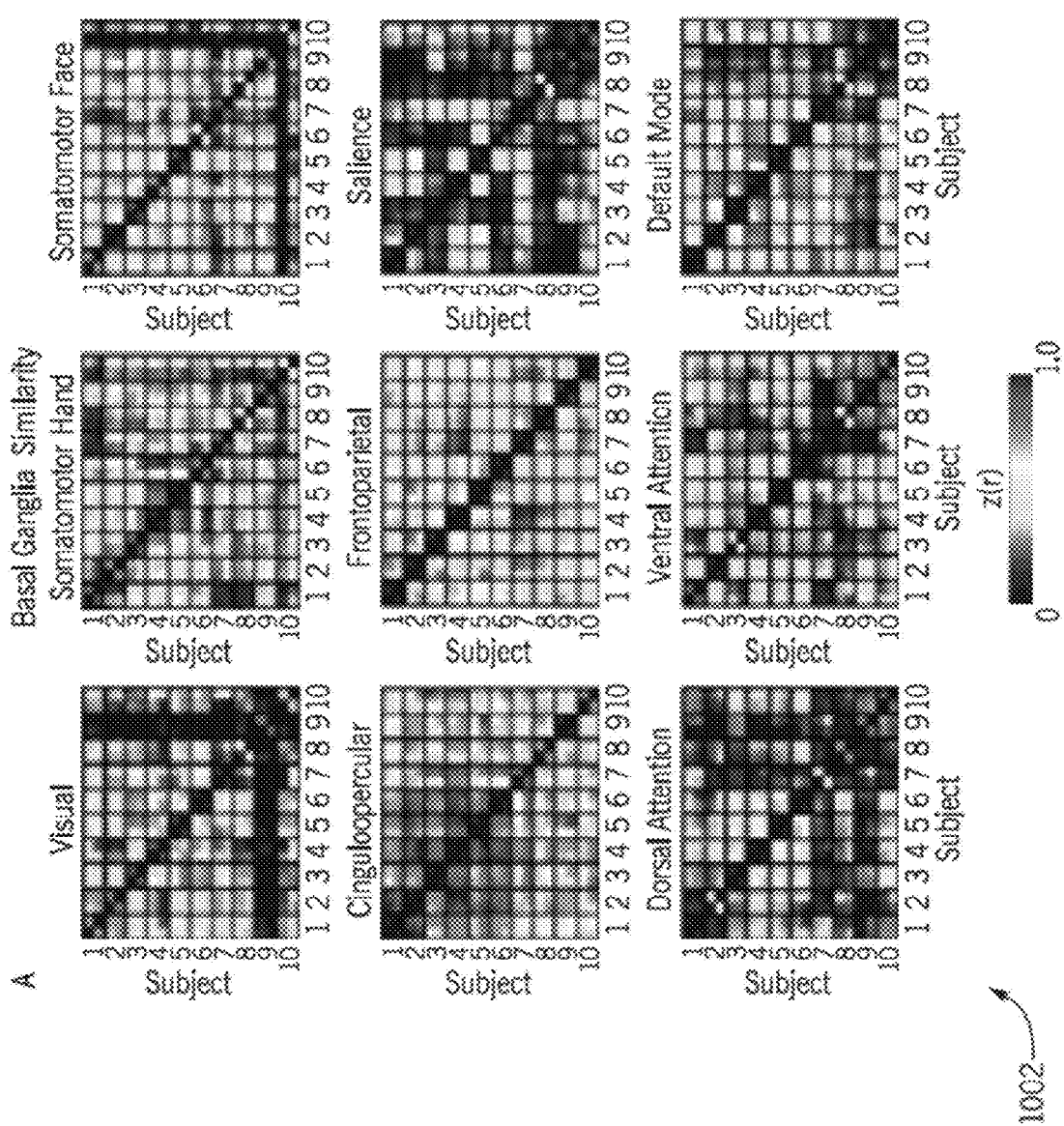
FIG. 10A shows network similarity matrices for the basal ganglia and the thalamus.
Figure 10A:
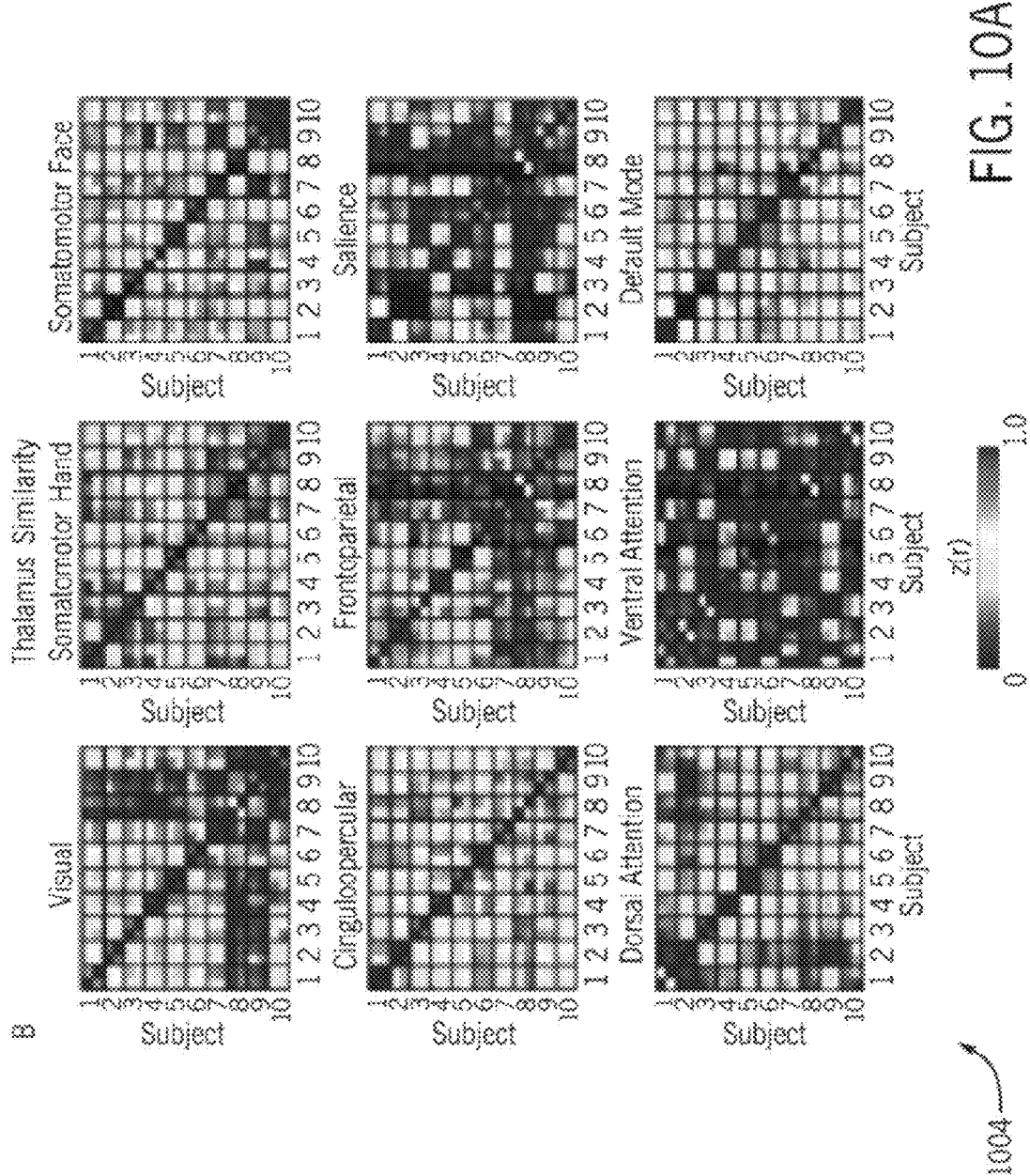
Figure 10B:
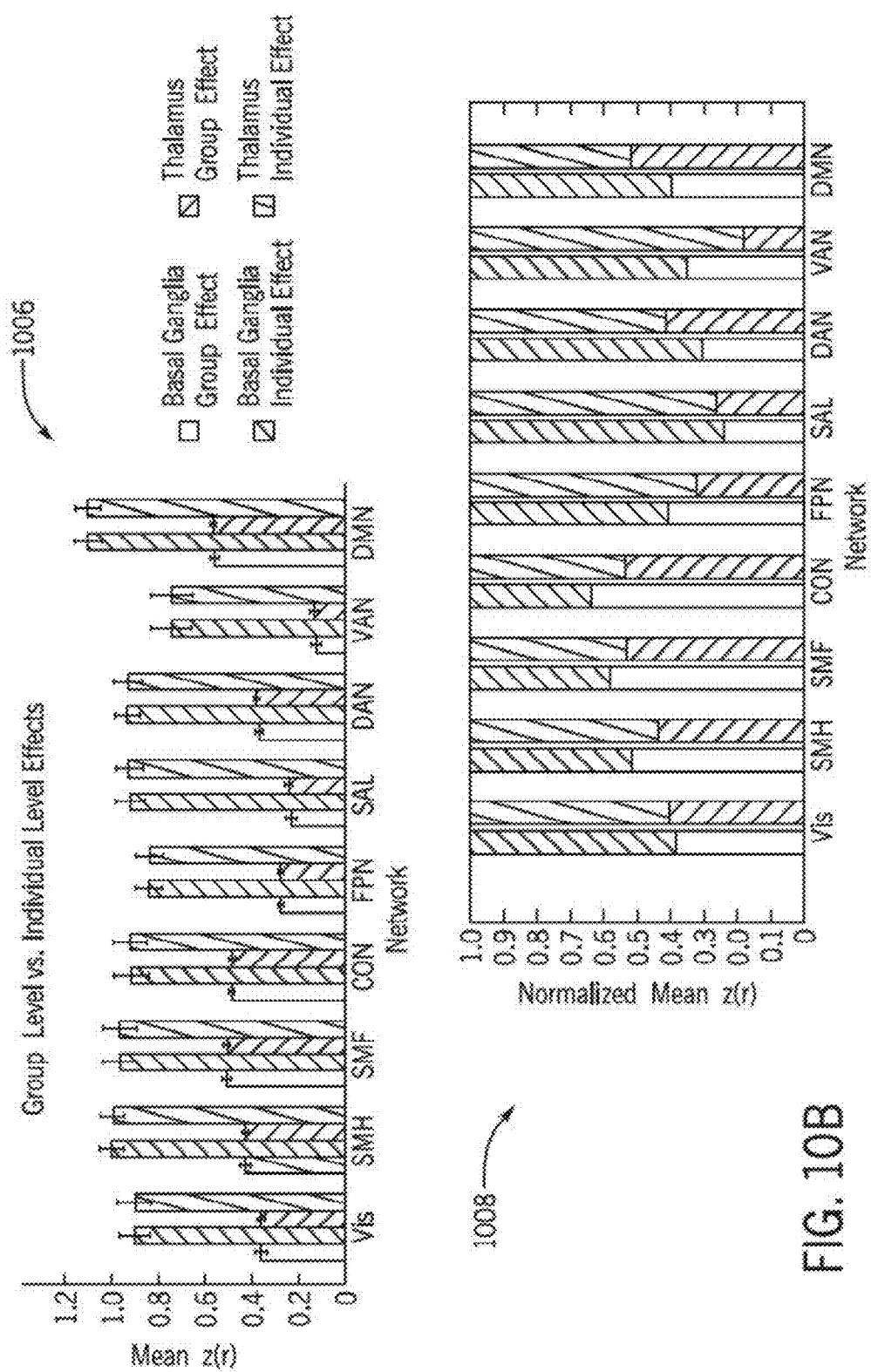
FIG. 10B is a comparison between group level and individual level effects.

The spatial pattern of correlations was compared to task fMRI responses elicited in the same individuals (see FIG. 6D and FIGS. 8A-8B). Task activations/deactivations validated the RSFC mapping of functional networks in the subcortex. Deactivations during a set of cognitive/perceptual tasks overlapped well with default-mode network connectivity in the head of the caudate and medial thalamus. Activations during these cognitive/perceptual tasks in the subcortex overlapped multiple control networks (e.g., cingulo-opercular, frontoparietal, ventral attention, dorsal attention, salience), sparing the default mode network (see FIG. 9). In addition, activations in the subcortex in response to hand movements during a motor task (hand >foot contrast) overlapped well with positive correlations with the somatomotor hand network. Individual-Specific and Group Level Features of Subcortical RSFC Given that subcortical correlations show individual-specific features (see FIGS. 6B and 7) and consistency across subjects (see FIG. 6C), the extent to which functional networks exhibited group vs. individual-specific features was quantified, using a similarity analysis (FIGS. 10A and 10B). For each subject, the RSFC data were randomly split in half, and the spatial similarity (Pearson r) of subcortical-cortical correlations with each network was calculated within each subject and between all subjects. To quantify variance in RSFC data shared across individuals (group effect) vs. variance unique to individuals (individual effect), the within individual similarities (on-diagonal elements; individual effect) was compared to the between individual similarities (off-diagonal elements; group effect), and normalized by the sum of the group and individual effects.

FIGS. 10A and 10B show results of subcortical network similarity analyses. Network similarity matrices 1002, 1004 for the basal ganglia and for the thalamus, respectively, are shown in FIG. 10A. The matrices are organized first by individual and then by split-half sessions (each half represents data from 5 sessions). In FIG. 10A, off-diagonal elements represent group effects, whereas on-diagonal elements represent individual effects. Quantification of group versus individual effects for RSFC between the basal ganglia and cerebral cortex and between the thalamus and cerebral cortex is shown in plots 1006, 1008 in FIG. 10B. In the plot 1006, error bars denote standard error of the mean across subjects. In the plot 1008, the effects are plotted as a proportion of the total effects to contrast the relative magnitudes of group and individual effects.

This analysis was conducted separately for the basal ganglia and thalamus, and demonstrated large group contributions (basal ganglia=42% shared RSFC variance across subjects; thalamus=39%) and individual contributions (basal ganglia=58% RSFC variance specific to individuals; thalamus=61%) (see FIGS. 10A and 10B). Some control networks (frontoparietal, salience, dorsal attention, ventral attention) showed significantly less similarity across the group (i.e., more individual variability) than the somatomotor networks and the cingulo-opercular network ($\Delta z=-0.43$, $t=-25.15$, $p<0.001$). Thus, the cingulo-opercular network stands in contrast to other control networks, demonstrating greater similarity to somatomotor networks in the subcortex. An alternative analysis strategy of comparing the standard deviation of the cortico-subcortical correlations between higher-order functional networks (FPN, DAN, VAN, SAL, CON, DMN) and processing networks (VIS, SMH, SMF) confirmed greater variability in the higher-order networks than the processing networks ($t=13.1$, $p<0.001$), and the individual network profiles paralleled that shown in the quantification.

Localization of Functional Integration Zones in Cortex

FIGS. 11A-14 show functional integration. Characterizations of basal ganglia and thalamic functional organization, using group-averaged data, often implemented a winner-take-all network approach. This winner-take-all approach cannot account for integration of multiple networks within regions of the subcortex, since the functional maps are solely based on the network with the strongest connectivity. In addition, a group-level approach to identify functional integration may be spuriously affected by averaging across-subject variability. That is, the same anatomical location may exhibit connectivity to different networks in different individuals, leading to the appearance of integration when those individual signals are averaged together. Therefore, network co-localization at the individual-level was evaluated in order to increase the accuracy of characterizing the nature of functional integration within the subcortex.

Integration used herein is the exhibition of strong functional connectivity with multiple networks. A modified winner-take-all analysis approach was implemented to account for zones of integration as well as zones that are "network-specific" (one network dominates). For every subcortical voxel, the cortical network with the strongest correlation was identified, as the winning network. Regions of integration vs. network-specificity were identified by testing whether the RSFC with any other network was above a given threshold (66.7%) of the correlation with the winning network. Additional thresholds (50%, 75%) were tested, which yielded similar zones of integration (see FIG. 11A). If the correlations with all the other networks were below this threshold for a given voxel, that voxel was considered "network-specific". If the correlations with any of the other networks were within that threshold for a given voxel, that voxel was considered "integrative", as multiple networks correlated strongly. An alternative approach based on effect size rather than percent differences yielded very similar results (see FIG. 11B). An effect size may be measured with Cohen's d, which indicates standardized difference between two means of two sets of data. A value of 0.2 has a small effect size, 0.5 has a medium effect size, and 0.8 has a large effect size.

Figure 11A:
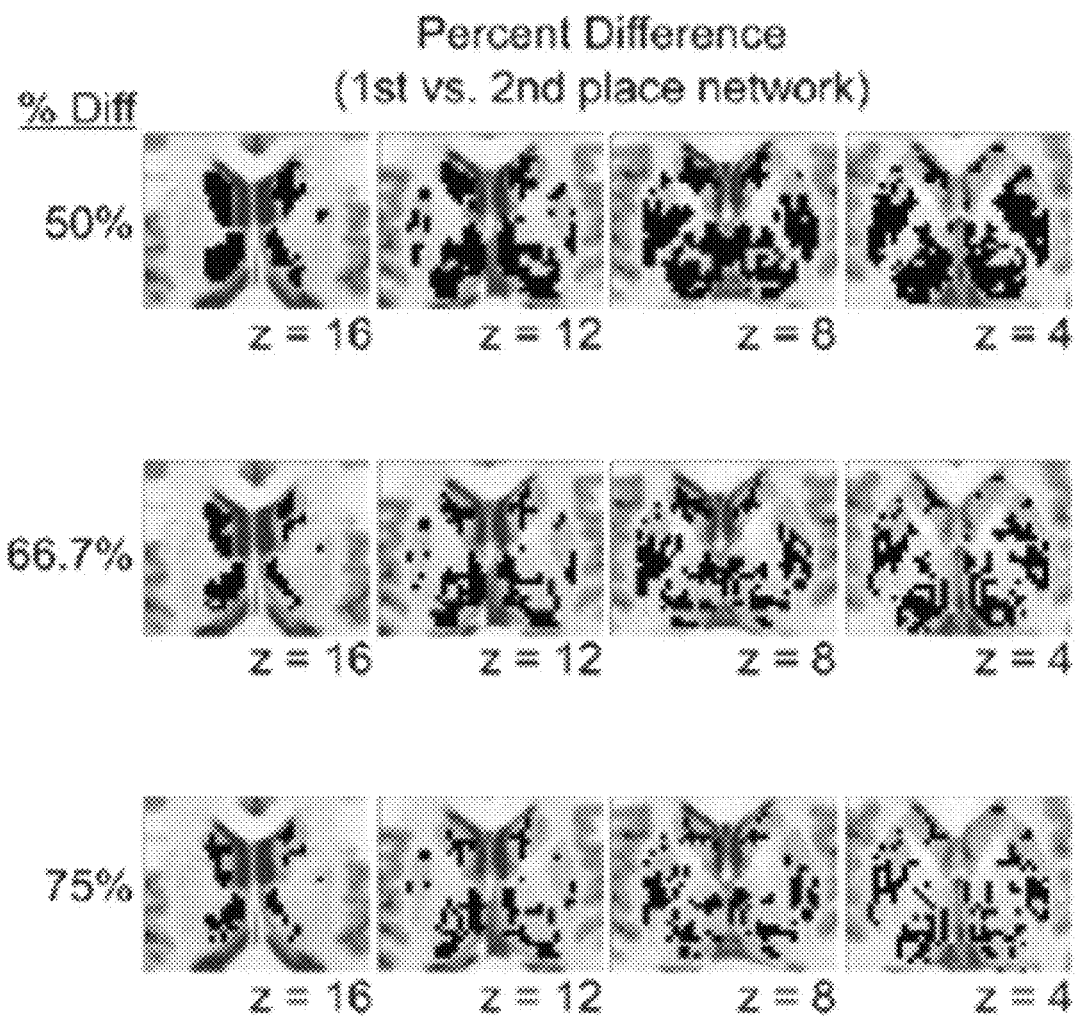
FIG. 11A shows integrative zones determined by an exemplary method.
Figure 11B:
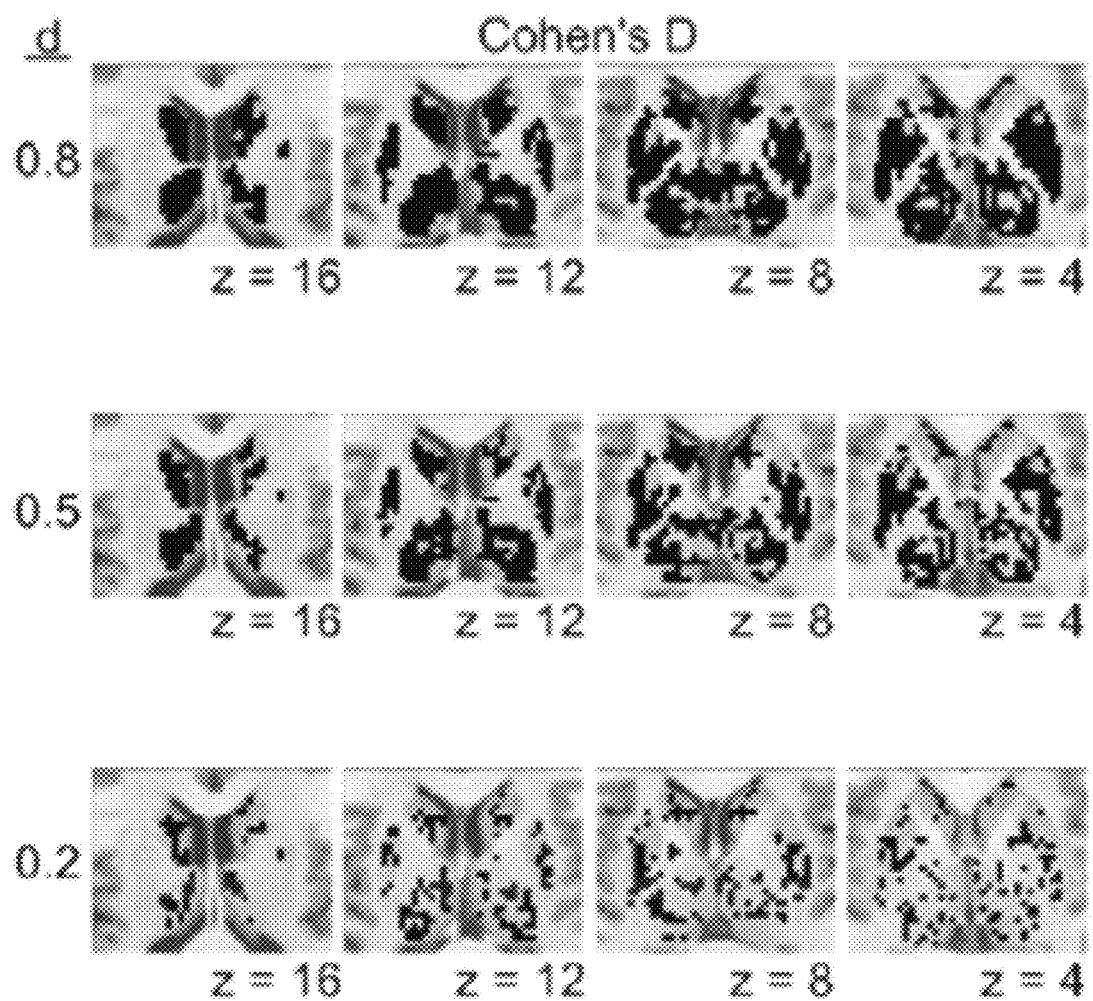
FIG. 11B shows integrative zones determined by another exemplary method.

FIGS. 11A and 11B show integrative zone centers were consistent, regardless of the method used to define a voxel as integrative or the specific threshold. In FIG. 11A, integrative voxels were displayed in black and defined as those in which the correlation with any other network was within a given percent (50%, 66.7%, and 75%) of the "winning" network correlation. In FIG. 11B, the integrative voxels were displayed in black and defined as those in which the effect size between the correlation with the winning network and another network was less than a given effect size (large, d=0.8; medium, d=0.5; small, d=0.2).

Figure 12:
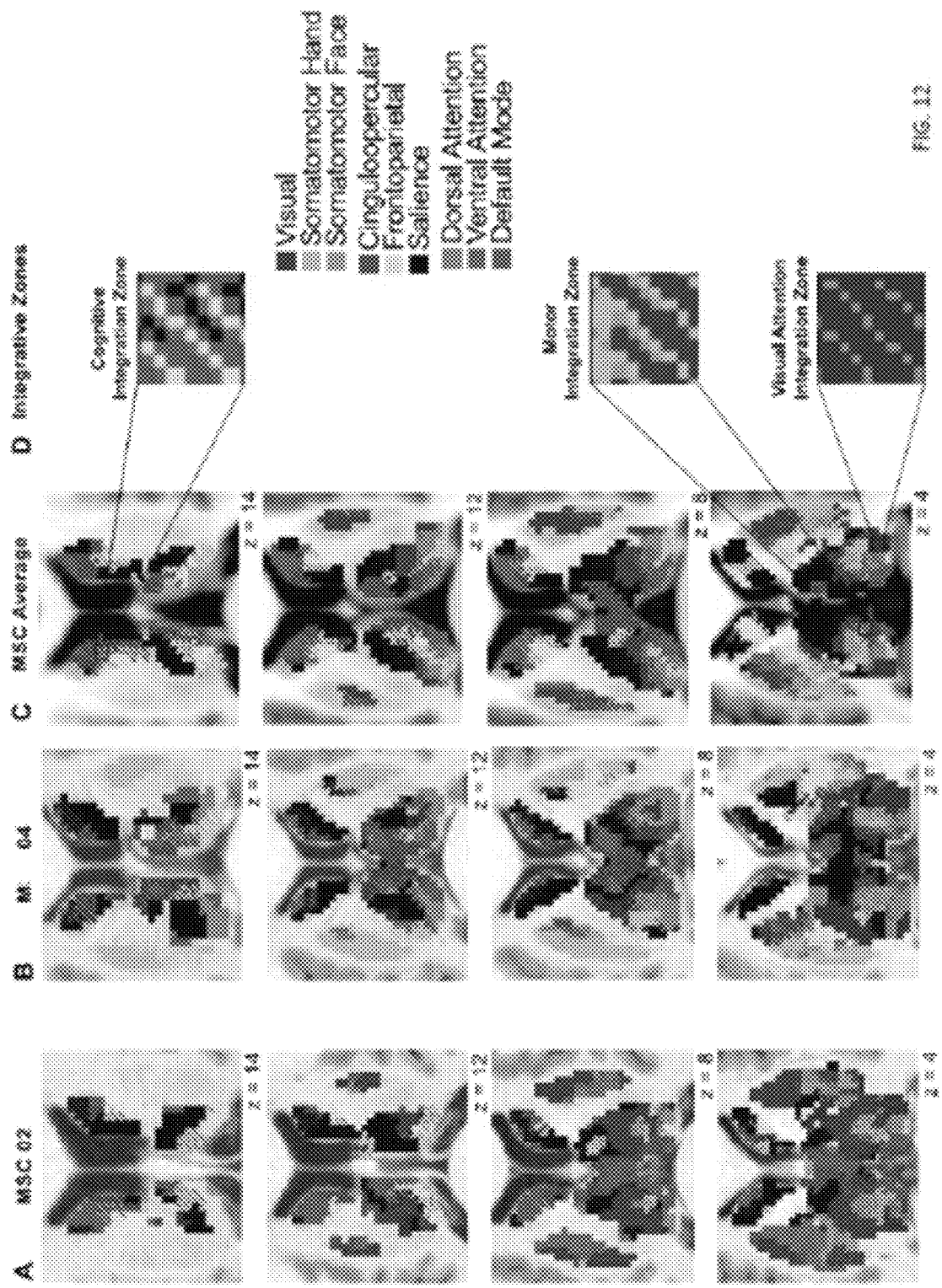
FIG. 12 shows maps of integrative zones.
Figure 13:
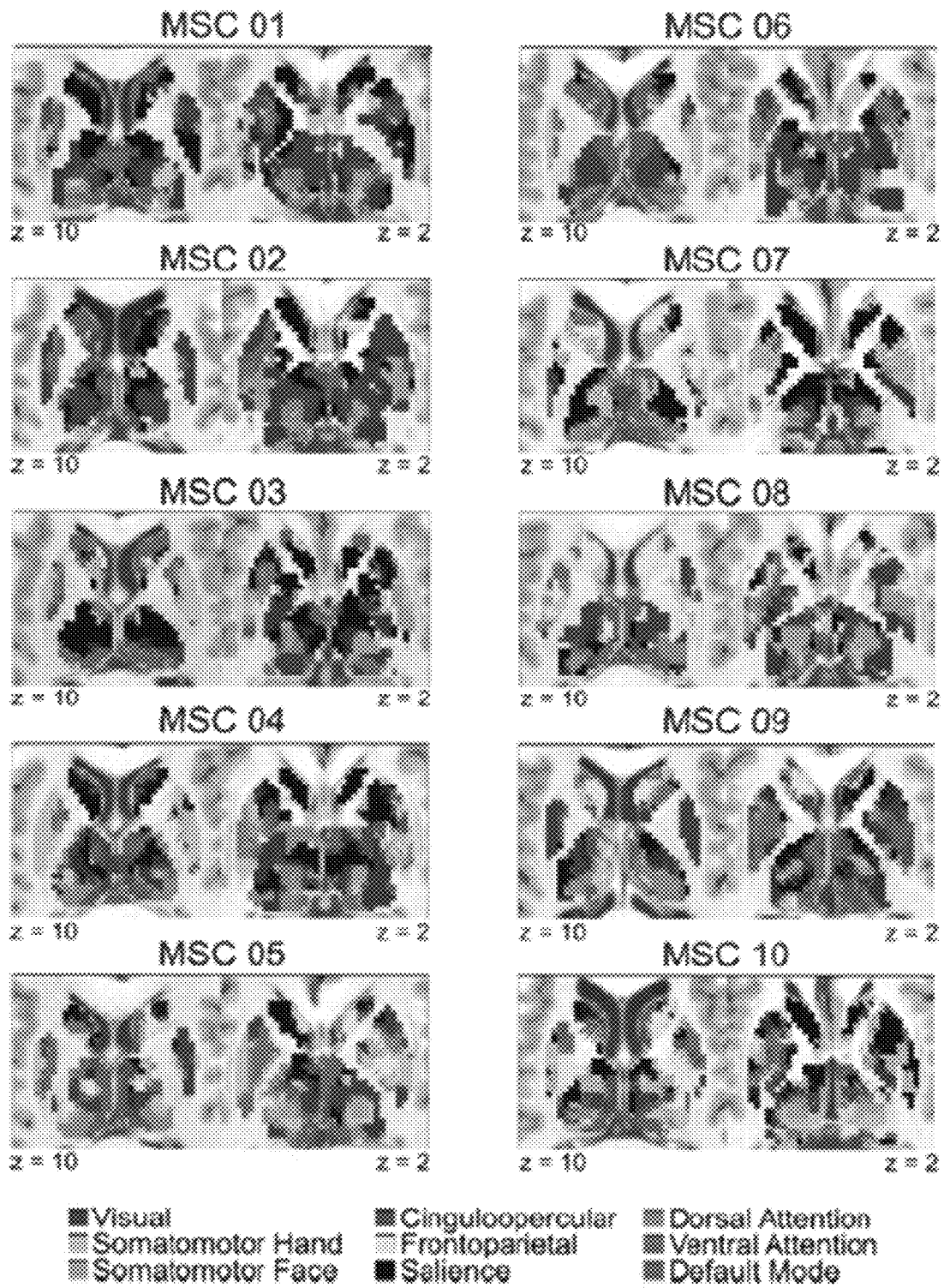
FIG. 13 shows maps of integrative zones for all subjects.

FIG. 12 show network-specific and integrative functional zones in the basal ganglia and thalamus. Data is displayed for one male representative subject (MSC02) in Column A, one female representative subject (MSC04) in Column B, and the group average in Column C. Voxels with preferential RSFC to one network (network-specific) are represented by solid colors, and voxels functionally connected to multiple networks (integrative) are represented by cross-hatching. Column D includes enlarged views of three clusters of integration zones (also see later in FIGS. 16A and 16B), which are cognitive integration zones, motor integration zones, and visual attention integration zones. FIG. 13 shows individual-specific functional organization of the basal ganglia and thalamus of all subjects. Similar to FIG. 12, voxels with preferential RSFC to one network (network-specific) are represented by solid colors, and voxels functionally connected to multiple networks (integrative) are represented by cross-hatching.

From the group average maps alone, one may suspect that the zones of integration may be artifactual due to subject averaging. However, several integration zones were identified within all individuals, and thus, are not simply by-products of group averaging. One of the most notable integration zones was identified in the ventral intermediate thalamus, integrating the cinguloopercular, somatomotor hand, and somatomotor face networks (see FIG. 12B).

Figure 14:
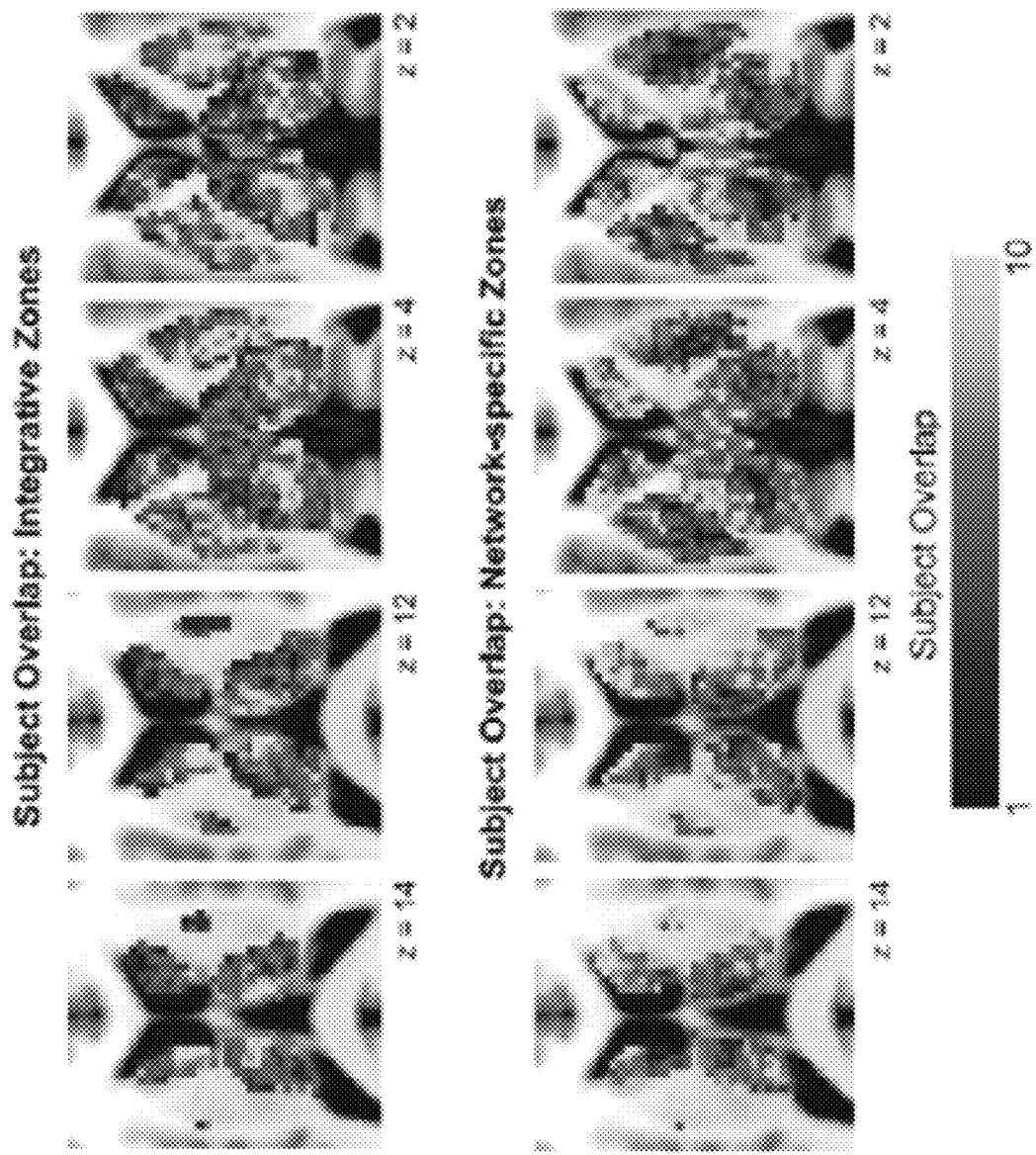
FIG. 14 shows overlap across individuals of integrative and network-specific zones.

These functional network maps suggest that certain zones of integration and network-specificity appear similar across individuals. The overlap of integrative and network-specific voxels were quantified (irrespective of the specific network association) across subjects. FIG. 14 shows overlap across individuals of integrative and network-specific functional zones. Higher values represent voxels with integrative functional zones present in multiple subjects and network-specific functional zones present in multiple subjects. The overlap of integrative voxels demonstrates that certain zones were integrative in most subjects (e.g., ventral intermediate thalamus), and overlap of network-specific voxels demonstrates that certain zones were network-specific in most subjects (e.g., head of the caudate). In addition, certain integrative or network-specific zones represented the same networks across individuals, while others represented different networks across individuals. This individual similarity and variability in network associations are explored in more detail below.

In order to benchmark the degree of integration in the basal ganglia and thalamus compared to the cerebellum and cerebral cortex, the percent of voxels/vertices within each brain structure that were integrative were computed, as defined by the 66.7% threshold used in the analyses above. This computation demonstrated that a greater percentage of the subcortex (45%) was integrative compared to the cerebellum (35%) and cerebral cortex (31%). Within the subcortex, the thalamus was found to be 45% integrative, the globus pallidus was found to be 52% integrative, the putamen was found to be 42% integrative, and the caudate was found to be 37% integrative. The thalamus was more integrative than the caudate, even though the thalamus is 240% larger in size. Therefore, the increased integration in the subcortex is not likely caused by the smaller size of the structures.

Figure 15:
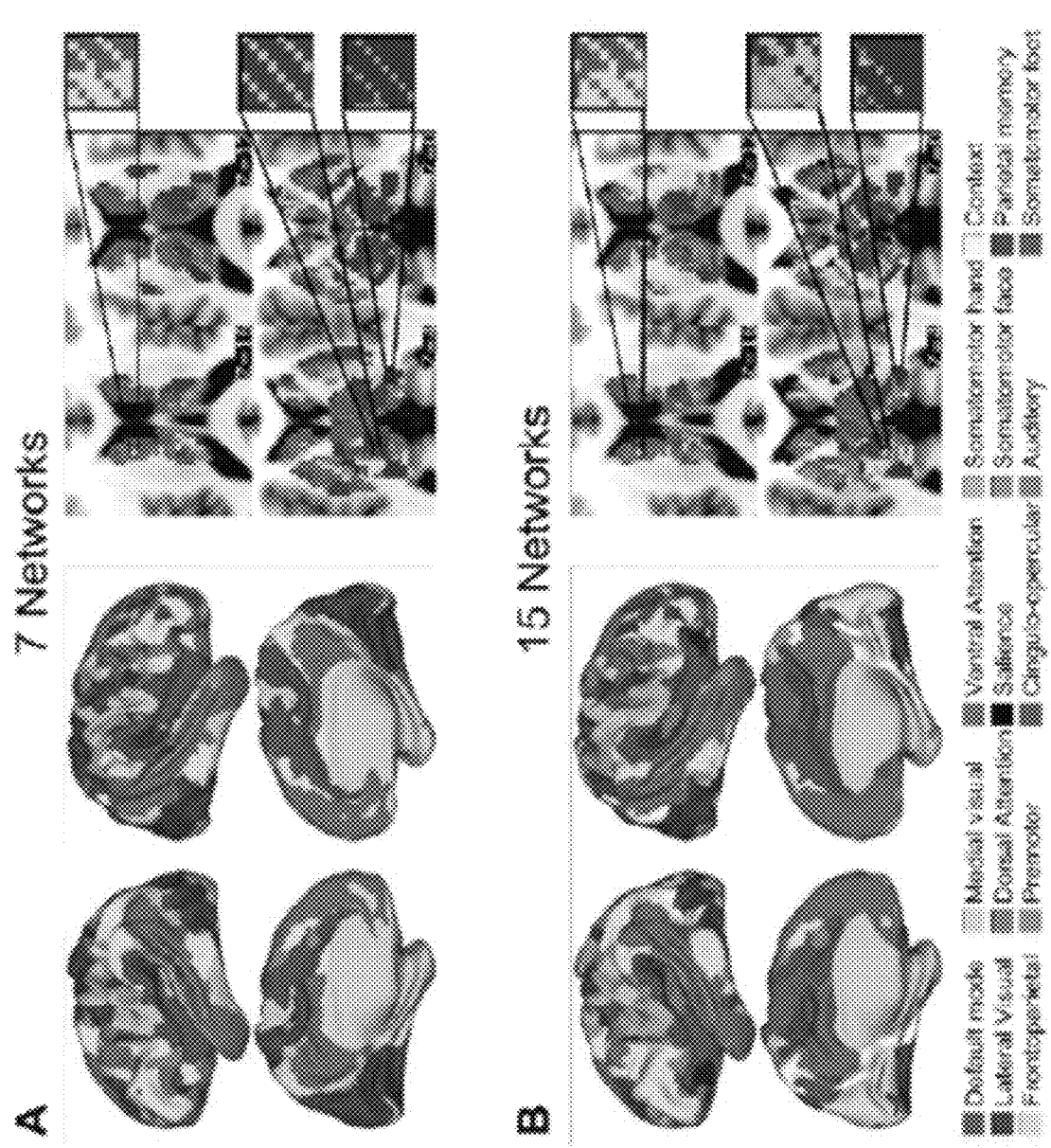
FIG. 15 shows integration zones in the subcortex with seven or fifteen cortical functional networks.

To show that integration was not driven by methodological factors, different numbers of a priori cortical networks were tested (i.e., 7 and 15 networks derived from Infomap, see www.mpaequation.com) as well as the effect of proximity to multiple networks (i.e., whether voxels with a greater number of distinct networks surrounding it are disproportionately biased to be defined as integrative). FIG. 15 shows that integration zones in the subcortex are not driven by the number of a priori cortical networks. The cortical functional networks derived from Infomap are shown on the left for 7-network (Panel A) and 15-network solutions (Panel B) in MSC06. The modified winner-take-all maps in the subcortex (right sides of Panels A and B) are highly similar when using either of the network solutions. The three major integrative zones reported above are consistent across levels of network granularity. The percent of integrative voxels (45% reported above) was 40% when using the 7-network Infomap solution and 48% when using the 15-network Infomap solution. Community density analyses support that integration was not driven by proximity to more networks, as an average of 46% of voxels with a community density>1 were defined as integrative (range 35-57% across subjects). Thus, high community density did not bias whether a voxel was defined as integrative or network-specific.

Further, the higher-resolution (2.6 mm) data collected for MSC06 confirmed the presence of integrative voxels in the subcortex, suggesting that integration was not a simple byproduct of mixing signals within 4 mm voxels. Further, a slightly higher percent of subcortical integrative voxels was found in MSC06 with the higher-resolution data (51% vs. 45%), which was largely due to more integrative voxels in the thalamus (62% with 2.6 mm vs. 38% with 4 mm). Thus, integration in the thalamus was not related to the resolution of the data.

Three Clusters of Network Integration are Present in the Subcortex

To determine which networks preferentially integrate with each other, the number of integrative subcortical voxels was quantified for each network-network pair (e.g., number of voxels integrating frontoparietal and salience networks) summed across subjects. These summed values were normalized by the total number of integrative voxels, resulting in a percentage of integrative voxels for each network-network pair. This network-by-network matrix was submitted to hierarchical clustering, and revealed three clusters of network integration, indicating preferential integration of particular networks (cophenetic r=0.82) (see FIG. 16A).

Figure 16A:
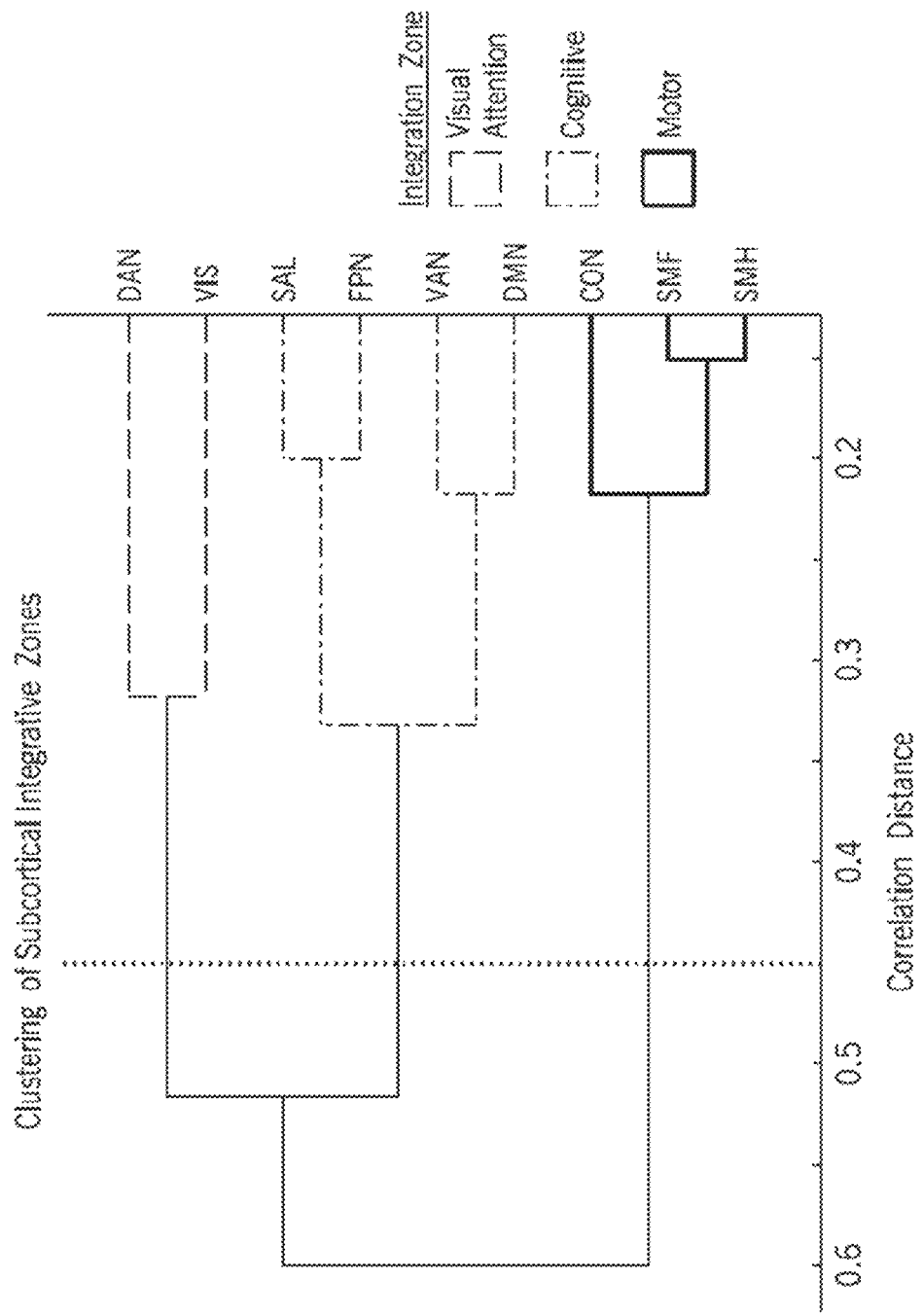
FIG. 16A shows three clusters of integrative zones.
Figure 16B:
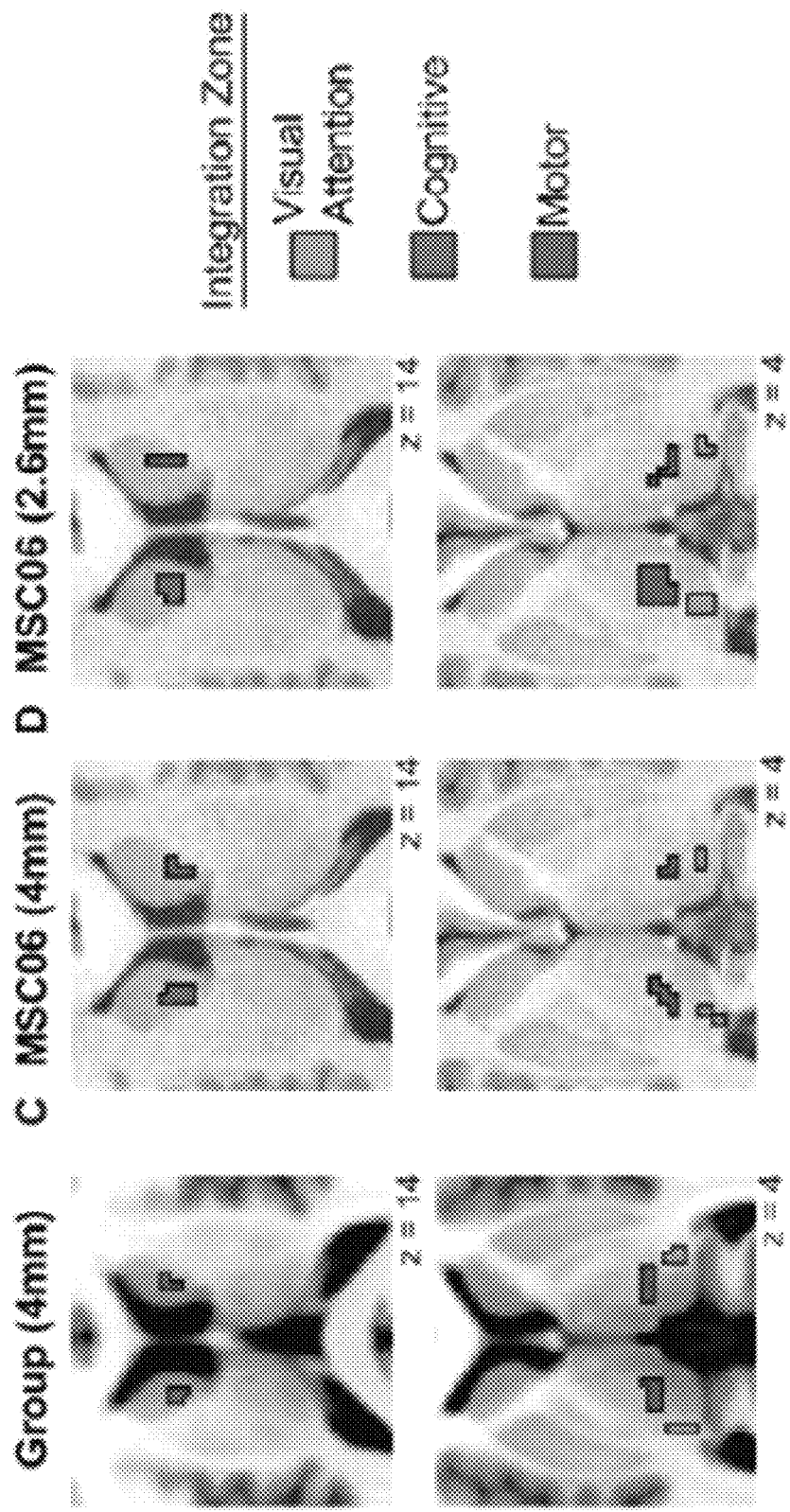
FIG. 16B shows maps of the three clusters of integrative zones shown in FIG. 16A.

FIGS. 16A and 16B show three clusters of network integration that are present in the subcortex. FIG. 16A shows hierarchical clustering revealed three clusters of network integration that involves 1) dorsal attention and visual networks, 2) salience, frontoparietal, ventral attention, and default-mode networks, and 3) cingulo-opercular, somatomotor face, and somatomotor hand networks. The most prominent locus of each cluster for the group average is shown in Column Group of FIG. 16B. The most prominent locus of each cluster for an example individual (MSC06) with 4 mm resolution data is shown in Column C of FIG. 16B. The most prominent locus of each cluster for the same individual (MSC06) with 2.6 mm resolution data is shown in Column D of FIG. 16B.

In the exemplary embodiment, a "motor integration" cluster was found, which demonstrated integration of the somatomotor hand, somatomotor face, and cingulo-opercular networks. Topographically, this integration was most prominent in the ventral intermediate thalamus (see FIG.

16B). A "cognitive integration" cluster was also found, which demonstrated preferential integration of the ventral attention, frontoparietal, salience, and default-mode networks. Integration of these higher-order networks was most prominent in the caudate (see FIG. 16B). A third "visual attention integration" cluster included the dorsal attention and visual networks. Integration of these networks was most prominent in the posterior portion of the thalamus (corresponding to the pulvinar, see FIG. 16B). These three clusters were identified at the individual subject level in both the 4 mm and 2.6 mm resolution data (see Columns C and D of FIG. 16B). This three-cluster solution was replicated using modularity, a graph theoretic clustering algorithm.

The Basal Ganglia and Thalamus Contain Four Distinct Types of Functional Zones

Figure 17A:
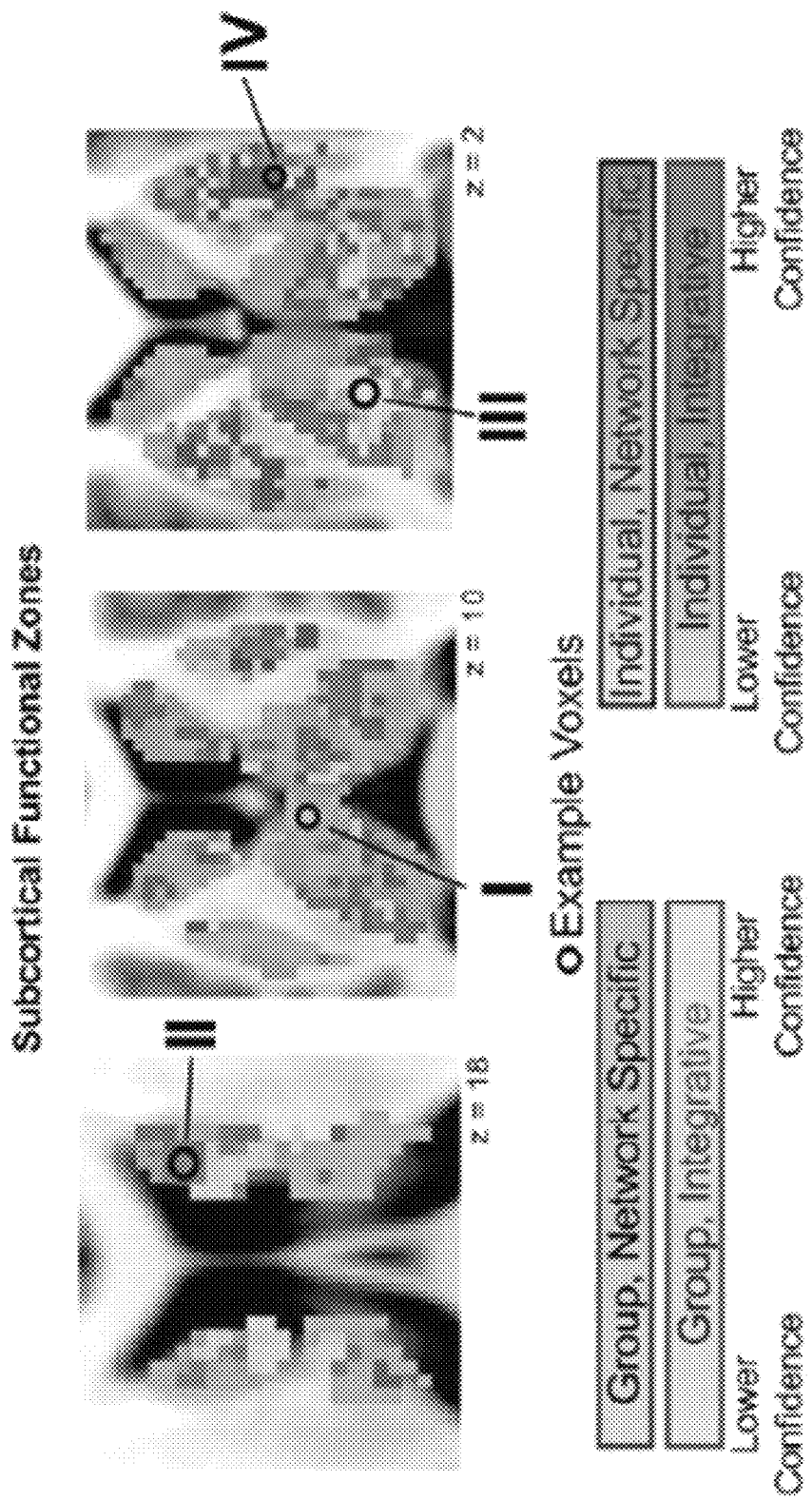
FIG. 17A shows subcortical functional zones.
Figure 17B:
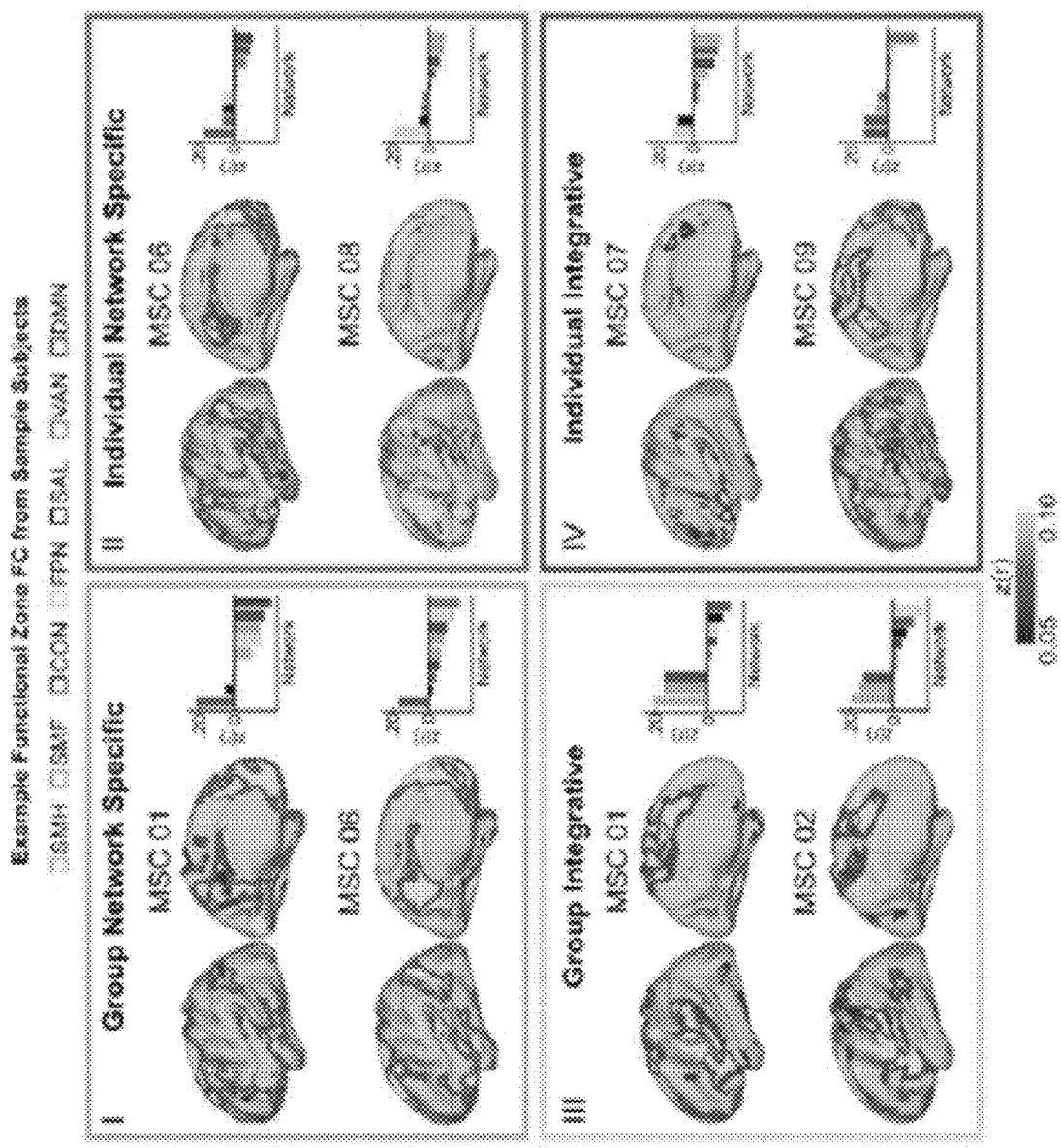
FIG. 17B shows example FC maps of functional zones shown in FIG. 17A.

Given the framework for understanding cortico-subcortical RSFC (see FIG. 4), basal ganglia and thalamus voxels exhibiting properties of integration vs. network-specificity were investigated, as well as whether the network(s) functionally connected with these voxels were consistent or variable across individuals. Voxels were considered network-specific if they exhibited strong RSFC to only one network, and were considered integrative if they exhibited strong RSFC to more than one network. Voxels were then considered consistent across the group if more than five subjects shared the same network assignment(s); otherwise, they were considered individually-specific. These criteria delineated four types of functional zones in the subcortex: (1) Group Network-Specific zones with consistent network-specificity in most subjects; (2) Individual Network-Specific zones with variable network-specificity across subjects; (3) Group Integrative zones with integration of the same networks in most subjects; and (4) Individual Integrative zones with variable network integration across subjects. FIG. 17A and FIG. 17B show that the subcortex contains these four distinct functional zones of Group Network-Specific (denoted as I), Individual Network-Specific (denoted as II), Group Integrative denoted as III), and Individual Integrative (denoted as IV). Anatomical distribution of each functional zone is shown in FIG. 17A. Examples of each type of functional zone are shown in FIG. 17B, using "example voxels" from FIG. 17A. Colored borders on the cortical surface represent the outline of the individual's cortical networks that show strong RSFC with the example voxel. Bar graphs display RSFC correlations between the example voxel and each cortical network.

To assess confidence in the zone assignments, a jack-knifing procedure was implemented in which the functional zones were assigned as described above ten times, leaving out a unique subject in each iteration. The percent of iterations a given voxel was assigned to a functional zone provides a confidence level for the functional zone assignment (see FIG. 17A). Color gradation in FIG. 17A displays the confidence of zone assignment for each voxel as estimated by the jack-knifing procedure. Variability in signal intensity after nonlinear atlas registration was not related to whether a voxel was identified as Group or Individual (comparison of signal intensity for Group vs. Individual voxels: $t=0.65$, $p=0.52$), indicating that the network assignment was not significantly related to anatomical alignment.

The RSFC profiles of example regions in the basal ganglia and thalamus from representative MSC subjects (varying by panel) that exemplify each of the four zones are displayed in FIG. 17B. Group Network-Specific zones included regions in the medial thalamus with preferential RSFC to the default-mode network in most subjects, and regions in the head of the caudate with preferential RSFC to the salience network in most subjects. Individual Network-Specific zones included the head of the caudate with preferential RSFC to the frontoparietal, ventral attention, salience, or default-mode networks. These zones were also found in regions of the putamen and dorsal thalamus with preferential RSFC to the cingulo-opercular, dorsal attention, salience, or somatomotor hand networks. Group Integrative zones were primarily located in the ventral intermediate thalamus with integration of cingulo-opercular and somatomotor networks (hand and face) in all ten subjects, and in the caudate with integration of control networks. Individual Integrative zones were located in portions of the putamen and in the ventral thalamus with variable integration of the default-mode, frontoparietal, ventral attention, salience, cinguloopercular, and somatomotor networks.

Experiment Discussion

The functional network organization of the human basal ganglia and thalamus are characterized at the level of the individual, using Precision Functional Mapping (PFM) with individual-subject fMRI data from the Midnight Scan Club (MSC) dataset. The analyses revealed distinct zones of network integration (strong functional connectivity with multiple networks) in 45% of the subcortex and network-specificity (strong functional connectivity with a single network) in 55% of the subcortex. Individual variability was found in cortico-subcortical RSFC in 43% of the subcortex and commonalities across the group in 57% of the subcortex. Integration zones were found in reliably localizable regions, such that the ventral intermediate thalamus integrated cingulo-opercular and somatomotor networks (motor integration zones), the pulvinar integrated dorsal attention and visual networks (visual attention integration zones), and the caudate nucleus integrated default-mode and several executive control networks (cognitive integration zones). The motor integration zones were remarkably consistent across all ten individuals, suggesting a vital role for the cingulo-opercular network in top-down control of motor functions. Integration zones were also found in regions of the putamen and pallidum, with individually variable integration of control and somatomotor networks. Overall, the ability to reliably measure cortico-subcortical RSFC in individuals using PFM holds promise for clinical treatments that require precise targeting of subcortical structures, such as deep brain stimulation (DBS).

Individual Specificity and Consistency in Subcortical RSFC Varies by Network

Individual variability was found in subcortical RSFC that was not captured by the group average and is only elucidated by individual-level analyses, in addition to broad similarities across subjects that were captured by the group average. The existence of both individual specific and shared features is consistent with recent cortical and cerebellar RSFC findings. Given the phylogenetically older origin of the subcortex compared to the cortex and the small size of subcortical structures, one may have expected less individual variability in the subcortex; yet strong individual-level contributions was found.

Particular functional networks in the subcortex—salience, frontoparietal, ventral attention, and dorsal attention—were relatively more variable across individuals, while others—cingulo-opercular and somatomotor—were more consistent. Recent studies have suggested that in the cortex, networks supporting top-down control show greater individual differences than other networks. It is notable that the cingulo-opercular network, an executive control network, was relatively more stable across individuals in the subcortex.

PFM Differentiates Four Types of Subcortical Functional Zones

The individual-specific approach identified four types of functional zones within subcortical structures: Group Network-specific, Group Integrative, Individual Network-specific, and Individual Integrative. Distinguishing these functional zones is possible only by obtaining individual-level results. In known methods, functional parcellation of subcortical structures in individuals were conducted with conventional quantities of resting state fMRI data (5-20 min per subject). However, the known methods employed relied upon a group-average reference and clustering algorithms within small structures, which are susceptible to bias due to spatial autocorrelation. Further, it was shown that 100 minutes or more are needed to reliably estimate individual cortico-subcortical RSFC in some structures (globus pallidus, thalamus). Thus, with the high reliability afforded by PFM, it was possible to identify functional zones beyond broad subdivisions of the subcortex in individuals. Indeed, more data was required to obtain reliable estimates in the subcortex compared to the cortex, which may be due to biological differences between structures that affect BOLD signal properties, or due to methodological differences, such as distance from the MR head coil, susceptibility artifact, and/or reduced gray-white contrast.

The Subcortex Contains Sites of Functional Network Integration and Specificity

Compelling human in vivo evidence was provided for the existence of network-specific and integrative zones in subcortical structures, consistent with animal models of "parallel and integrative" cortico-subcortical circuits. The presence of both network-specific and integrative functional zones in the subcortex may be for coordinating behavior that requires interactions between functions subserved by distinct functional networks, depending on the demands of the environment. That is, certain behavioral contexts may require independent functioning of a specific network, while others may require behavior that involves coordination of multiple network functions.

Previous human neuroimaging studies that discussed convergence zones or hubs within the basal ganglia and thalamus did not consider the functional network organization of the brain and/or necessarily relied upon group averaging, both of which may lead to the appearance of integration artifactually. For example, apparent integration of anatomically-defined frontal and parietal regions may simply reflect the anatomically distributed organization of the frontoparietal network rather than integration of multiple networks. In addition, group averaging may create the spurious appearance of integration since brain organization is spatially variable, and thus, the same brain stereotactic location may be linked to different networks in different individuals. If a particular location is connected to different networks in different individuals, averaging those signals across the group results in a signal correlated with multiple networks, even if this "integration" is not present in individual subjects. Consequently, mapping zones of integration must be done at the level of the individual.

The results are in line with existing evidence from structural and functional connectivity studies that suggest the basal ganglia and thalamus play central roles in the functional integration of cortical networks. One way in which this integration may occur is via cortico-striato-thalamo-cortical loops. Specifically, cortical inputs are integrated within the basal ganglia and thalamus before being projected diffusely to multiple cortical networks. Thus, the basal ganglia and thalamus simultaneously receive and integrate signals from the cortex and transmit signals to multiple cortical functional networks. The results provide corroborating evidence that specific focal regions of subcortex are functionally connected to multiple cortical networks.

fMRI data does not show whether functional integration in the subcortex reflects direct convergence of projections to and from multiple cortical networks or interdigitated projections at the neuronal level. Animal research suggests that overlap of terminal fields reflects interdigitated projections. The results may inform animal work by guiding particular anatomical targets of study. For example, integration zones that are common across subjects—e.g., motor integration zones in the thalamus—may be particularly good candidates for investigating projections at the neuronal level. Though the definition of integration zones may be influenced by the methods consistent results were shown across multiple approaches for defining integrative voxels (see FIGS. 11A and 11B). Further, these integration zones were corroborated with higher resolution (2.6 mm) data (see FIGS. 16A and 16B), which showed even greater integration in the thalamus with the 2.6 mm data than with the 4 mm data.

Functional Networks Converge Preferentially in Focal Regions of the Subcortex.

With the precision afforded by PFM, specific regions within subcortical structures that integrated multiple networks are depicted. These integration zones were found with standard (4 mm) as well as high-resolution (2.6 mm) fMRI data. They may serve as hubs connecting cortical functional networks via cortico-striato-thalamo-cortical loops. Hubs for information flow between cortical networks may also be located in the subcortex. The integration zones described here reflect the precise location of putative subcortical hubs and the specific functional networks that converge Motor Integration Zones: The integration zones that were consistently present in all ten individuals combined the somatomotor hand, somatomotor face, and cingulo-opercular networks in the ventral intermediate portion of the thalamus. Thalamic integration of these networks suggests that the cingulo-opercular network may exert some level of control over motor outputs via the thalamus. The current dominantly held view is that the cingulo-opercular network is involved in sustained aspects of task control. The cingulo-opercular network has properties similar to other controls networks (e.g., frontoparietal, salience), such as cue activations and error monitoring, that are distinct from lower-level processing networks (e.g., somatomotor networks). However, there is some evidence that a subset of cingulo-opercular regions in the cortex, unlike other control networks, link to somatomotor networks, and show activity corresponding to the moment a response is made. Non-human primate studies have identified "cingulate motor areas" that play a role in motor planning, preparation, and execution. Further, data from stroke subjects suggest that some cingulo-opercular regions are for executing motor functions. Interestingly, functional connectivity between the cingulo-opercular and somatomotor networks increases with development in a manner that suggests maturation of inhibitory control. Thus, the cingulo-opercular network appears to be linked to somatomotor networks in a way that is distinct from other control networks. The results indicate that the ventral intermediate region of the thalamus may be a locus of this integration.

Visual Attention Integration Zones: In the posterior thalamus, corresponding to the location of the pulvinar, preferential integration of the dorsal attention and visual networks was observed. Here, the pulvinar is shown as a site of integration of the visual network, which includes primary and association visual areas, and the dorsal attention network, which includes posterior parietal cortex and frontal eye fields and is involved in spatial attention. Specifically, structural connections exist between the pulvinar and primary and association visual cortex. Projections from the frontal eye fields and intraparietal sulcus indirectly innervate the pulvinar via ascending projections from the superior colliculus, forming cortico-colliculo-pulvino-cortical loops. These structurally and functionally integrative connections of the pulvinar suggest it may operate by coordinating attentional functions via integration of the visual and dorsal attention networks.

Cognitive Integration Zones: Particular networks supporting top-down control and attention (fronto-parietal, salience, ventral attention) and the default-mode network showed preferential integration in certain regions of the subcortex. Integration zones in the caudate and dorsal thalamus exhibited similar convergence of networks across individuals, while integration zones in the putamen and pallidum exhibited individually variable convergence of these networks. Together, the results suggest that these regions may act to functionally integrate control and default mode networks similarly across individuals in the caudate and dorsal thalamus, but variably across individuals in the putamen and pallidum.

Clinical Applications of Subcortical Functional Integration Zones

Given the involvement of cortico-subcortical circuits in many neurological and psychiatric disorders, the functional integration zones may be hotspots for treatment of neurological and psychiatric disorders. Zones with common profiles across individuals may be affected similarly across disorders, while zones with variable profiles across individuals are used to understand heterogeneity across and within specific disorders. Integration zones may be more affected in psychopathology than network-specific zones, relating to the complex nature of many neuropsychiatric disorders. The impairments often seen across multiple functional domains (motor, cognitive, affective) in many disorders are likely the result of alterations to integration zones, whereas alterations to network-specific zones may only affect one or a few functions. Thus, integrative zones are better suited as target locations for treatment than network-specific zones.

Figure 18:
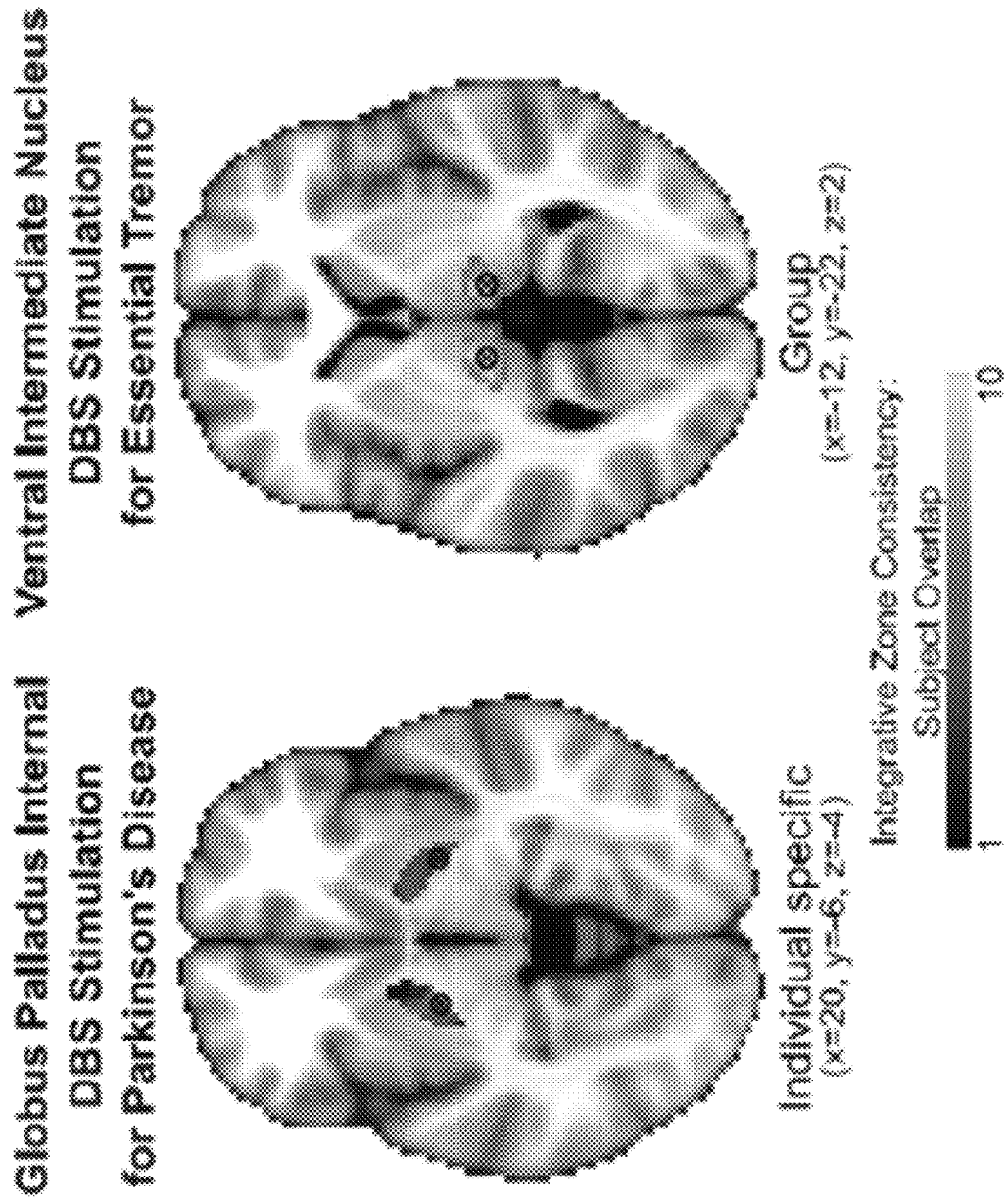
FIG. 18 shows the overlap of integrative zones and common sites of DBS.

Precision Functional Mapping of Subcortical Structures May Guide Targets for Deep Brain Stimulation (DBS) and Other Neuromodulation Approaches PFM may improve success of interventions that target subcortical structures, such as DBS. FIG. 18 shows the overlap of integration zones and common sites of DBS. Sites of DBS are shown with commonly targeted coordinates overlaid onto individual-specific (globus pallidus) and group (ventral intermediate thalamus) functional zones from the present disclosure. Color gradation shows the consistency of the integration zones across subjects. The globus pallidus site, which has variable success rates, overlaps with an Individual Integrative zone. The ventral intermediate thalamus site, which has consistently high success rates, overlaps with a Group Integrative zone.

The results illustrated in FIG. 18 show that PFM explains clinical variability of DBS outcomes and helps guide DBS placement. PFM may be used to locate subject-specific nodes of a particular functional network for which stimulation improves symptoms. For example, the DBS sites most commonly targeted for essential tremor fall in the Group (i.e., low variability) motor integration zones in the thalamus identified in the present study; DBS sites commonly targeted for PD and dystonia fall in Individual-specific (i.e., highly variable) sites in the globus pallidus internal (GPi). Thus, the consistent clinical improvement following stimulation of the ventral intermediate thalamic DBS target (i.e., >80% improvement in all essential tremor subjects) may reflect the highly consistent location of the motor integration zones across individuals. By contrast, the GPi location targeted for PD and dystonia varies in its functional connectivity across subjects. This finding may account for increased variability in clinical outcomes and lack of ability to identify optimal stimulation regions within the GPi target in group-level studies of DBS outcomes. There may be a relationship between clinical response rate to GPi DBS and a particular functional connectivity pattern at the stimulation site. If DBS in PD and dystonia were able to consistently target the same functional network(s), clinical outcomes may improve considerably.

Experimental Systems and Methods

Data from ten young adults (24-34 years old; 5 females; all right handed) from the publicly available Midnight Scan Club (MSC) dataset were used in the present disclosure. Here, information about the data and processing is described, as well as the specific analyses employed.

The MSC dataset includes structural and functional MRI data, as well as behavioral measures from 10 individuals (5 females, ages 24-34). fMRI data were collected over 10 sessions, each occurring on a separate day, beginning at midnight. Daily sessions were conducted in close succession, with all sessions completed within 7 weeks for all participants. During each scanning session, participants completed a 30 min resting-state run followed by fMRI scans during four other tasks: a motor task, a semantic task, a coherence task, and an incidental encoding memory task. MRI acquisition parameters and tasks are described below.

MRI Image Acquisition

Participants underwent 12 imaging sessions on a 3T MRI scanner, beginning at midnight, over the course of 3-6 weeks each. The first two sessions included structural MRI scans and the following ten sessions included functional MRI (fMRI) scans. Structural images included four T1-weighted scans (TE=3.74 ms, TR=2400 ms, TI=1000 ms, flip angle=8°, 0.8 mm isotropic voxels, 224 sagittal slices), four T2-weighted images (TE=479 ms, TR=3200 ms, 0.8 mm isotropic voxels, 224 sagittal, 224), four MRA and eight MRV scans. Functional images included 300 min total of eyes-open resting-state fMRI BOLD data (30 min per session) and 350 min total of task fMRI BOLD data using a gradient-echo EPI BOLD sequence=(TE=27 ms, TR=2.2s, flip angle=90°, 4 mm isotropic voxels, 36 axial slices). Gradient echo field map images (one per session) were acquired with the same parameters.

One participant (MSC06) underwent an additional 12 imaging sessions on a 3T MRI scanner, including fMRI scans with higher spatial resolution (gradient-echo EPI BOLD sequence: multiband factor 4, TE=33 ms, TR=1.1s, flip angle=84°, 2.6 mm isotropic voxels, 56 axial slices).

MRI Data Processing and Surface Registration

MRI data were preprocessed and sampled as follows:

Structural MRI: Cortical surfaces were generated. Briefly, each subject's averaged T1-weighted image was run through the recon-all processing pipeline to generate the anatomical surface. This surface was manually edited using Freeview to maximize accuracy, and registered into fs_LR_32 k surface space using a flexible Multi-modal Surface Matching algorithm. The subject-specific surfaces in native space were transformed into Talairach volumetric space by applying an average T1-to-Talairach transform.

Functional MRI Preprocessing: All functional data were preprocessed in volume space to reduce artifact and maximize cross-session registration. The preprocesses include (i) slice timing correction, (ii) intensity normalization to a whole brain mode value (across voxels and TRs) of 1000 for each run, and (iii) within-run correction for head motion. Then, the functional data were registered to Talairach atlas space using the average T2-weighted image and the average T1-weighted image. Distortion correction was applied using a mean field map for each subject and applying that field map to each fMRI session. Registration, atlas transformation, distortion correction, and resampling to 3 mm isotropic atlas space were combined into a single interpolation using FSL's applywarp tool. To account for anatomical differences between subjects, each subject's atlas-aligned T1-weighted images was non-linearly warped to MNI space using FSL's FNIRT. Volumetric time series subsequently were registered to each subject's registered T1-weighted images. All between subjects analyses and group average analyses were carried out on these atlas-transformed volumetric image time series.

Functional Connectivity Preprocessing: Additional preprocessing steps were applied to the resting-state fMRI data to reduce spurious variance unlikely to reflect neuronal activity. First, a motion censoring procedure was implemented, which in combination with the other processing steps has been shown to account for motion artifact. Temporal masks were created to flag motion-contaminated volumes based on framewise displacement (FD) and the temporal derivative of the root mean squared variance over voxels (DVARS). Frames with FD>0.2 mm or DVARS>5.36 were flagged. Two subjects (MSC03, MSC10) required additional correction for artifactual high-frequency motion in the phase encoding direction (anterior-posterior). Application of the temporal masks resulted in retention of 5704±1548 volumes per subject (range 2691-7530). Thus, even for the subject with the most motion-contaminated data, nearly 100 min of data was retained. Then, the data underwent additional processing steps, including (i) demeaning and detrending, (ii) interpolation across censored volumes using least-squares spectral estimation of the values at the censored timepoints, (iii) temporal band-pass filtering (0.005 Hz<f<0.01 Hz), and (iv) multiple regression of nuisance variables, including the global signal, principle components of ventricular and white matter signals (see below "Component-based nuisance regression"), and motion estimates, applied in a single step to the filtered, interpolated BOLD time series. Finally, censored volumes were removed from the data for all subsequent analyses.

For the additional 2.6 mm resolution data collected from MSC06, the data were processed the same as the 4 mm resolution data, with the following exceptions: (1) FD measurements were corrected for artifactual high-frequency motion in the phase encoding direction, (2) the FD threshold for motion censoring was 0.1 mm, and (3) the DVARS threshold for motion censoring was 6.

The cortical data were then registered to the surface, as described above. The cortical surface data and volumetric subcortical and cerebellar data were combined into CIFTI data format using Connectome Workbench. Voxels in the cerebellum and subcortex (including thalamus, caudate, putamen, pallidum, nucleus accumbens, amygdala, and hippocampus) were derived from the FreeSurfer segmentation of each subject's native average T1-weighted image, transformed into Talairach atlas space. Finally, the cortical surface functional data were smoothed (2D geodesic, Gaussian kernel, $\alpha=2.55$ mm). Due to the relatively small size of the basal ganglia and thalamus, spatial smoothing within the volume was not performed and the fully processed data was up-sampled to 2 mm isotropic voxels. To mitigate effects of signal contamination from nearby cortical areas (e.g., insula signal adjacent to the putamen), the time course of BOLD activity was regressed from any cortical vertices within 20 mm of a subcortical voxel.

Computer-based Nuisance Regression: The filtered BOLD time series underwent a component-based nuisance regression approach. Nuisance regressors were extracted from individualized white matter and ventricle masks, first segmented by FreeSurfer, then spatially resampled in register with the fMRI data. Since voxels surrounding the edge of the brain are particularly susceptible to motion artifacts and CSF pulsations a third nuisance mask was created for the extra-axial compartment (edge voxels) by thresholding the temporal standard deviation image (SDt>2.5%), excluding a dilated whole brain mask. Voxel-wise nuisance time series were dimensionally reduced, except that the number of retained regressors, rather than being a fixed quantity, was determined, for each noise compartment, by orthogonalization of the covariance matrix and retaining components ordered by decreasing eigenvalue up to a condition number of 30 ($\lambda max/\lambda min>30$). The retained components across all compartments formed the columns of a design matrix, X, along with the global signal, its first derivative, and the six time series derived by retrospective motion correction. The columns of X are likely to exhibit substantial co-linearity. Therefore, to prevent numerical instability owing to rank-deficiency during nuisance regression, a second-level SVD was applied to $XX^T$ to impose an upper limit of 250 on the condition number. This final set of regressors was applied in a single step to the filtered, interpolated BOLD time series.

Cortico-subcortical FC: To capture cortico-subcortical resting state functional connectivity (RSFC), RSFC between subcortical voxels and cortical functional networks were measured. First, each subject's individual cortical functional network organization was identified using the graph-theory-based Infomap algorithm for community detection. Derivation of the Infomap communities (representing networks) for each subject is as follows. Briefly, Pearson r correlations were computed between the BOLD time series (concatenated across sessions) among all cortical vertices, generating a 59,412 vertex×59,412 vertex correlation matrix. The matrix was thresholded across a range of densities from 0.1% to 5%, and community assignments were generated from the Infomap algorithm for each threshold. To assign putative network identities to each subject's communities, a matching procedure to networks identified for an independent group of 120 subjects was used. These cortical functional network assignments for each individual subject and for the group average are shown in FIG. 19A.

Figure 19A:
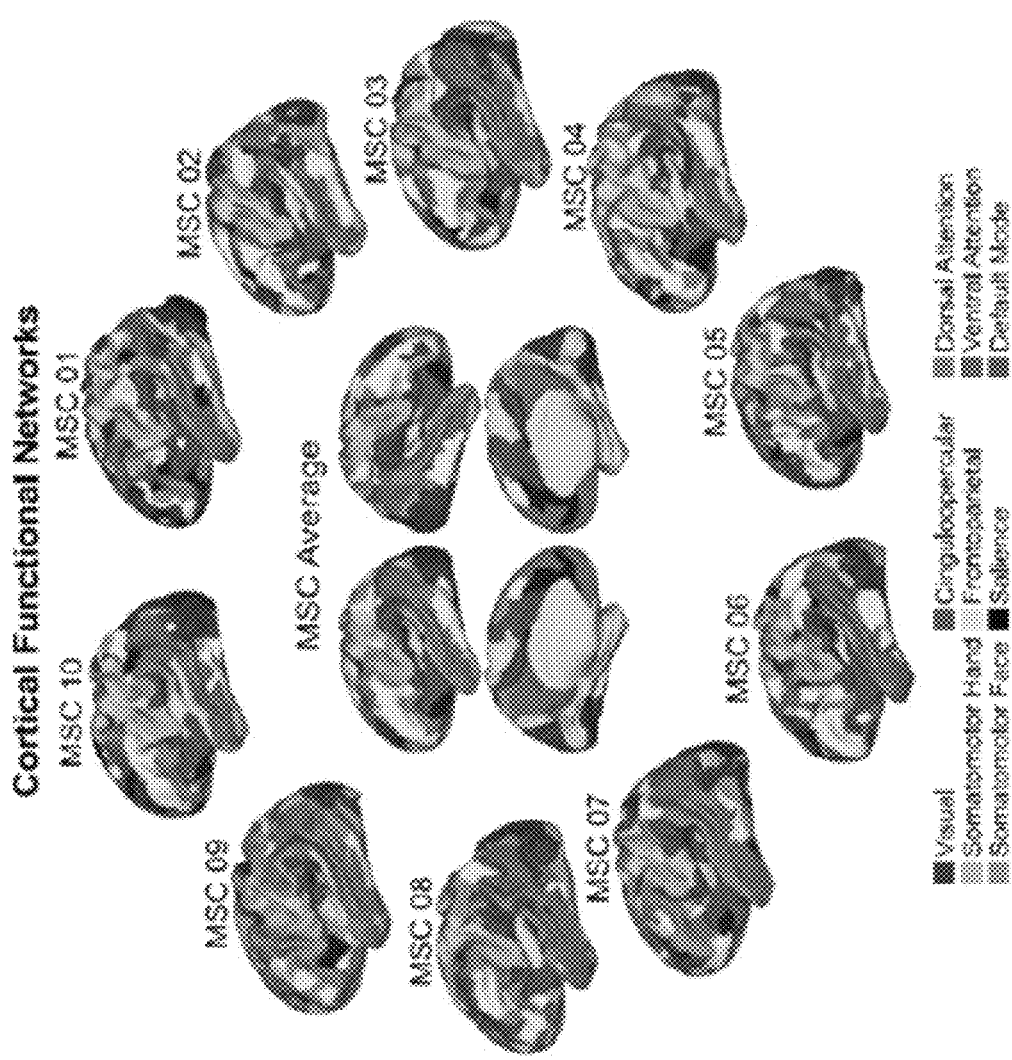
FIG. 19A shows functional cortical networks for all subjects.
Figure 19B:
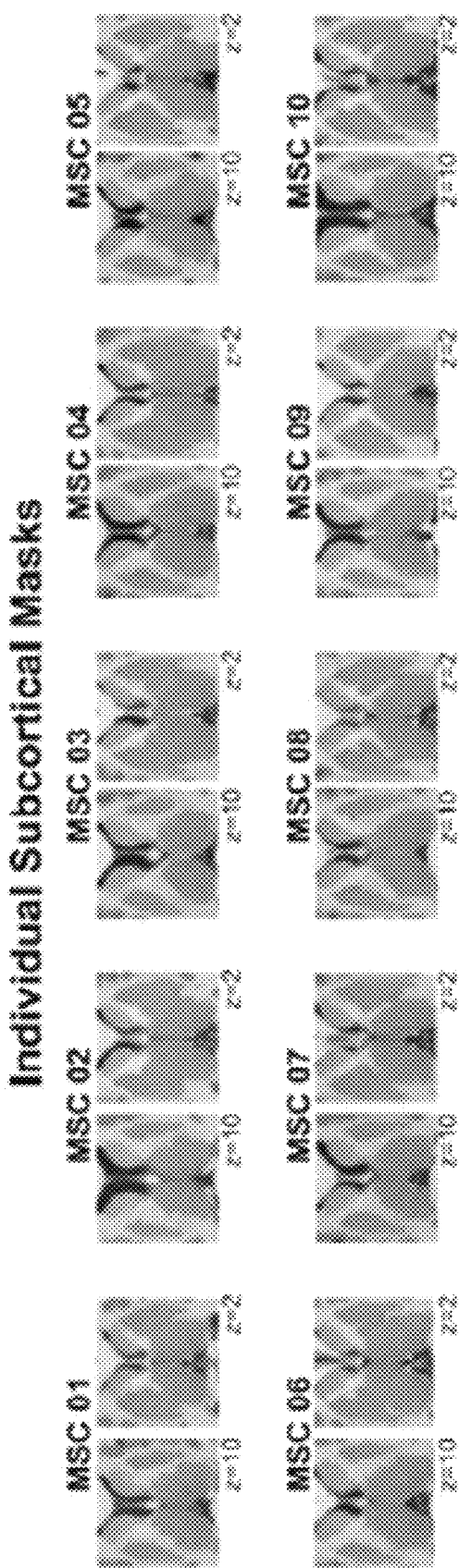
FIG. 19B shows subcortical mask for all subjects.

FIG. 19A and FIG. 19B show functional cortical networks and subcortical voxels for each individual. Individually-defined functional networks and the group average functional networks are shown in FIG. 19A. Nine functional networks were selected in order to investigate cortico-subcortical functional connectivity. Uncolored regions correspond to vertices that were not part of these nine networks according to the InfoMap network assignments. Note that including all 15 InfoMap networks (excluding unassigned and medial temporal vertices) did not change the results. Subcortical masks from Freesurfer and manually edited using Freeview are shown for each individual in FIG. 19B, where Light blue indicates caudate, pink for putamen, violet for pallidum, and green for thalamus.

For the purposes of the subcortical-cortical analyses, the nine cortical functional networks selected (the same 9 for all subjects) are: somatomotor hand, somatomotor face, visual, frontoparietal, cingulo-opercular, dorsal attention, ventral attention, salience, and default-mode. These cortical networks are shown for each subject (see FIG. 19A). Then, the average time series was computed across vertices for each of these nine cortical networks in each hemisphere separately, and correlated them with the time series from each subcortical voxel (voxels within each subject's thalamus, caudate, putamen, pallidum, and nucleus accumbens) in the ipsilateral hemisphere (consistent with anatomical connections) (see FIG. 19B). Note that the results do not appreciably change when the analyses are conducted using correlations from both hemispheres (83% of subcortical voxels have identical "winning" network assignments). Given the close anatomical proximity of several subcortical structures to certain regions of cortex, the cortical signal was regressed within 20 mm of the subcortex from each subcortical voxel time series in order to mitigate potential artifactual inflations in correlations due to signal bleed. The resulting subcortical voxel-to-cortical network correlation matrices (one per subject) were used for subsequent analyses.

The same procedures were applied to the whole group of subjects in order to compute the group averaged subcortical voxel-to-cortical network correlation matrix. The nine cortical functional networks were selected from the group average Infomap communities.

These procedures were repeated after partialing out the time series of activity of each cortical network from every other network before quantifying RSFC between each subcortical voxel and cortical network. Voxel-wise results were highly similar (r=0.75) between approaches using full correlations and partial correlations. These procedures were also repeated using the 15-networks Infomap solution (excluding unassigned vertices and medial temporal lobe vertices due to proximity to the subcortex) as well as using a 7-network Infomap solution (see FIG. 15).

In addition, the correlation results were compared against a null model using randomly rotated cortical networks. First, for each subject, that subject's cortical networks were randomly rotated around the spherical expansion of the cortical surface to produce cortical objects that had the same size, shape, and spatial distribution as real networks, but in random locations. Next, for every subcortical voxel, the average correlation was calculated to each rotated cortical network, excluding portions of the rotated networks that fell on the medial wall or in susceptibility artifact regions. This rotation and calculation of correlations was repeated 1000 times, generating a null distribution of correlations. Finally, for each network-subcortical voxel connection, the percent of iterations was calculated for which the correlation to the real network was stronger than the correlation to that iteration's rotated version of that network. This value represents the likelihood that a voxel's correlation to a cortical network is stronger than expected if the cortical network location was randomized. This "percent stronger than null" map was compared to the standard functional connectivity correlation maps for each network for each subject.

Reliability of cortico-subcortical FC: Using an iterative split-half reliability analysis each individual subject's reliability of cortico-subcortical RSFC was computed. For each subject, the ten scan sessions were randomly divided into two subsets of five sessions each. Half of the data (motion censored) was randomly selected from one of the subsets to serve as the comparison data, and a varying amount of data (5 to 100 minutes in 5 minute increments) was randomly selected from the other subset to serve as the test data. Reliability was estimated by computing the average correlation between the subcortical voxel-to-cortical network matrices for the comparison and test data. This procedure was iterated 1000 times using different subsets of random data (i.e., random halves of the data) in each iteration.

As some regions within the subcortex may have better reliability than others, a voxelwise split-half reliability analysis was conducted. For each subject, the ten scan sessions were randomized, concatenated, split into two halves, and the subcortical voxel-to-cortical network correlation matrices were computed for each half. Reliability for each voxel was estimated by computing the correlation between the halves. The relationship between reliability and tSNR was tested by correlating these two measures across voxels for each subject. In order to mitigate the effects of voxels with relatively poor reliability, subsequent analyses excluded those voxels having reliability<0.5 for each subject.

Task Activations: Task fMRI data were processed. Briefly, the cognitive/perceptual tasks included a pair of mixed block/event-related design tasks that began with a task cue followed by a block of jittered trials in each task. The "language" task trials included single words and participants were asked to determine whether the words were nouns or verbs. The "perceptual" task included Glass dot patterns at either 50% or 0% coherence. Participants were asked to determine whether or not the dots were arranged concentrically. The motor task, modeled after the HCP motor task, included blocks of movements of either left or right hand, left or right foot, or the tongue.

After fMRI preprocessing, task fMRI data were entered in a General Linear Model (GLM) separately for each session from each individual using IDL software (FIDL). The mixed design tasks were modeled jointly in a single GLM with separate event regressors for onset and offset cues from each task, trials in each task (nouns and verbs for the cognitive task, 0% and 50% for the perceptual task), and a sustained block regressor for the task period. Event regressors were modeled using a finite impulse response approach including delta functions at each of 8 timepoints, allowing for the complete modeling of different HRF shapes. The motor task was modeled with separate block regressors for each motor condition.

Deactivations associated with the default mode network were identified using a contrast of the third and fourth timepoints from all conditions in the mixed design tasks (against an implicit, unmodeled, baseline). Activations associated with the somatomotor hand network were identified using a contrast between left and right hand movement blocks with left and right foot movement blocks.

Similarity Analysis: Similarity analyses were carried out. For each subject, the ten scan sessions were randomized, split into two halves, and concatenated. The subcortical voxel-to-cortical network correlation matrices were computed for each half and vectorized. Then the similarity (Pearson z(r)) between the two halves of data was calculated both within split halves of an individual's data and between split halves of every other individual. This analysis resulted in a similarity matrix, in which off-diagonal elements represent variance shared across individuals (i.e., group effect), and on-diagonal elements represent variance shared across scanning sessions within an individual. Variance unique to individuals vs. the group was quantified by normalizing (dividing) variance shared across individuals (group effect; off-diagonal elements) by subject similarity (on-diagonal elements). The production of similarity matrices and quantification of group vs. individual level effects were computed separately for the basal ganglia and thalamus.

The between-subject variability in the subcortex was examined. The standard deviation of correlations was calculated between each subcortical voxel and every cortical network across subjects. Each subcortical voxel was then assigned to a single network (winner-take-all approach) in order to compare the standard deviation of higher-order network subcortical voxels (frontoparietal, dorsal attention, ventral attention, salience, cingulo-opercular, default-mode) to that of processing network subcortical voxels (visual, somatomotor hand, somatomotor face) using a t-test.

Network Specificity vs. Integration: To determine which subcortical voxels were "network-specific" vs. "integrative," a modified winner-take-all analysis was implemented. For each subject, a "winning" network was assigned to each subcortical voxel based on the strength of the correlation between that voxel and each cortical network. The network with the strongest correlation was deemed the winner, or the winning network. Then, a voxel was categorized as network-specific if its correlations with all other networks were less than ⅔ (66.7%) of its correlation with the winning network. If this criterion was not met, the voxel was categorized as integrative, and those networks within ⅔ of the winning network were also considered winners. This procedure yielded multiple networks (minimum two networks; maximum four networks—note that there was no instance with more than four networks) within an integrative voxel, whereas a network-specific voxel, by definition, was occupied by one network. Given the somewhat arbitrary nature of the 66.7% threshold, 50% and 75% were also tested, which resulted in highly similar distributions of network-specific vs. integrative functional zones (see FIG. 11A).

In addition, an alternative approach was tested for determining network specificity vs. integration based on effect size (for example, Cohen's d). For every subcortical voxel, t-tests were computed comparing its correlations with the winning network (all cortical vertices within that network) to its correlations with every other network (all cortical vertices within a subsequent network). Thus, it was possible to compute the effect size of each comparison. Voxels were determined to be network-specific vs. integrative based on whether the observed effect size between the winning network and another network was greater than or less than a benchmarked effect size. The resulting zones of integration for small (d=0.2), medium (d=0.5), and large (d=0.8) effect sizes are shown (see FIG. 11B). This approach yielded similar zones of integration.

Network-specific voxels were pictorially shown and colored by their affiliated network, whereas integrative voxels were colored by each network represented in that voxel (striped pattern) (see FIG. 12). For integrative voxels, the base color was determined by the network assigned to that voxel in separate, previously described group-averaged data (WashU 120) using a standard winner-take-all method (basal ganglia winner-take-all parcellations). Thus, if a network represented in an integrative voxel was shared with the network assigned to that voxel in the WashU 120, the voxel's base color was assigned to that network, and the other networks were shown as thin stripes. If none of the networks were shared with the WashU 120, the base color was assigned to the network with the strongest correlation.

The concern arising from delineating integration zones within the subcortex is the spatial proximity of networks given the relatively smaller size of subcortical structures. To lend support for integration zones rather than solely proximity to multiple networks, a community density analysis was performed across the subcortex. Using the winning network assignment for each subcortical voxel from the winner-take-all analysis, community density was determined by counting the number of networks within a spotlight of 3 mm. If integration was largely due to high community density, the majority of high community density voxels is expected to be integrative. To test this prediction, for each subject all voxels with a community density>1 were extracted, which indicates the presence of at least one neighboring voxel with a different network assignment, and calculated the percent of those voxels that were integrative.

Quantification of Network-Specificity and Integration across Functional Networks: To examine how network-specificity and integration were distributed across functional networks, the number of network-specific and integrative voxels for each network was quantified. A network-by-network matrix was generated representing the number of voxels, summed across subjects that were integrative for all pairs of networks (e.g., number of integrative voxels containing frontoparietal and salience networks). These summed values were normalized by the total number of integrative voxels, resulting in a percentage of integrative voxels for each network combination. These percentages were calculated separately for each structure. The degree to which functional networks cluster with respect to patterns of integration (i.e., extent to which certain networks preferentially integrated with each other) was determined. To this end, a hierarchical clustering analysis was performed using Matlab's linkage, pdist, and dendrogram functions, with default setting for determining the optimal cluster solution. The clusters produced by the hierarchical clustering analysis were validated by submitting the network-by-network matrix to a graph theoretic clustering analysis (modularity), replicating a three cluster solution.

Defining Functional Zones in the Subcortex: Having determined network-specific and integrative subcortical voxels for each subject, identifying zones of network-specificity and integration that were common across the group vs. variable across individuals was conducted. First, a voxel was considered network-specific if that voxel was network-specific in >5 subjects. A voxel was considered integrative if that voxel was integrative in >5 subjects. If a voxel met neither criterion, it was not assigned to a zone. For the assigned voxels, it was next determined whether they exhibited RSFC that was common across the group (Group) or varied across individuals (Individual). For network-specific voxels, they were considered Group if >5 subjects shared the same network assignment; otherwise, they were considered Individual. For integrative voxels, they were considered Group if at least two of the networks assigned to that voxel were present in >5 subjects; otherwise, they were considered Individual. Thus, four voxel types were defined: Group Network-specific, Group Integrative, Individual Network-specific, and Individual Integrative. To delineate functional zones, a cluster threshold of 20 voxels was applied and removed extraneous voxels that did not share more than one face with other voxels in that cluster, i.e. ensuring a Euler characteristic of two.

To determine the stability of these functional zones, a jack-knifing procedure was performed. The steps for defining the four zones were repeated ten times, leaving out a subject with each iteration. The percent of iterations that each voxel was assigned to each of the four zone types as then calculated. Thus, confidence in functional zone assignment was estimated (see FIG. 17A).

To display examples of each of the four types of functional zones, an example voxel was selected within each type (see FIG. 17A). The correlations from these voxels to all cortical vertices on the cortical surface with subject-specific Infomap network borders for two representative subjects, as well as the strength of the correlations to each cortical network are also displayed (see FIG. 17B).

Example 2: Individual-Specific Functional Connectivity of the Amygdala

Psychiatric disorders are a leading cause of morbidity and mortality worldwide. Over the past few decades, little progress has been made in reducing this burden, in part because personalized brain-based models of mental illnesses are lacked to be used to diagnose and guide treatment in individual subjects. The amygdala is a structure in the medial temporal lobe that is essential to any personalized model of mental illness that serves to transform this outlook. In research settings, functional connectivity of the amygdala as measured with functional magnetic resonance imaging (fMRI) has been extensively correlated with symptoms, longitudinal course, and treatment response in many different psychiatric disorders. A substantial roadblock in translating these research findings into clinical-practice biomarkers, however, is an inadequate understanding of the amygdala's role within the larger functional network organization of the brain in individuals. As a result, ability to create models of function and dysfunction in individual subjects to guide personalized treatment is limited.

In the exemplary embodiment, the position of the amygdala and its functional subdivisions within the network organization of the brain in 10 individuals (5 hours of fMRI data per person) were investigated. Three functional subdivisions within the amygdala of each individual were characterized. One subdivision is preferentially correlated with the default mode network, a second is preferentially correlated with the dorsal attention and fronto-parietal networks, and third subdivision does not have any networks to which it is preferentially correlated relative to the other two subdivisions. All three subdivisions are positively correlated with ventral attention and somatomotor networks and negatively correlated with salience and cingulo-opercular networks. These observations were replicated in an independent group dataset of 120 individuals. There is substantial across-subject variation in the distribution and magnitude of amygdala functional connectivity with the cerebral cortex that related to individual differences in the stereotactic locations both of amygdala subdivisions and of cortical functional brain networks. Finally, using lag analyses, temporal ordering of fMRI signals in cortex relative to amygdala subdivisions is provided. Altogether, a detailed framework of amygdala-cortical interactions is provided and used as a foundation for models relating aberrations in amygdala connectivity to psychiatric symptoms in individual subjects.

A basic organizing principle of the human brain is that it may be divided into approximately 10 to 20 large-scale, distributed functional brain networks. fMRI studies have established the connectivity properties within and between these large-scale brain networks in human adults, as assessed by correlations in infra-slow activity (ISA, <0.1 Hz) between brain regions. Moreover, information regarding the temporal direction of these within- and between-network connections has been provided by computing the temporal offset between ISA from two brain regions that maximizes their correlation. Altogether, these tools have established a sophisticated network model of the human brain in which ISA propagates in specific directed patterns within and between networks. Variation in the strength and timing of these connections is linked to risk for psychiatric illnesses.

The biology and function of the amygdala is informed by its position within this network-level organization. In contrast to description of amygdala circuitry in rodents and non-human primates, a detailed description of the brain networks that connect to specific amygdala subdivisions, or of the direction and timing of these functional relations, in individual humans were lacked. Prior human fMRI studies have examined functional connections between the amygdala and specific cortical regions and their associations with psychiatric symptoms. However, this prior work has often relied on describing functional connectivity between pre-defined anatomic partitions of the amygdala and cortical locations defined by averaging across large groups of subjects. There was substantial variation in the location and spatial extent of the 3 amygdala partitions across individuals. In addition, individuals vary in the layout of functional brain networks on the cerebral cortex and that brain-behavior relations are stronger in individualized network maps than in group-averaged templates.

In the systems and methods described herein, these challenges are addressed and the amygdala and its subdivisions are placed within the larger network organization of the human brain by adopting an individualized approach. Repeated sampling or repeated imaging sessions and precision mapping techniques are used to define 3 amygdala subdivisions separately in 10 individuals, each with 5 hours of resting state functional connectivity data (the Midnight Scan Club, or "MSC" dataset). Amygdala subdivisions are defined for each individual on the basis of connectivity patterns with cortex. For the primary analysis, three data-driven amygdala subdivisions are defined for each individual in an effort to recapitulate the tripartite models of the amygdala prevalent in the human neuroimaging literature. Connectivity of amygdala subdivisions are related to individual-specific functional brain networks on cortex, and lag analysis is used to determine the timing of ISA in amygdala subdivisions relative to cortical networks. The strength, direction, and timing of connectivity between the amygdala and cortex is thus directly related to each individual brain's functional organization. For comparison, the standard spatial template-defined group-based functional connectivity mapping in an independent dataset of 120 individuals collected at Washington University (the "WU" dataset) was performed.

Individualized Amygdala Subdivisions

Figure 20A:
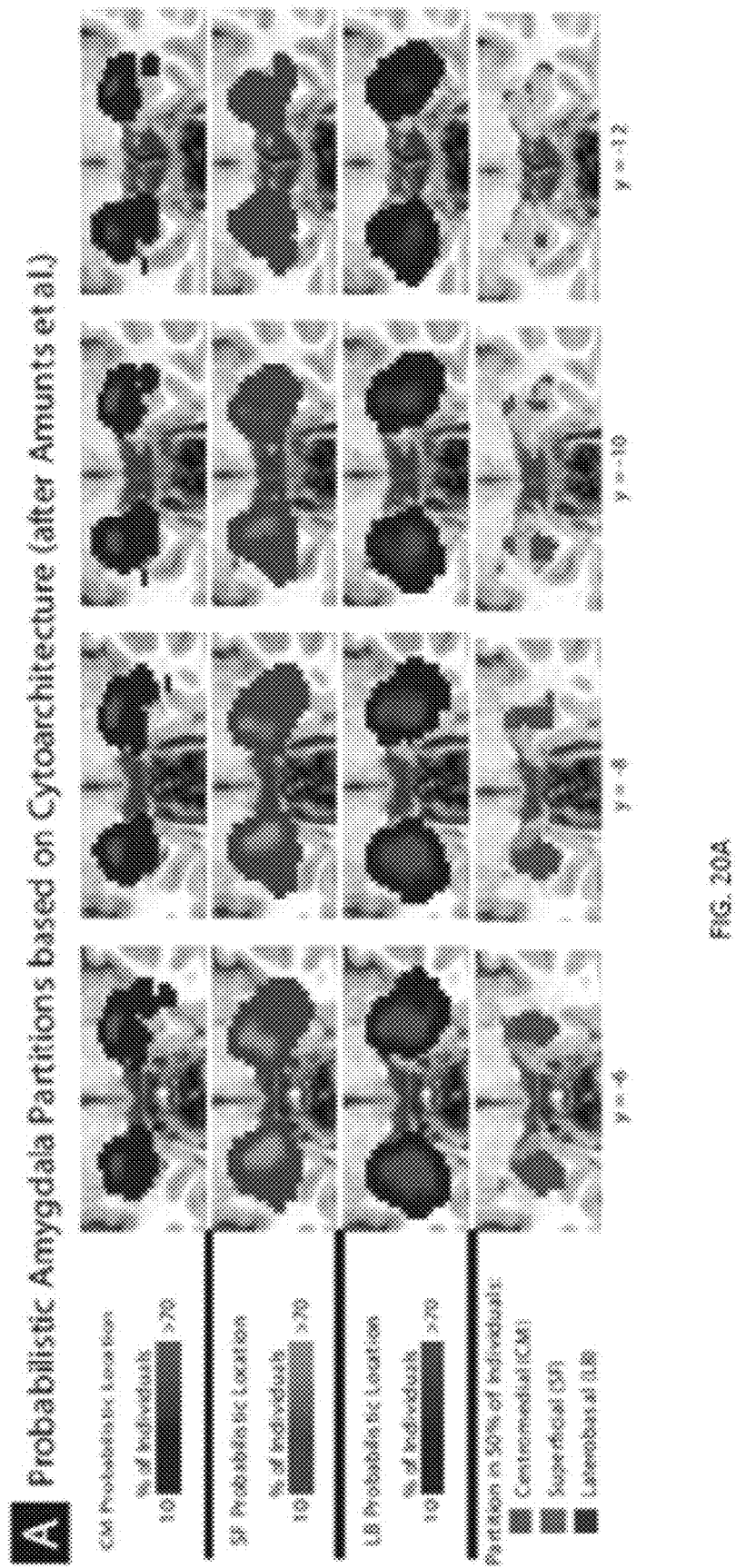
FIG. 20A shows probabilistic amygdala partitions based on cytoarchitecture.

Standard group-based studies typically use probabilistic structural templates to divide the amygdala into three partitions, corresponding to group-average anatomical locations of the centromedial, basolateral, and superficial amygdala partitions. This template is illustrated in FIG. 20A, which depicts the probabilistic location of three amygdala partitions as determined postmortem by cytoarchitecture in 10 individuals from Amunts et al. The spatial extent of the probabilistic partitions in this illustration are trimmed to fit within the boundaries of the amygdala as defined in the group-average WU dataset by FreeSurfer; the actual sizes of the probabilistic templates are much larger and extend into nearby white matter and cortical areas. Note the high degree of variability in the size and spatial extent of these partitions. As such, these probabilistic templates may not accurately define the location of amygdala subdivisions in all individuals.

To address this issue, an approach was developed to define 3 amygdala subdivisions separately in each of 10 individuals using functional connectivity. The number of subdivisions was set to 3 in order to maintain consistency with prior studies and to compare the location and variability with Amunts et al. Other numbers of clusters may be used. Analyses of 2-cluster solutions and for the entire amygdala for each individual are included in the Supplement. For the common analysis, three amygdala subdivisions were defined separately in each individual by clustering amygdala voxels on the basis of cortical functional connectivity patterns using k-means clustering. Subdivisions were matched across individuals using a similarity algorithm (see Supplementary Methods for details). Subdivisions were labeled according to the network with which they had the highest positive functional connectivity relative to the other two subdivisions, as described in greater detail below.

Figure 20B:
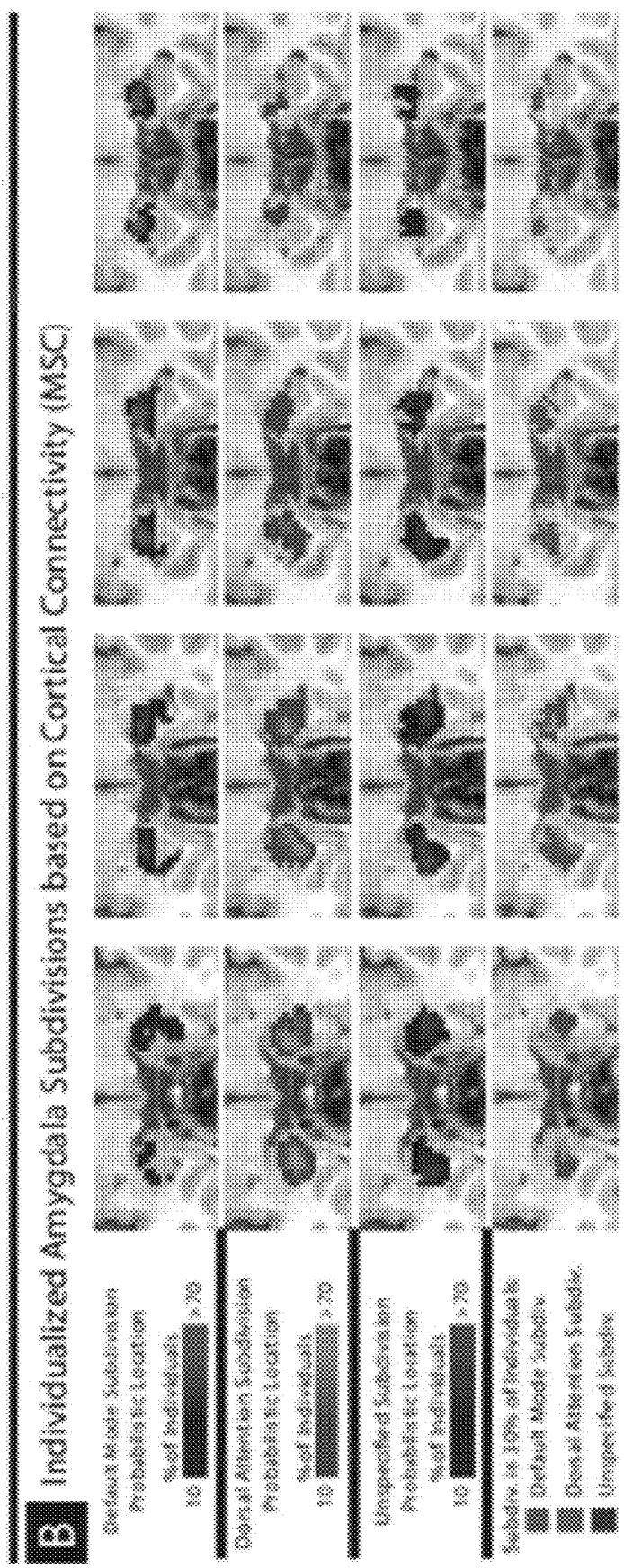
FIG. 20B shows amygdala partitions based on FC.
Figure 20C:
FIG. 20C shows group amygdala partitions based on FC.

FIG. 20B depicts data in which the locations of 3 amygdala subdivisions were derived in 10 individuals based on functional connectivity. Subdivisions were determined on the basis of having homogenous within-subdivision connectivity to cortex. Subdivisions were named on the basis of the cortical network to which they had the highest connectivity relative to the other 2 subdivisions. The variability across subjects in the location of these 3 subdivisions is similar to the variability present in cytoarchitecturally determined amygdala partitions. A different threshold is used to visualize the modal locations of the probabilistic partitions (50%, bottom row of FIG. 20A) versus the empirically derived subdivisions (30%, bottom row of FIG. 20B), because raising the threshold to 50% for the empirically derived dataset results in small areas of overlap that are difficult to visualize. The requirement for a different threshold across datasets may relate to the larger overall spatial extent of the probabilistic partitions; or may indicate that there is slightly more variability in location in the empirical subdivisions. FIG. 20C empirically defines amygdala subdivisions in a group dataset of 120 individuals on the basis of cortical connectivity patterns, identical to the procedure used to define individualized subdivisions in FIG. 20B. Note the similar but not identical spatial arrangement of subdivisions compared to the other 2 datasets.

The empirically defined individual amygdala subdivisions (FIG. 20B) resemble the amygdala partitions in both average location and inter-individual variability (FIG. 20A). One empirically defined subdivision was anatomically superior in most individuals, overlapped most strongly with the probabilistic location of the centromedial partition as quantified by the Dice coefficient, and is referred to as the 'default mode' subdivision due to its greater connectivity with the default mode network (DMN) compared to the other amygdala subdivisions (see below). A second subdivision was located medial in most individuals, overlapped most strongly with the probabilistic location of the superficial partition, and is referred to as the 'dorsal attention' subdivision due to its greater connectivity with the dorsal attention network (DAN) compared to the other amygdala subdivisions. Finally, a third subdivision was located ventral in most subjects and overlapped most strongly with the laterobasal partition. This third subdivision is referred to as the 'unspecified subdivision', because it did not show preferentially stronger functional connectivity with any specific network compared to the other amygdala subdivisions; rather, it demonstrated connectivity properties that were shared across the entire amygdala. An alternative 2-cluster solution defined subdivisions in each individual with properties largely similar to the default mode and dorsal attention subdivisions.

Although the empirical, functionally defined subdivisions overlapped with the probabilistic, anatomically defined partitions on average, there was substantial across-subject variability (see FIG. 20B). This across-subject variability appeared similar to the across-subject variability in cytoarchitectonically defined partitions (FIG. 20A). A potential consequence of this variability is that applying a common template to all individuals may mislabel the amygdala subdivisions in many individuals. As a result, subdivision-cortical network relations may be obscured. The same empirical procedure was employed to define the 3 subdivisions in the WU group-average dataset and obtained 3 similar subdivisions (FIG. 20C).

Group Average Functional Connectivity of Probabilistic Amygdala Partitions

Figure 21:
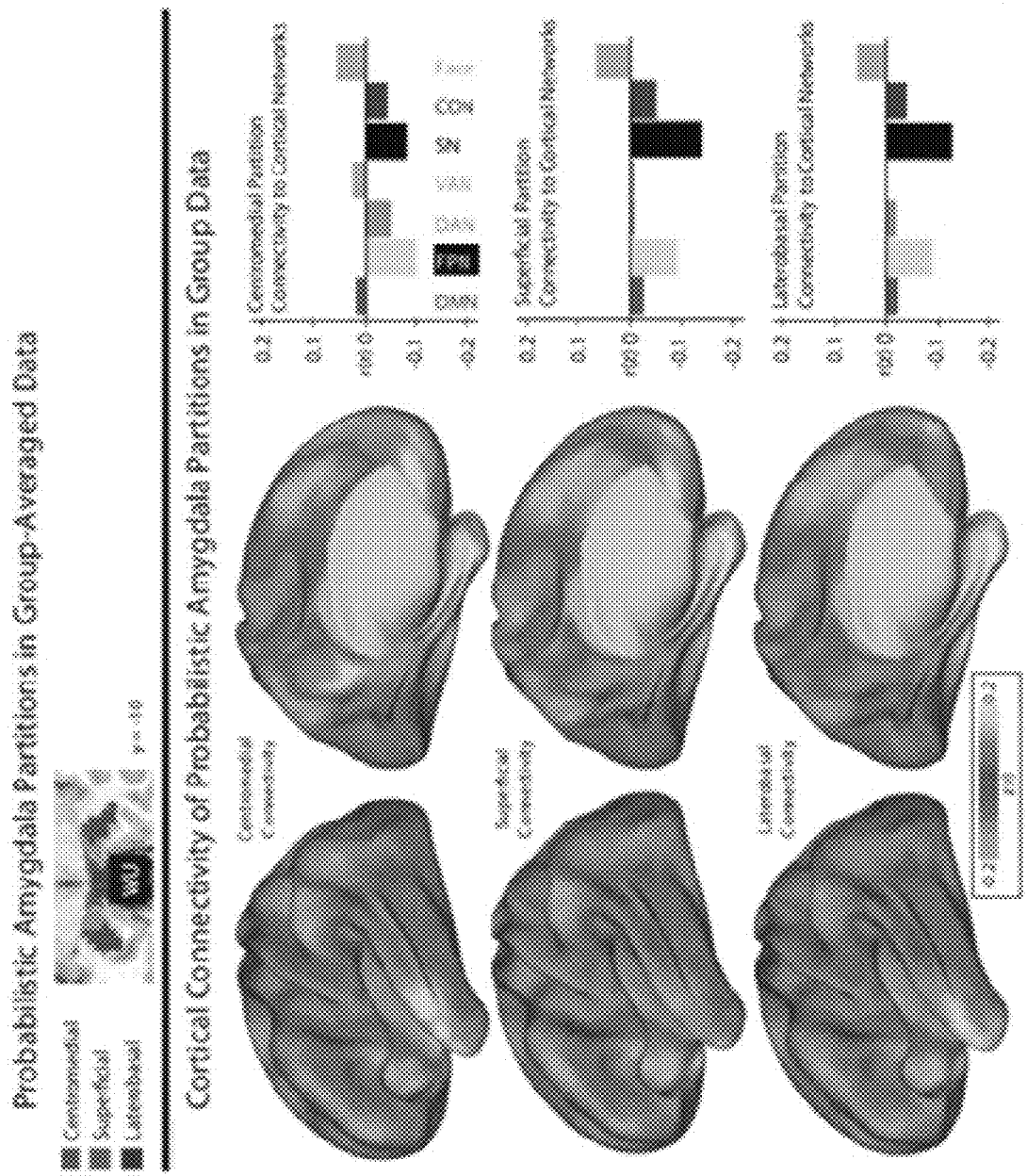
FIG. 21 shows probabilistic amygdala partitions and their FC.

FIG. 21 shows that the connectivity patterns of three probabilistic amygdala partitions to cortex are highly similar to each other. In traditional, group-based analyses, connectivity is measured between stereotactically defined partitions of the amygdala and particular spatial locations on cortex. Panel A of FIG. 21 depicts a probabilistic template of amygdala partitions that is applied to all individuals in a group analysis. Panel B of FIG. 21 shows the connectivity patterns to cortex of each of the three probabilistic partitions in a group analysis of 120 subjects. Note the high degree of similarity across these cortical maps (Pearson's r range from 0.88 to 0.92). The right side of panel B shows the average connectivity of each amygdala partition to a subset of 7 cortical networks. Cortical networks are derived from a group-average network definition based on the same 120 subjects. Note again the high degree of similarity in partition-network connectivity values across the 3 probabilistic groups. In FIG. 21, WU stands for Washington University group dataset of 120 subjects, DMN for default mode network, FP for frontoparietal network, DAN for dorsal attention network, VAN for ventral attention network, SN for salience network, CON for cingulo-opercular network, and FACE for face somatomotor network.

Functional Connectivity of Individualized Amygdala Subdivisions

Figure 22C:
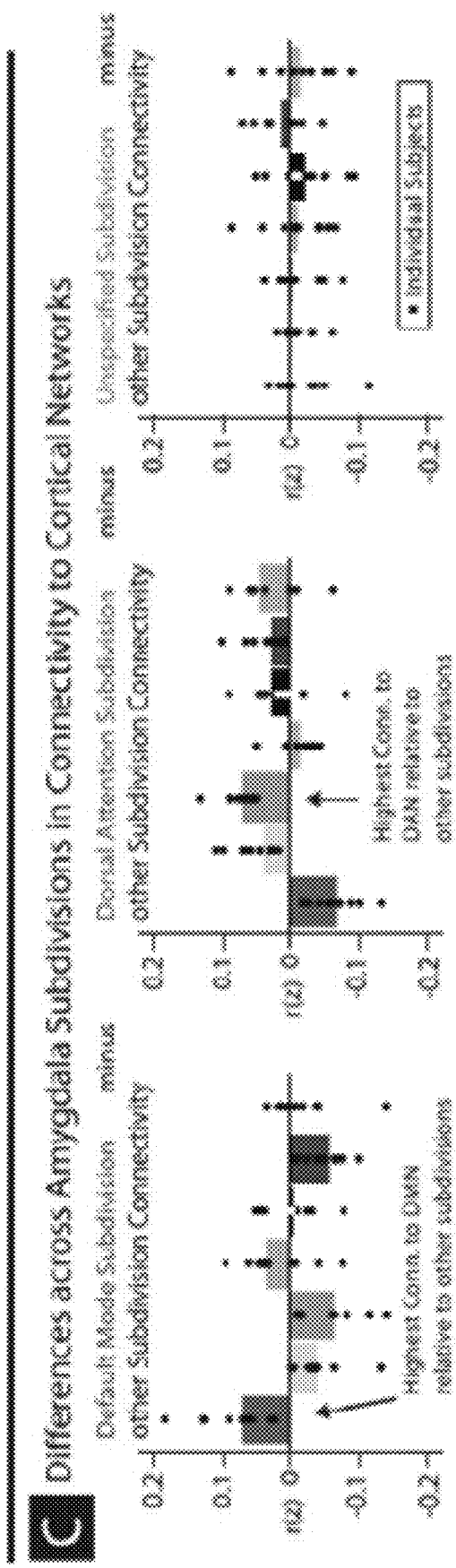
FIG. 22C shows differences across amygdala subdivisions in connectivity to cortical networks.
Figure 22D:
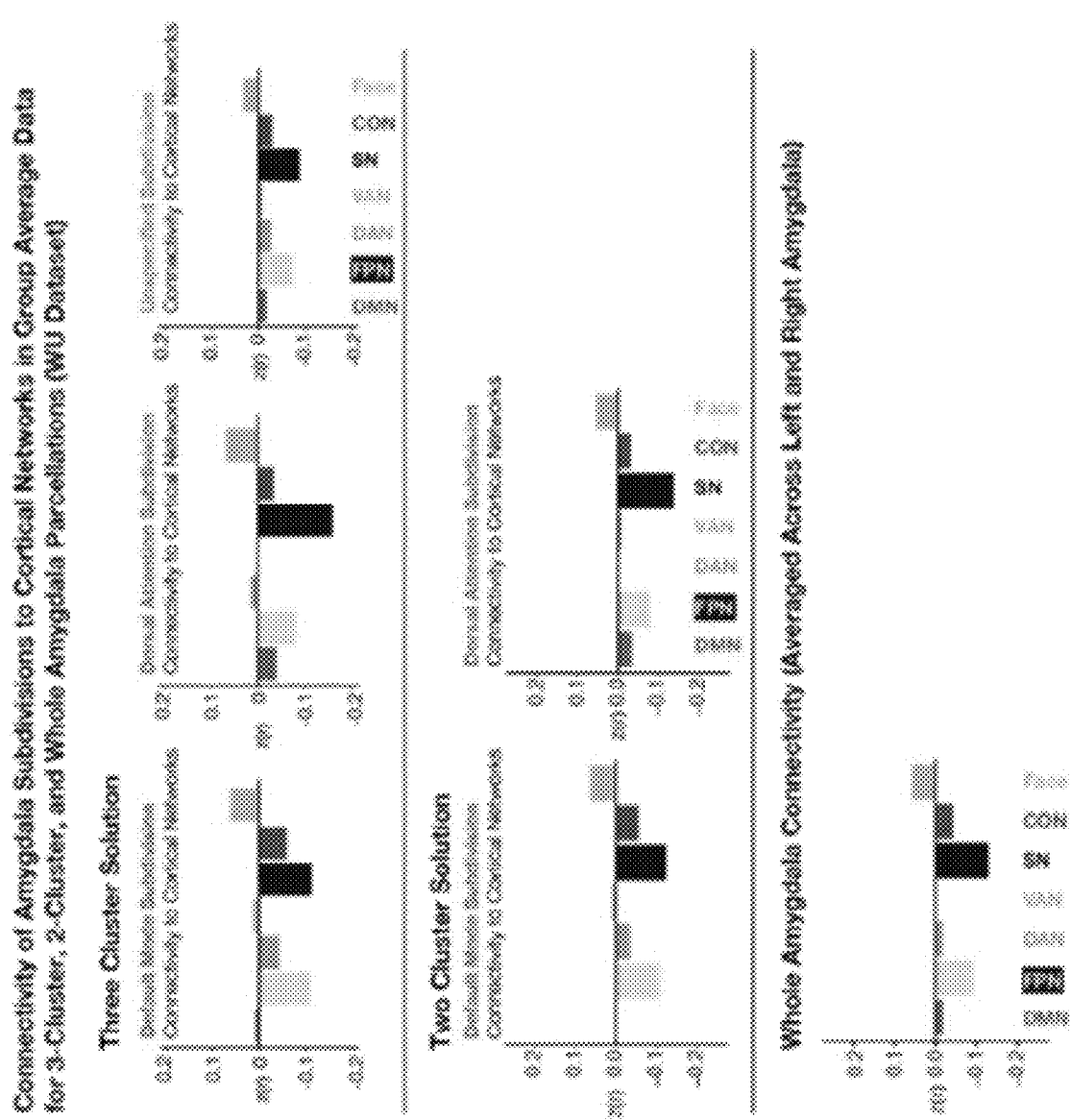
FIG. 22D shows connectivity of amygdala subdivisions to cortical networks in group average data.

The cortical functional connectivity of each of the 3 empirically and individually defined amygdala subdivisions in each of the MSC individuals were next computed (FIG. 22A). FIG. 22A-22D show individually generated amygdala subdivisions reveal that the amygdala has one subdivision that is selectively functionally connected to the default mode network and another that is selectively functionally connected to the dorsal attention network. FIG. 22A depicts the division of the amygdala into 3 subdivisions in four MSC individuals using k-means clustering. Voxels within the same subdivision tend to have homogenous patterns of connectivity to cerebral cortex. Clustering is done separately in each individual and a similarity algorithm based on connectivity to cortex is used to match subdivisions across individuals. The left side of FIG. 22B depicts connectivity of each amygdala subdivision to cortex in individual MSC01. The right side of FIG. 22B provides bar graphs that indicate the average functional connectivity of each subdivision to a subset of seven functional brain networks. Bar height indicates the median across the 10 MSC individuals, with each individual computed separately on the basis of his or her own network map. Dots indicate datapoints for each individual. FIG. 22C provides bar graphs that depict network connectivity of each subdivision minus network connectivity of the average of the other two subdivisions. This metric is referred to as 'selectivity.' Bars thus depict a measure of each subdivision's network connectivity relative to the rest of the amygdala. Individual dots represent datapoints for each individual. FIG. 22D shows bar graphs that indicate the average connectivity of each subdivision to each functional brain network in the WU group-average dataset. Graphs are computed for the 3-cluster amygdala solution (Panel A) as well as an alternative 2-cluster solution (Panel B) and the whole amygdala (Panel C).

Each of the empirically defined subdivisions had unique patterns of connectivity to cortical networks (FIG. 22B). Naming of subdivisions is based on connectivity profiles to cortex (see FIG. 22C), for example, subdivisions were named according to the network with which they had the highest positive connectivity relative to the other two subdivisions. A default mode subdivision had a higher magnitude of positive correlation to the DMN relative to the other two, as determined by paired t-tests across the 10 MSC individuals, (p<0.005). A dorsal attention subdivision had higher positive connectivity to the DAN (p<0.001) and fronto-parietal network (FPN, p=0.001) relative to the other two subdivisions. An unspecified subdivision was not uniquely positively correlated to specific networks relative to the other subdivisions, but rather only had connectivity properties that were shared across all 3 subdivisions. The whole-brain connectivity pattern of the unspecified subdivision was also the least similar across individuals (average pairwise correlation=0.29) relative to the default mode (average pairwise correlation=0.45) and dorsal attention (average pairwise correlation=0.35) subdivisions.

Empirical clustering of the amygdala using the group-average WU dataset also yielded default mode, dorsal attention and unspecified subdivisions, replicating the results from the MSC dataset (FIG. 22D). To compare results from the MSC versus WU datasets, 'selectivity' is the difference between a cluster's connectivity to a cortical network and the average of the other two clusters' connectivity to the same network. The selectivity of the default mode and dorsal attention subdivisions for their respective networks was on average 2.2 times larger in the MSC dataset compared to the WU dataset. Similarly, within the MSC dataset, network selectivity was 2.3 times larger when using the individualized amygdala subdivisions compared to using the standard group-based template subdivisions, indicating that the individually defined subdivisions better capture network-specific functional connectivity properties of amygdala partitions in individuals than the group-based template subdivisions.

In addition to each subdivision having unique features of connectivity with cortex, many features of connectivity with cortex were shared across all three subdivisions (FIG. 22B). For example, activity in all three subdivisions was positively correlated with activity in the ventral attention (VAN) and somatomotor (SMN) networks; and negatively correlated with activity in the cingulo-opercular (CON) and salience (SN) networks. These patterns were evident in both the individual MSC participants (FIG. 22B) and the group-average WU dataset (FIG. 22D).

Amygdala Functional Connectivity Respects Functional Brain Network Boundaries

Whether network specificity of amygdala subdivision functional connectivity is better captured by group-averaged functional boundaries or individual-specific functional boundaries was tested. For this analysis, functional connectivity between the amygdala default mode subdivision and a region of interest (ROI) defined within medial prefrontal cortex (mPFC) was chosen to be evaluated, because of the role of amygdala-mPFC connectivity in psychiatric illnesses.

Figure 23:
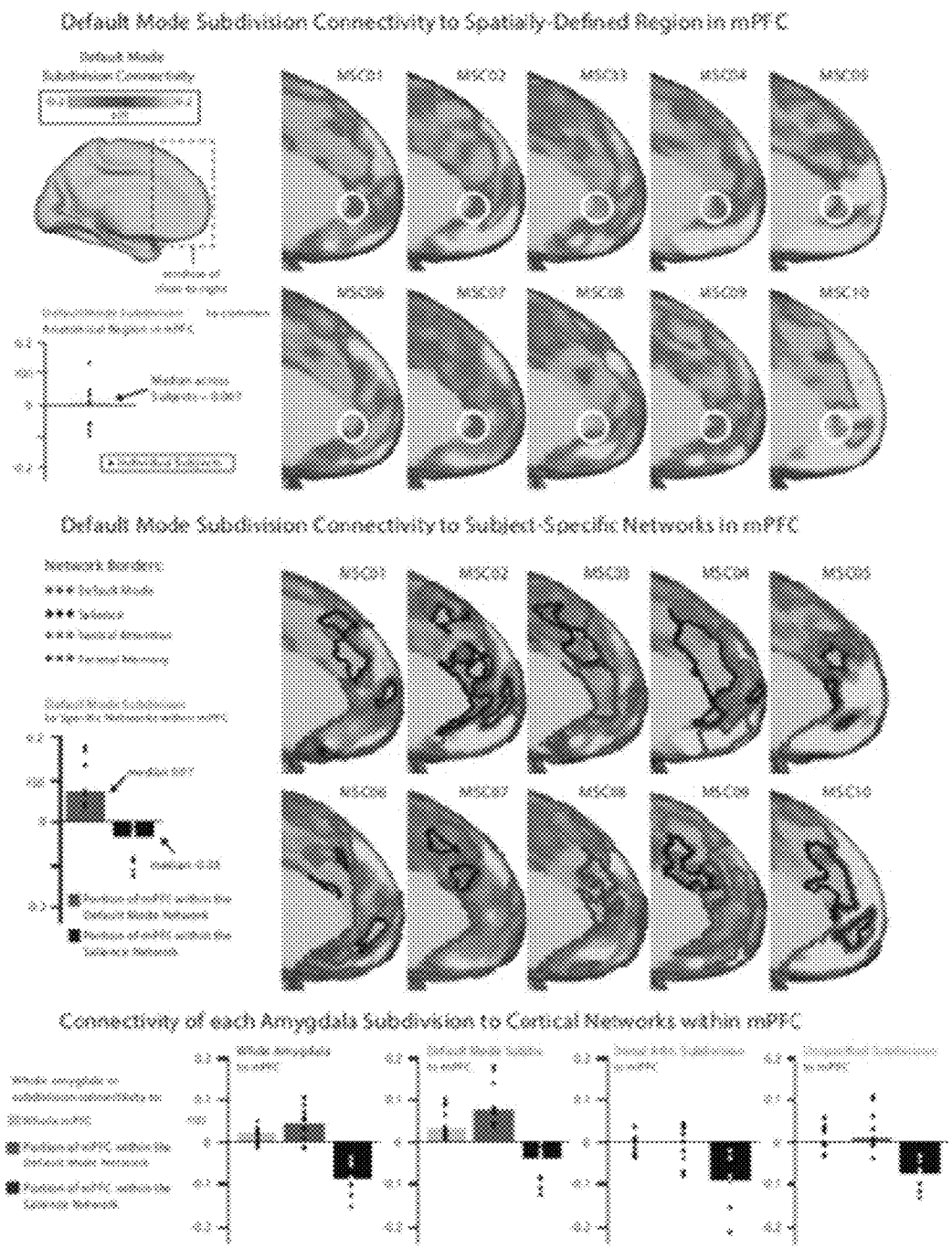
FIG. 23 shows connectivity to medial prefrontal cortex (mPFC)

FIG. 23 shows topography of amygdala functional connectivity to cortex respects individual-specific functional networks boundaries. Panel A of FIG. 23 depicts functional connectivity each individual's amygdala default mode subdivision to a common, group-defined ROI centered in the mPFC at [0 33 0] in Talairach space. In Panel A, a common anatomical ROI is placed over the connectivity map of the amygdala default mode subdivision in each MSC individual. This anatomical region is derived from a meta-analysis of mPFC regions in which connectivity with the amygdala is related to internalizing symptoms. Note the high degree of heterogeneity in the sign and magnitude of connectivity to this stereotactically defined region. The bar graph on the left depicts median connectivity across the ten individuals, and dots indicate connectivity values for each individual. Across individuals, even when using the individualized amygdala default mode subdivisions, connectivity with this group-derived mPFC region was not significantly different from zero (mean=−0.007, t(9)=−0.3, p=0.77).

Individual-specific amygdala default mode subdivision functional connectivity with individual-specific functionally defined locations within the mPFC was measured (Panel B of FIG. 23). In Panel B of FIG. 23, individual-specific network boundaries are overlaid on individual amygdala functional connectivity maps for the default mode subdivision. The bar graph on the left depicts connectivity to specific networks within the mPFC; note that connectivity to these functionally defined, individual-specific regions is much more consistent than connectivity to the anatomical region in Panel A. In all 10 individuals, amygdala default mode subdivision connectivity was positive to the individually-defined DMN portion of mPFC (M=0.11, t(9)=4.7, p=0.001) and negative to the individually-defined SN portion of mPFC (M=−0.06, t(8)=4.0, p=0.004). While the location of the DMN within the mPFC had moderate overlap across individuals (average Dice coefficient: 0.61), the location of the SN was highly variable across individuals (average Dice coefficient 0.07). In all individuals, there is an island of negative functional connectivity within the mPFC that usually corresponds to the individual-specific location of the SN. Surrounding areas of positive functional connectivity to the mPFC generally fall within individual-specific boundaries of the DMN. These features are lost in the group average because of individual variation in the location of the SN within the mPFC. Because the location of the SN varies across individuals, the connectivity of the amygdala default mode subdivision to any particular stereotactic location is highly variable, and depends on the individual-specific network layout of the mPFC. These analyses suggest that, within the mPFC, connectivity with particular stereotactic locations is variable across subjects because different individuals have different networks at those locations.

Panel C of FIG. 23 illustrates that the positive connectivity to DMN portions of mPFC are specific to the default mode subdivision and are not features of either the dorsal attention or somatomotor subdivisions. The bar graphs display the average amygdala functional connectivity to the entire mPFC. The gray bars display average connectivity across the entire mPFC while the red and black bars indicate average connectivity to the subset of the mPFC region that is within the DMN and SN, respectively. Separate bar graphs are presented for each subdivision within the amygdala.

Temporal Relationships of Amygdala Functional Connectivity to Cortex

Figure 24:
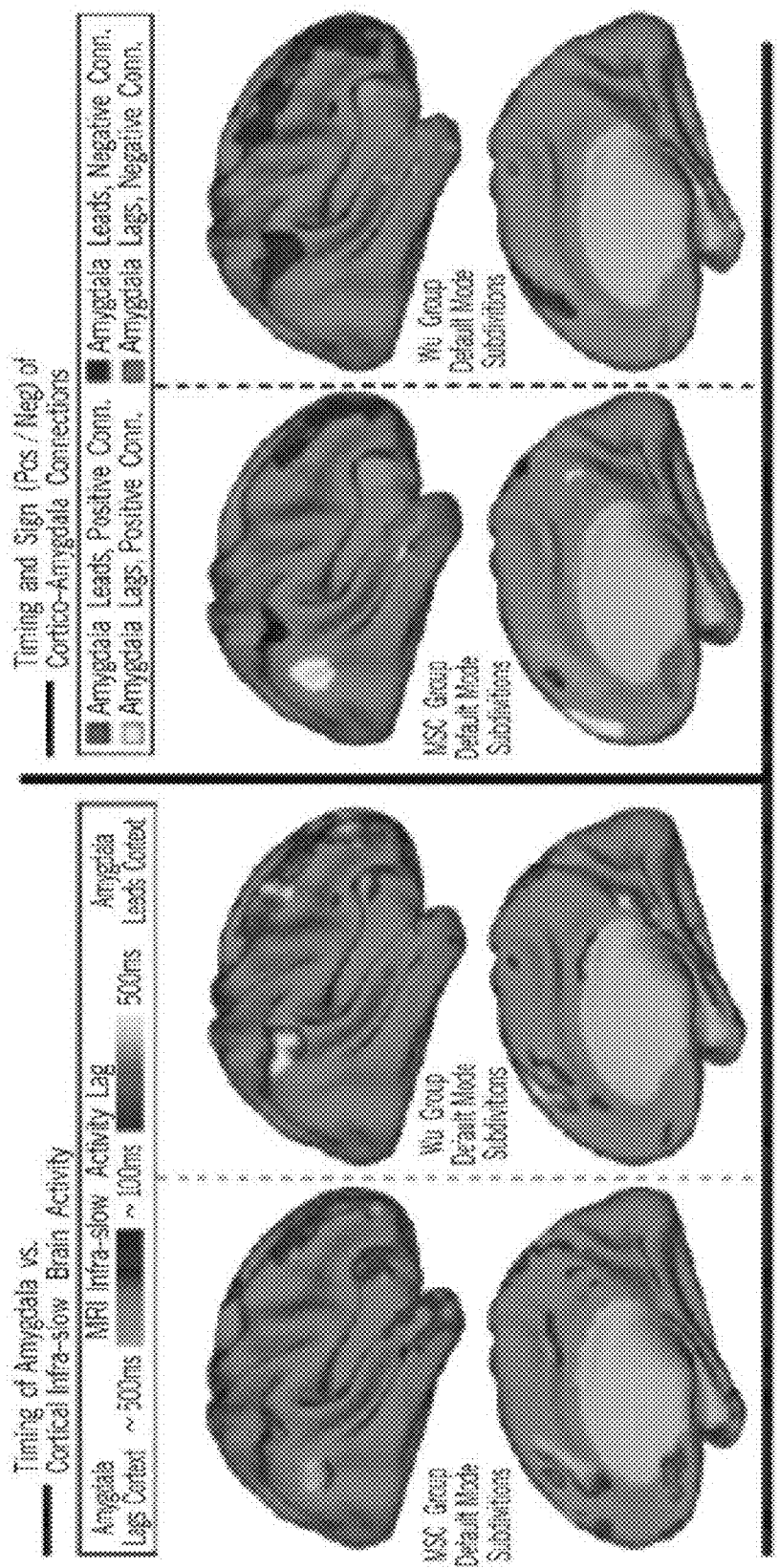
FIG. 24 shows results of a lag analysis.
Figure 24:
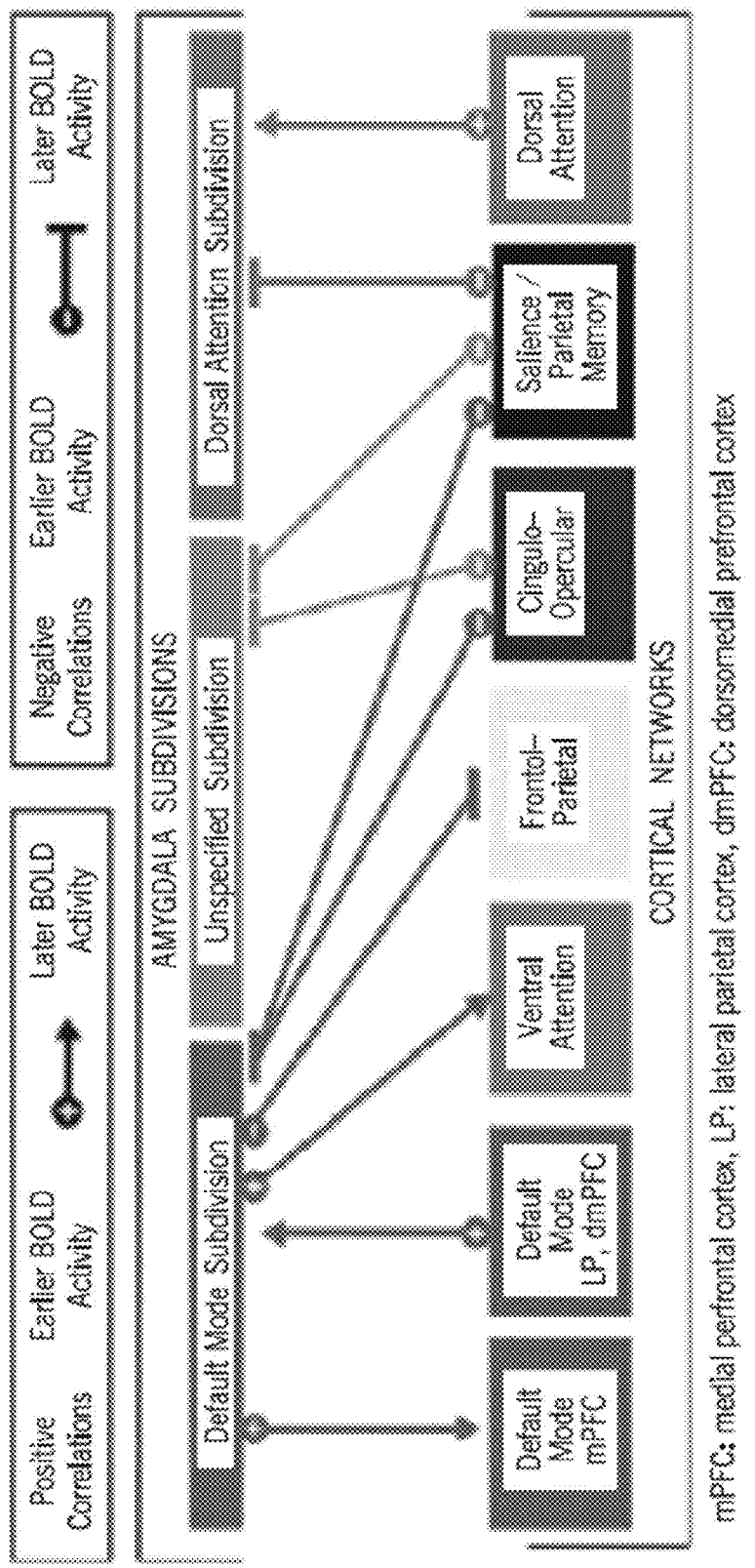

Lag analysis was used to explore the temporal ordering of ISA within the most robust (absolute magnitude>0.1) cortico-amygdalar functional connections (FIG. 24). FIG. 24 shows that Lag analysis reveals the temporal ordering of ISA in each amygdala subdivision relative to cortical networks. Panel A of FIG. 24 depicts lag relations between amygdala and cortical BOLD signals in the MSC and WU group-averaged datasets. Lag relations are shown only for amygdala-cortical connections in which the magnitude of the underlying correlation is |r|>0.1, because lag relations for lower correlations are less reliable. The lag relations for the default mode subdivision are depicted. Note the high degree of similarity across the two datasets. Panel B of FIG. 24 illustrates a conjunction map between the sign of functional connectivity (positive versus negative) and the lag direction (amygdala leads versus lags) of default mode subdivision functional connectivity to cortex. Panel C of FIG. 24 summarizes the position of the amygdala subdivisions within the larger network organization of the human brain. This schematic displays both the sign and timing of connections between the amygdala subdivisions and cortical networks. In Panel C, dmPFC stands for dorsomedial prefrontal cortex, and LP for lateral parietal cortex.

Amygdala subdivisions occupied consistent temporal positions within the larger network organization of the human brain across the MSC and WU datasets. Specifically, fMRI activity in the amygdala default mode subdivision preceded activity in the VAN and the mPFC portion of the DMN. In contrast, the amygdala default mode subdivision lagged behind other parts of the DMN such as the lateral parietal cortex. The amygdala default mode subdivision also preceded fMRI activity in the FPN but lagged behind activity in the SN, CON, and parietal memory (PMN) networks; but fMRI activity between the default mode subdivision and each of these networks was negatively correlated. The amygdala dorsal attention subdivision lagged behind the DAN as well as the anti-correlated SN and PMN. Finally, the amygdala unspecified subdivision lagged behind the CON, SN, and PMN, all of which were anticorrelated with this subdivision.

An individualized approach is used for functional connectivity estimation to characterize the human amygdala and its subdivisions as part of the brain's global functional network organization. Three amygdala subdivisions each occupy roughly consistent locations across subjects and exhibit consistent functional connectivity with specific cortical functional networks. Specifically, one amygdala subdivision that is located superior in most individuals and has preferential functional connectivity to the DMN; a second amygdala subdivision that is located medial in most individuals and has preferential functional connectivity to the DAN; and a third amygdala subdivision that is located ventral in most individuals and does not have any networks to which it is preferentially positively correlated. fMRI activity in all three subdivisions is positively correlated with activity in the VAN and SMN as well as negatively correlated with activity the in CON and SN. Consistent temporal relations were detected between each amygdala subdivision and cortical functional networks in two independent datasets (WU and MSC). Notably, the stereotactic positions of both the amygdala subdivisions and the cortical functional networks varied across subjects. As a result, standard template-based approaches to measuring amygdala connectivity often capture different functional connections in different individuals. In addition to informing the basic biology of the amygdala, this work provides a framework for developing mechanistic, biologically plausible models of amygdala function and dysfunction in individual subjects.

A Network-Based Framework for the Amygdala and its Subdivisions

A 'network-based framework' is used for conceptualizing amygdala functional connectivity with cortex in humans based on the observations of the magnitude and direction of connectivity between amygdala subdivisions and cortical networks outlined here. fMRI time delays likely reflect ISA (<0.1 Hz) neurophysiology. Prior work suggests that ISA generally propagates in a direction opposite to higher frequency (e.g. delta) activity. According to a "sender-receiver" model, then, ISA propagates from a "receiver" to a "sender" of higher frequency activity that is more likely to carry feed-forward information. The following is framed based on this model.

Key elements of the proposed network-based framework of amygdala connectivity with cortex are (1) a 'default mode' amygdala subdivision that integrates salient environmental information and past history regarding the emotional significance of these salient stimuli, (2) a 'dorsal attention' amygdala subdivision that modulates top-down attention networks, and (3) a fundamental 'push-pull' relation between activity in all 3 subdivisions of the amygdala and brain networks implicated in cognitive control. This network-based framework only becomes evident after studying individuals, because variation in the stereotactic location of amygdala subdivisions and cortical networks obscures these properties in group-average datasets.

The functional connectivity of the default mode subdivision suggests that it may integrate salient environmental information and its learned emotional significance to influence memory and cognitive brain networks. When viewed from the vantage of the sender-receiver model, the amygdala default mode subdivision is a receiver in relation to the VAN and the mPFC portion of the DMN. The VAN is implicated in the bottom-up, involuntary orientation of spatial attention to salient stimuli, while the mPFC is implicated in extinction recall, the implicit signaling that a formerly threatening stimulus is no longer dangerous. The amygdala default mode subdivision is a sender in relation the lateral parietal cortex (LPC) portion of the DMN, which has been linked to recall of episodic memory. Taken together, these results are consistent with a role of the amygdala default mode subdivision in integrating information regarding the presence of salient stimuli and the past emotional significance of these stimuli in order to influence downstream memory systems.

The amygdala default mode subdivision is also a receiver in relation to the FPN and a sender in relation to the CON, SN, and PMN; however, ISA in the default mode subdivision is negatively correlated with ISA in each of these networks. These results are consistent with a relative 'push-pull' relation between the functioning of cognitive control networks such as the FPN and CON and the functioning of emotionally-based circuitry that includes the amygdala. These results further suggest that this push-pull dynamic has a specific directionality in the sender-receiver model, namely FPN 4 amygdala default mode subdivision 4 CON and SN. A speculative possibility is that these amygdala-network relations underlie the relative switch between emotional and cognitive processing.

The dorsal attention subdivision may influence the top-down control of spatial attention. This subdivision is a sender in relation to the DAN, which has been implicated in using goals in order to direct attention. Many psychiatric disorders are associated with a bias in attention towards emotional stimuli, such as a bias to attend to sad stimuli in major depression and threatening stimuli in anxiety disorders. A speculative possibility is that the amygdala dorsal attention subdivision mediates this top-down bias in attention.

Both the dorsal attention and unspecified subdivisions are senders in relation to the SN and PMN; the unspecified subdivision is also a sender in relation to the CON. All of these subdivision-cortical interactions involve negative correlations in ISA, suggesting that they may relate to the push-pull shifts between controlled and emotionally-based processing.

Considerations for Defining Amygdala Subdivisions

Three subdivisions are used as an example only. The number of subdivisions may be in other numbers, such as two. A 2-cluster solution is described in Supplement. The 2-cluster solution yielded subdivisions with connectivity properties similar to the default mode and dorsal attention subdivisions from the 3-cluster solution. The 'optimal' number of subdivisions within the amygdala, defined by unique patterns of connectivity to cortex, is likely to evolve as a function of data quality and scanner resolution. Further, different subdivision schemes may provide complementary sources of information about the underlying biology of the amygdala.

Relevance of the Network-Based Framework to Neuropsychiatric Illnesses

The rich network-based framework revealed by the individual-functional approach lays the foundation for creating models of amygdala function and dysfunction in individual subjects. Disrupted connectivity between the mPFC and amygdala is frequently implicated in psychiatric disorders, as the mPFC is theorized to regulate amygdala activity implicitly via extinction memory. The current results are consistent with a model in which the default mode amygdala subdivision is positively correlated with, and is a receiver in relation to, portions of the mPFC that are part of the DMN; while all three amygdala subdivisions are negatively correlated with, and senders in relation to, the portion of the mPFC that is SN. The next step is to determine whether psychiatric disorders are associated with dysfunction (either in timing or connectivity strength) in one or all of these connections. The disordered individually defined functionally-based connection is likely to serve as a better biomarker than current group-derived stereotactic-based connections. The model proposed herein also suggests that intervention in these different functionally-based connections has different downstream effects on the amygdala and other cortical networks. Interventions such as deep brain stimulation (DBS) or transcranial magnetic stimulation (TMS) that stimulate the DMN within the mPFC may be expected to increase activity in the default mode subdivision, and perhaps cause downstream activity changes in the lateral parietal cortex. Stimulation of the SN within the mPFC, on the other hand, is likely to have different effects. A corollary is that stimulation of the same stereotactic location in different people is likely to affect different functional circuits and have different downstream effects; such variability may explain heterogeneity observed in stimulation-based treatments.

The network-based framework of amygdala functional connectivity outlined in this study serves as the foundation for creating models of dysfunction in individual subjects. For example, particular groups of subjects are characterized by specific alterations in the timing and strength of amygdala subdivision functional connections to particular networks (i.e., different 'biotypes'). For example, a subset of subjects with anxiety disorders may have increased connectivity between the VAN and the default mode subdivision of the amygdala, with a shorter delay in ISA relative to healthy individuals. Timing beyond a predefined range of the timing for a healthy individual may be referred to as abnormal timing. The network-based model predicts that this increased correlation may drive downstream effects in, e.g.

the lateral parietal cortex. Furthermore, specific interventions may be indicated to address this alteration, such as TMS of the VAN or cognitive training programs that decrease VAN activity.

The work in the current study uses high sampling of individuals to place the amygdala and its subdivisions within the larger network organization of the human brain. This model is used as a framework for developing biologically plausible biomarkers and targets for intervention in individual subjects with psychiatric disorders.

Subjects

Two independent datasets were used for this study. The Midnight Scan Club (MSC) subjects were ten healthy, right-handed, young adult participants (5 females; age: 24-34) recruited from the Washington University community and included the senior author (NUFD). The replication Washington University (WU) dataset was an independent group-average dataset of 120 adults (60 males; average age 25 years, range 19-32 years). Methods for processing of this replication dataset are provided in Supplementary Methods. The Washington University School of Medicine Human Studies Committee and Institutional Review Board approved the study and informed consent was obtained from all participants.

MRI Image Acquisition

Imaging for the MSC individuals was performed on a 3T MRI scanner over the course of 12 separate sessions (per subject) and included four T1-weighted images and four T2-weighted images. Each subject underwent ten 30 minute resting state functional MRI (rs-fMRI) scans over the course of ten separate days, for a total of 300 minutes of data per subject.

Resting State Functional Connectivity Analyses rs-fMRI preprocessing, functional connectivity processing, creation of cortical surfaces, mapping of BOLD data to subject-specific surfaces, combination of surface and volumetric data, and generation of subject-specific functional brain network topographies has been previously described and are detailed in the Supplementary Methods. Amygdala ROIs were generated by FreeSurfer 5.3, hand-edited by an individual with substantial prior experience, and reviewed for accuracy by a neuroradiologist. Amygdala ROIs were resampled to 2×2×2 mm isotropic space and ranged from 205 to 273 voxels (summed across the two hemispheres).

The resting state functional connectivity (rs-fc) of each voxel in the amygdala was computed for each subject. The time series of each amygdala voxel was correlated with each cortical vertex, regressing out cortical signal within 20 mm of the amygdala for additional artifact removal. k-means clustering was used to empirically divide the individual amygdala voxels in each subject into 3 partitions on the basis of each voxel's connectivity pattern to cortex. Three clusters were used in an attempt to define individualized versions of the 3 amygdala groups commonly explored in the prior literature on amygdala functional connectivity. A similarity algorithm was used to empirically match clusters across subjects. After deriving 3 clusters within the amygdala for each subject, subsequent analyses examined cluster-wise connectivity patterns. rs-fc processed BOLD time series were averaged across clusters for each subject and rs-fc to cortex was re-computed, as above, for these cluster-averaged time series. For network-level analyses, The correlation values were averaged across cortical vertices within particular networks that were determined at the individual-subject level in a prior study. For the analysis of the medial prefrontal cortex (mPFC), a region of interest was used, which was derived from a meta-analysis relating amygdala-mPFC connectivity to internalizing symptoms. The temporal ordering of signals in amygdala clusters versus cortex was determined using lag analysis as detailed in the Supplementary Methods. Split-half reliability was computed for most measures to assess group- and individual-level reliability.

Methods rs-fMRI preprocessing included correction of intensity differences attributable to interleaved acquisition, intensity normalization of each run to a whole brain mode value of 1000, linear realignment within and across runs to compensate for rigid body motion, and linear registration of BOLD images to a Talairach atlas template, via the T2 and T1 weighted images. In addition, field map correction was performed by using a mean field map generated from all 10 subjects. Atlas transformation, mean field distortion correction, and resampling to 3-mm (cortex) or 2-mm (amygdala) isotropic atlas space were combined into a single interpolation using FSL's applywarp tool.

Following pre-processing, volumes with frame-by-frame displacement greater than 0.2 mm or DVARS exceeding 5.36 were censored. Censored frames were replaced via linear interpolation. Interpolated time series and motion parameters were subsequently filtered between 0.005 and 0.01 Hz. Filtered time series underwent regression of the global signal and principal components derived from the six motion parameters and signals taken from nuisance regions. Censored frames were then excised for all subsequent analyses.

Cortical Surface Generation and Processing

FreeSurfer version 5.3 was used to create initial white and gray matter segmentations for each subject. These segmentations were hand-edited and then processed with the recon-all processing pipeline in FreeSurfer to create white matter and pial surfaces. Subsequently, spherical registration was used to align each subject's surface to the fsaverage surface. The fsaverage surface for each subject was then registered to the "fs_LR" surface, resampled to a resolution of 164,000 vertices and then downsampled to 32,492 vertices, and finally transformed into Talairach atlas volumetric space by applying the T1-to-atlas transformation previously calculated.

These transformations used Caret tools and scripts available on the Van Essen laboratory website (Freesurfer_to_fs_LR Pipeline, http://brainvis.wustl.edu).

BOLD fMRI volumetric time series were sampled to each subject's original mid-thickness left and right-hemisphere surfaces using the ribbon-constrained procedure in Connectome Workbench 1.0. Voxels with a time series coefficient of variation 0.5 standard deviations higher than the mean coefficient of variation of nearby voxels (within a 5 mm sigma Gaussian neighborhood) were excluded from the volume to surface sampling. Once sampled to the surface, timecourses were deformed and resampled from the individual's original surface to the 32 k fs_LR surface in a single step using the deformation map generated above. This resampling allows point-to-point comparison between each individual registered to this surface space.

These surfaces were combined with volumetric amygdala data into the CIFTI format using Connectome Workbench, creating full brain timecourses excluding non-gray matter tissue. Finally, the resting-state timecourses for surface data were smoothed with geodesic 2D Gaussian kernels (a=2.55 mm). Volumetric (amygdala) time series were not smoothed, to avoid contamination from nearby subcortical structures (i.e. the hippocampus).

Amygdala Regions-of-Interest

The output "aseg" amygdala segmentations from the FreeSurfer pipeline were manually edited by a single experienced rater (DA) using ITK-SNAP software. For this procedure, outlines were inspected and adjusted in the coronal view of the T1-weighted image from posterior to anterior sections. The segmentations were subsequently modified in the axial and sagittal views. The left and right hemispheres were independently outlined. The amygdala definitions used in the editing process followed previously published protocols. All segmentations were reviewed by a neuroradiologist (JS). The segmentations were then resampled into 2×2×2 mm voxels for most fMRI analyses. Combined across left and right hemispheres, the median amygdala volume in 2×2×2 mm space across the 10 subjects was 1960 mm$^3$ (range 1640 mm$^3$ to 2184 mm$^3$).

Vertex-Wise Network Mapping

The network organization of each subject's cortical surface was derived using the graph theory-based Infomap algorithm for community detection, following methodology from previous studies. The Pearson correlation matrix of the time courses from all cortical vertices were calculated. Correlations between vertices within 30 mm of geodesic distance from each other were set to zero. This matrix was thresholded at a range of densities, from 0.1% to 5%, and the Infomap algorithm was used to calculate community assignments (network identity) separately for each threshold. Networks with 400 or fewer vertices were removed from further consideration. The label for each network, at each threshold, was performed using a matching technique to a reference template. In each individual and in the average, a "consensus" network assignment was derived by giving each node the assignment to which it had the greatest number of community assignments across thresholds.

Following these procedures, contiguous network pieces that were smaller than 30 mm$^2$ were removed. Neighboring network identities were then dilated into the removed areas. This procedure to identify networks was conducted in each individual subject, and in data averaged across all subjects.

Subject Motion During fMRI

In 2 subjects (MSC03 and MSC10), a high-frequency artifact contaminated motion estimates in the phase encode (anterior-posterior) direction. The motion timecourses were filtered to retain only frequencies<0.1 Hz in the anterior-posterior direction in these two subjects. Across all subjects, 28%±18% (range: 6%-67%) of the data were censored; on average, subjects retained 5929±1508 volumes (range: 2733-7667).

k-Means Clustering

The amygdala was empirically divided into 3 functional subdivisions in each subject on the basis of connectivity patterns to cortex. In each subject, a m×n matrix was derived, in which m is the number of voxels in the bilateral amygdala (using 2×2×2 mm isotropic voxels) and n is the number of cortical vertices not in the medial wall (59412 using fs_LR_32 k surface space). Each entry in the m×n matrix therefore represents the correlation in activity between a particular amygdala voxel and a particular cortical vertex. The 'kmeans' program within Matlab was then used to partition each subject's matrix into 3 partitions, returning an m×1 vector in which each entry categorizes an amygdala voxel into one of the three clusters. Thus, each amygdala voxel is empirically partitioned into one of three clusters (functional subdivisions) such that connectivity of voxels within a subdivision is relatively homogenous.

A similarity algorithm was then used to empirically match amygdala subdivisions across subjects. The connectivity of each subdivision to cortex in each subject was computed, resulting in 30 cortical connectivity maps (10 subjects×3 subdivisions in each subject). The correlation between each pair of maps were computed, resulting in a measure of similarity between connectivity maps across all subdivisions in all subjects. If a particular partition A in Subject 1 was most highly correlated with partition B in Subject 2, and partition B in Subject 2 was also most highly correlated with partition A in Subject 1, these two partitions were said to be 'matched'. Partitions across subjects were grouped into subdivisions such that the maximum total number of 'matches' were within the same subdivisions.

The same procedures described above were also performed using k=2 and results from this separate clustering scheme are described in the SI Appendix Results.

Empirical Determination of the 'Optimal' Cluster Number

A stability metric was used to assess post hoc whether k=3 was a reasonable cutoff for the number of functional clusters within the amygdala. The stability of clusters for k=2 through k=9 was derived for each individual MSC subject, the MSC average dataset, and the WU group average dataset. For example, stability for each k for each dataset was computed 1000 times. For each iteration, the total number of amygdala voxels was randomly divided into two equal split-halves (subset A and subset B). k-means clustering was performed separately on each half. The voxels from subset B were then additionally assigned to the classifications derived from the k-means clustering of subset A. This procedure was done by assigning each voxel in subset B to the closest cluster center in subset A. In this case, cluster center corresponds roughly to the average vertexwise connectivity to cortex of the cluster. The Hamming distance between the vector of the assignments of subset B was computed based on its own k-means clustering and the vector of the assignments of subset B based on the closest center from subset A. The Hamming distance was computed for every possible permutation of labels of the solution derived from the k-means clustering of subset B, since the labels are arbitrary. The lowest Hamming distance computed from these permutations was the raw stability value for that iteration. Raw stability values were normalized by a 'randomized stability value' that was calculated separately for each k value and for each dataset. This randomized stability value accounts for the fact that the chance misclassification rate varies as a function of k. This randomized value is calculated by randomly assigning all voxels in subset B to k clusters two separate times, and then deriving the Hamming distance of these randomized assignments (including permuting labels as above and performing 1000 iterations).

Comparison of Clusters and Maps

Whole brain connectivity maps of individual clusters or probabilistic nuclei were compared by Pearson's correlation. For each comparison, the vertex-by-vertex whole cortex map from one cluster was correlated with the vertex-by-vertex whole cortex map from another cluster.

Variability in Amygdala Cluster Connectivity and Layout of Functional Brain Networks Across the MSC Subjects To derive variability in amygdala connectivity across subjects, the standard deviation in amygdala connectivity across subjects at each vertex was computed. To compute variability in network assignment, the most common network assignment at each vertex across the 10 subjects was determined. Network variability was defined as the number of subjects (out of 10) that did not have the most common network assignment at each vertex, such that higher numbers indicated more variability. To make conjunction maps, high variability in connectivity or network assignment was defined as vertices in which variability was above the cortex-wide median.

Lag Analysis

Time delay was estimated based on a lag analysis. For each subject, a lagged cross-covariance function between each pair of vertices/voxels was computed at a temporal resolution of the acquired data (volume TR=2200 ms). Lags were then more precisely determined by estimating the cross-covariance extremum using three-point parabolic interpolation.

For the MSC dataset, lag analysis was performed over 'blocks' of continuous high quality data (i.e. no frames had to be censored because of motion). Lags were examined for blocks in which FD<0.5 for at least 7 contiguous frames. Lags were computed for each block of continuous data and then session-level lag was computed by averaging lags across blocks within a session, weighted by the number of frames in each block. The average of the lag was computed at each vertex across the 10 sessions. For the WU group average dataset, the same procedure was employed, except that 'blocks' had to have FD<0.2 for at least 7 contiguous frames. Each subject in the WU dataset had a single session, and the average lag was computed at each vertex across subjects. In both the MSC and WU datasets, the lags were computed between functionally defined amygdala subdivisions (i.e. the default mode, dorsal attention, and unspecified subdivisions) and each cortical vertex.

In order to maximize reliability of lag estimates (see results below for reliability values), in the main analysis (e.g., FIG. 5), lags at each cortical vertex were averaged across the ten MSC subjects. Note, however, that prior to this cortical averaging, lags were computed on the basis of each individual subject's amygdala subdivisions, helping to mitigate some of the across-subject variation in functional biology noted throughout this study. In addition, lags of at least +/−150 ms are described, in which the zero-lag correlation was |r|>0.1, because these lags are considered reliable for the amount of data in the current dataset.

In the main text, lag information between each amygdala functional subdivision and the cortical networks that were most robustly positively or negatively correlated with the subdivision is summarized. The basis of this summary is provided in Table 1, which lists all of the significant lag relations detected in the MSC-group average dataset, including the network assignment for each amygdala-cortical connection.

TABLE 1

| | | | | | | |
|---|---|---|---|---|---|---|
| −10.40 | 31.64 | 22.57 | Salience | 322.04 | negative | lags |
| 31.02 | 25.15 | −1.18 | Salience | 93.85 | negative | lags |
| 34.38 | 6.07 | −19.25 | Cingulo-opercular | 52.15 | positive | leads |
| 31.32 | 0.21 | −45.95 | Anterior Medial Temporal | 760.31 | positive | leads |
| −28.93 | 2.13 | −43.67 | Anterior Medial Temporal | 238.76 | positive | leads |

TABLE 1-continued

| | | | | | | |
|---|---|---|---|---|---|---|
| −6.06 | −73.16 | 40.82 | Parietal Memory | 230.54 | negative | lags |
| −3.14 | −20.06 | 29.77 | Parietal Memory | 104.60 | negative | lags |
| 6.44 | −21.49 | 28.86 | Parietal Memory | 58.54 | negative | lags |
| 36.68 | −18.03 | −18.19 | Unknown | 38.67 | positive | lags |

Again, the average lag relation across the 10 MSC subjects was used for these summaries, in order to maximize reliability. The single exception is the summary of the dorsal attention cluster lag with the dorsal attention network on cortex. Because of high across-subject variation in the location of the dorsal attention network on cortex, there were no portions of cortex in the group-averaged cortical lag map that corresponded to the dorsal attention network. In this case, the lag between the dorsal attention subdivision and the dorsal attention network in each individual subject was computed, and is summarized across subjects.

What is claimed is:

1. A method of surgical planning, comprising:
using a computer system, acquiring magnetic resonance imaging data of a brain of a subject;
using a computer system and the magnetic resonance data, determining functional connectivity of the brain between a voxel in a subcortical region of the brain and a voxel in a cortical region of the brain;
identifying a target location in the brain to be targeted by neuromodulation based on the calculated functional connectivity; and
using a computer system, generating a report indicating the target location.

2. The method of claim 1, wherein determining functional connectivity comprises determining functional connectivity of the brain between the voxel in the subcortical region and each cortical functional network in a plurality of cortical functional networks.

3. The method of claim 1, wherein identifying a target location further includes identifying a winning functional network among the plurality of cortical functional networks as a functional network having the highest functional connectivity with the voxel.

4. The method of claim 3, wherein identifying a target location further includes integrating the voxel in the integrative zone when functional connectivity between the voxel and one or more functional networks is above a threshold.

5. The method of claim 4, wherein the one or more functional networks are among a remaining of the plurality of cortical functional networks minus the winning functional network.

6. The method of claim 4, further comprising identifying the target location to include the integrative zone.

7. The method of claim 6, further comprising identifying a given subcortical region as an integrative zone if a correlation between the given subcortical region and one or more functional networks other than the winning functional network is greater than a predetermined threshold.

8. The method of claim 7, wherein the threshold is 66 percent.

9. The method of claim 1, wherein the magnetic resonance data includes at least one of functional magnetic resonance imaging (fMRI) data or resting state (rs) fMRI data of the subject.

10. The method of claim 9, wherein acquiring fMRI data further comprises acquiring task fMRI data of the subject and determining functional connectivity further comprises determining functional connectivity based on the rs-fMRI data.

11. The method of claim 10, further comprising identifying at least one of an activation region and a deactivation region based on the acquired task fMRI data to derive a task fMRI map and validating the identified target location using the derived task fMRI map.

12. The method of claim 1, wherein determining functional connectivity comprises determining functional connectivity between the voxel in the subcortical region and a region of interest (ROI) in the cortical region.

13. The method of claim 1, wherein determining functional connectivity further comprises calculating timing of the functional connectivity between the voxel in a subcortical region and the voxel in the cortical region based on the magnetic resonance data.

14. The method of claim 13, wherein identifying a target location further comprises identifying a voxel having an abnormal timing compared to a healthy individual as the target location.

* * * * *